(12) United States Patent
Fomsgaard et al.

(10) Patent No.: US 9,764,024 B2
(45) Date of Patent: Sep. 19, 2017

(54) OPTIMIZED INFLUENZA VACCINES

(75) Inventors: Anders Fomsgaard, Lyngby (DK); Karoline Bragstad, Copenhagen N (DK)

(73) Assignee: Statens Serum Institut, Copenhagen (DK)

( * ) Notice: Subject to any disclaimer, the term of this patent is extended or adjusted under 35 U.S.C. 154(b) by 543 days.

(21) Appl. No.: 13/131,733

(22) PCT Filed: Nov. 27, 2009

(86) PCT No.: PCT/DK2009/000247
§ 371 (c)(1),
(2), (4) Date: May 27, 2011

(87) PCT Pub. No.: WO2010/060430
PCT Pub. Date: Jun. 3, 2010

(65) Prior Publication Data
US 2011/0229518 A1    Sep. 22, 2011

(30) Foreign Application Priority Data

Nov. 28, 2008 (DK) .................................. 2008 01688

(51) Int. Cl.
*A61K 39/145* (2006.01)
*A61K 39/12* (2006.01)
*A61K 39/00* (2006.01)

(52) U.S. Cl.
CPC ............ *A61K 39/145* (2013.01); *A61K 39/12* (2013.01); *A61K 2039/53* (2013.01); *A61K 2039/54* (2013.01); *A61K 2039/58* (2013.01); *A61K 2039/70* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 6,649,170 | B1 | 11/2003 | Lindblad et al. |
| 7,749,520 | B2 | 7/2010 | Davidsen et al. |
| 2002/0165176 | A1* | 11/2002 | Haynes et al. ............... 514/44 |
| 2004/0057963 | A1 | 3/2004 | Andersen et al. |
| 2004/0087521 | A1* | 5/2004 | Donnelly et al. ............ 514/44 |
| 2005/0191308 | A1 | 9/2005 | Lindblad et al. |
| 2006/0024670 | A1 | 2/2006 | Luke et al. |
| 2007/0031453 | A1* | 2/2007 | Hoffmann ............ A61K 39/12 424/209.1 |
| 2008/0008724 | A1 | 1/2008 | Aagaard et al. |
| 2010/0015171 | A1 | 1/2010 | Dietrich et al. |
| 2010/0160421 | A1 | 6/2010 | Fomsgaard |

FOREIGN PATENT DOCUMENTS

| WO | WO2006/063101 | A1 | 6/2006 |
|---|---|---|---|
| WO | WO2006/082398 | A2 | 8/2006 |
| WO | WO2007/019094 | A2 | 2/2007 |
| WO | WO 2008/021412 | * | 2/2008 |
| WO | WO2008/145129 | A2 | 12/2008 |
| WO | WO2009150532 | * | 12/2009 |
| WO | WO2010036970 | * | 4/2010 |

OTHER PUBLICATIONS

GenBank Accession# Q8BAC3, Matrix protein 1 (M1), Jan. 15, 2008.*
GenBank Accession# Q8BAC4, Matrix protein 2 (Proton channel protein M2), Jan. 15, 2008.*
GenBank Accession# Q5UEW0, Nucleoprotein, Oct. 31, 2006.*
Ko et al., Optimization of Codon Usage Enhances the Immunogenicity of a DNA Vaccine Encoding Mycobacterial Antigen Ag85B, 2005, Infection and Immunity, vol. 73, No. 9, pp. 5666-5674.*
GenBank Accession# ABW80978, hemagglutinin [Influenza A virus (A/Wisconsin/67/2005(H3N2))], Mar. 2008.*
GenBank Accession# ABP52004, neuraminidase [Influenza A virus (A/Wisconsin/67/2005(H3N2))], Apr. 2008.*
Mishin et al., Effect of Hemagglutinin Glycosylation on Influenza Virus Susceptibility to Neuraminidase Inhibitors, 2005, Journal of Virology, vol. 79, No. 19, pp. 12416-12424.*
Bragstad et al, New Avian Influenza A Virus Subtype Combination H5N7 Identified in Danish Mallard Ducks, Virus Research, 109, pp. 181-190, (May 2005).

(Continued)

*Primary Examiner* — Benjamin P Blumel
(74) *Attorney, Agent, or Firm* — Howson & Howson LLP

(57) ABSTRACT

The invention concerns nucleotides vaccines encoding influenza proteins with few or no glycosylation sites. Since these first introductions of pandemic influenzas the viruses have drifted, accumulating mutations at antigenic sites, but also the N-glycosylation pattern has changed during the drifted years, accumulating N-linked glycosylation sequons that help mask the antigenic sites for recognition by the host immune system. These "naked" initial haemagglutinins induce a broad cross reactivity against widely drifted influenza subtypes. The origin of the DNA or RNA can be both pandemic influenza strains, which codes for proteins which have a naturally low content of glycosylation sites and/or DNA or RNA from non-pandemic influenza strains where the nucleotides have been mutated or changed so it encodes for proteins with less or no glycosylation sites. The invention also discloses DNA or RNA encoding the haemagglutinin (HA) from pandemic influenza A, e.g. the 1918 H1N1 and/or the 1957 H2N2 and/or the 1968 H3N2 influenza A virus, optionally with the Neuraminidase (NA) and/or matrix protein (M) and/or the nucleoprotein (NP) from these pandemic influenza virus included, mixed together with DNA or RNA from non-pandemic influenza A as a vaccine against present day and future influenza A viruses.

16 Claims, 12 Drawing Sheets

(56) References Cited

OTHER PUBLICATIONS

Figure 1:
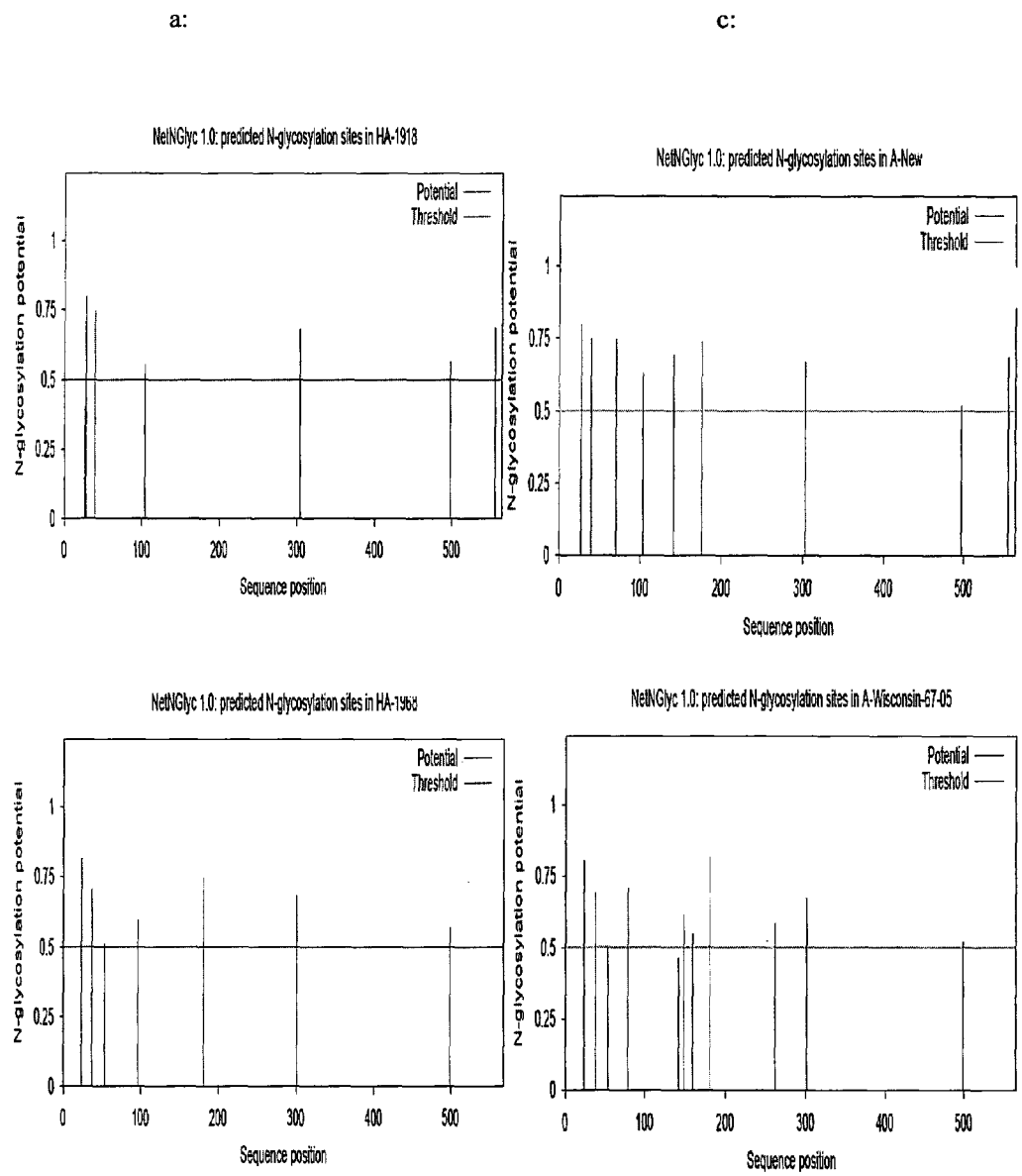

Bragstad, et al., Pandemic influenza 1918 H1N1 and 1968 H3N2 DNA vaccines induce cross-reactive immunity in ferrets against infection with viruses drifted for decades, Influenza and Other Respiratory Viruses, (1):13-23, Epub Nov. 3, 2010, (Jan. 5, 2011).
Caton et al, The Antigenic Structure of the Influenza Virus A/PR/8/34 Hemagglutinin (H1 Subtype), Cell, 31:417-427, (Dec. 1982).
Chen et al, Cross-Protection Against a Lethal Influenza Virus Infection by DNA Vaccine to Neuraminidase, Vaccine, 18(28):3214-3222, (Aug. 2000).
Corbet et al, Construction, Biological Activity, and Immunogenicity of Synthetic Envelope DNA Vaccines Based on a Primary, CCR5-Tropic, Early HIV type 1 Isolate (BX08) with Human Codons, Aids Research and Human Retroviruses, 16(18): 1997-2008, (Dec. 2000).
Davis et al, Plasmid DNA is Superior to Viral Vectors for direct Gene Transfer into Adult Mouse Skeletal Muscle, Human Gene Therapy, 4:733-740, (Dec. 1993).
Donnelly et al, Preclinical Efficacy of a Prototype DNA Vaccine: Enhanced Protection Against Antigenic Drift in Influenza Virus, Nat Med, 1(6):583-7, (Jun. 1995).
Drape, et al., Epidermal DNA vaccine for influenza is immunogenic in humans, Vaccine, 24:4475-4481, (Aug. 2006).
Epstein et al, Protection Against Multiple Influenza A Subtypes by Vaccination with Highly Conserved Nucleoprotein, Vaccine, 23:5404-5410, (Nov. 2005).
Genbank Accession # CY008158, Influenza A virus (A/Beijing/1/68(H5N2)) segment 6, complete sequence, 2006.
Gibbs, MJ, Molecular Virology: Was the 1918 Pandemic Caused by a Bird Flu? Nature, vol. 440(7088):E8; Discussion, (Apr. 27, 2006).
Hall, Thomas, BioEdit: A User-Friendly Biological Sequence Alignment Editor and Analysis Program for Windows 95/98/NT, Nucleic Acids Symposium Series, 41: 95-98, (1999).
Hoffmann et al, Role of specific hemagglutinin amino acids in the immunogenicity and protection of H5N1 influenza virus vaccines, PNAS, 102(36):12915-12920, (Sep. 6, 2005).
Johnson et al, Updating the Accounts: Global Mortality of the 1918-1920 "Spanish" Influenza Pandemic, Bull. Hist. Med., 76:105-115, (Spring 2002).
Jones, et al., DNA vaccination protects against an influenza challenge in a double-blind randomised placebo-controlled phase 1b clinical trial, Vaccine, 27(18):2506-12. Epub Feb. 24, 2009, Apr. 2009.
Kawaoka et al, Avian-to-Human Transmission of the PB1 Gene of Influenza A Viruses in the 1957 and 1968 Pandemics, Journal of Virology, 63(11):4603-4608, (Nov. 1989).
Ko et al, Optimization of codon usage enhances the immunogenicity of a DNA vaccine encoding mycobacterial antigen Ag85B, Infection and Immunity, 73(9):5666-5674, (Sep. 2005).
Kobasa et al, Enhanced Virulence of Influenza A Viruses with the Haemaglutinin of the 1918 Pandemic Virus, Nature, 431(7009):703-707, (Oct. 7, 2004).
Kodihalli et al, Cross-Protection Among Lethal H5N2 Influenza Viruses Induced by DNA Vaccine to the Hemagglutinin, Journal of Virology, 71(5):3391-3396, (May 1997).
Kodihalli et al, DNA Vaccine Encoding Hemagglutinin Provides Protective Immunity Against H5N1 Influenza Virus Infection in Mice, Journal of Virology, 73(3):2094-2098, (Mar. 1999).
Kodihalli et al, Strategies for Inducing Protection Against Avian Influenza A Virus Subtypes with DNA Vaccines, Vaccine 18(23):2592-2599, (May 2000).
Kong et al, Protective Immunity to Lethal Challenge of the 1918 Pandemic Influenza Virus by Vaccination, PNAS, 103(43): 15987-15991, (Oct. 24, 2006).
Kutzler and Weiner, DNA vaccines: ready for prime time?, Nature Reviews, Genetics, 9(10):776-788, (Oct. 2008).
Lambert and Fauci, Current Concepts influenza vaccines for the future, New England Journal of Medicine, 363(21):2036-2044, (Nov. 2010).
Lindstrom et al, Genetic Analysis of Human H2N2 and Early H3N2 Influenza Viruses, 1957-1972: Evidence for Genetic Divergence and Multiple Reassortment Events, Virology, 328(1):101-119, (Oct. 2004).
Liu et al., DNA Vaccines: Recent Developments and Future Possibilities, Human Gene Therapy, 17(11):1051-1061, (Nov. 2006).
Ljungberg et al, DNA Vaccination of Ferrets with Chimeric Influenza A Virus Hemaglutinin (H3) Genes, Vaccine, 209(16): 2045-2052, (May 2002).
Martinet et al, Protection of mice against a lethal influenza challenge by immunization with yeast-derived recombinant influenza neuraminidase, Eur. J. Biochem, 247(1):332-338, (Jul. 1997).
Reid et al, Characterization of the 1918 "Spanish" Influenza Virus Neuraminidase Gene, PNAS, 97(12):6785-6790, (Jun. 6, 2000).
Reid et al, Origin and Evolution of the 1918 "Spanish" Influenza Virus Hemagglutinin Gene, Proc. Natl. Acad. Sci. 96(4):1651-1656, (Feb. 1999).
Schulze et al, Effects of glycosylation on the properties and functions of influenza virus hemagglutinin, The Journal of Infectious Diseases, 176:S24-S28, (Aug. 1997).
Seo et al, Lethal H5N1 Influenza Viruses Escape Host Anti-Viral Cytokine Responses, Nature Medicine, 8(9): 950-954, (Sep. 2002).
Smith et al, Lessons for Human Influenza from Pathogenicity Studies with Ferrets, Reviews of Infectious Diseases, 10(1) (Jan.-Feb. 1988).
Spackman et al, Development of a Real-Time Reverse Transcriptase PCR Assay for Type A Influenza Virus and the Avian H5 and H7 Hemagglutinin Subtypes, Journal of Clinical Microbiology, 40(9):3256-3260, (Sep. 2002).
Talon et al, Activation of Interferon Regulatory Factor 3 is Inhibited by the Influenza A Virus NS1 Protein, Journal of Virology, 74(17):7989-7996, (Sep. 2000).
Tamura et al, Mechanisms of Broad Cross-Protection Provided by Influenza Virus Infection and Their Application to Vaccines, Journal Infectious Diseases, 58:195-207, (Aug. 2005).
Taubenberger et al, Characterization of the 1918 Influenza Virus Polymerase Genes, Nature, 437:889-893, (Oct. 6, 2005).
Tumpey et al, Characterization of the Reconstructed 1918 Spanish Influenza Pandemic Virus, Science, 310(5745):77-80, (Oct. 7, 2005).
Tumpey et al, Pathogenicity and Immunogenicity of Influenza Viruses with Genes from the 1918 Pandemic Virus, PNAS, 101(9):3166-3171 (Mar. 2, 2004).
Tumpey et al, Pathogenicity of Influenza Viruses with Genes form the 1918 Pandemic Virus: Functional Roes of alveolar Macrophages and Neutrophils in Limiting Virus Replication and Mortality in Mice, Journal of Virology, 79(23):14933-14944, (Dec. 2005).
Ulmer et al, Protective CD4+ and CD8+ T Cells against Influenza Virus Induced by Vaccination with Nucleoprotein DNA, Journal of Virology, 72(7):5648-5653, (Jul. 1998).
Wang et al, Hemagglutinin (HA) Proteins from H1 and H3 Serotypes of Influenza A Viruses Require Different Antigen Designs for the Induction of Optimal Protective Antibody Responses as Studied by Codon-Optimized HA DNA Vaccines, Journal of Virology, 80(23):11628-11637, (Dec. 2006).
Wang et al, Influenza A Virus NS1 Protein Prevents Activation of NF-κB and Induction of Alpha/Beta Interferon, Journal of Virology, 74(24):11566-11573, (Dec. 2000).
Wang et al, Intranasal Immunization with Liposome-Encapsulated Plasmid DNA Encoding Influenza Virus Hemagglutinin Elicits Mucosal, Cellular and Humoral Immune Responses, Journal of Clinical Virology, 31, Suppl. 1:S99-106 (Dec. 2004).
Webster et al, Protection of Ferrets against Influenza Challenge with a DNA Vaccine to the Haemagglutinin, Vaccine, 12(16):1495-1498, (Dec. 1994).
Xie, Evaluating the vaccine potential of an influenza A viral hemagglutinin and matrix double insertion DNA plasmid, Vaccine, 25(44):7649-55. Epub Sep. 2007, (Nov. 2006).
International Search Report in PCT/DK2009/000247 (International Stage of present application).
Written Opinion in PCT/DK2009/000247 (International Stage of present application).

(56) References Cited

OTHER PUBLICATIONS

Jan. 29, 2009 Office Action and Notice of References Cited in U.S. Appl. No. 12/156,456.
Response to Jan. 29, 2009 Office Action in U.S. Appl. No. 12/156,456.
Oct. 20, 2009 Office Action and Notice of References Cited in U.S. Appl. No. 12/156,456.
Dec. 28, 2010 Office Action in U.S. Appl. No. 12/689,547.
Response to Dec. 28, 2010 Office Action in U.S. Appl. No. 12/689,547.
Jun. 10, 2011 Office Action in U.S. Appl. No. 12/689,547.
Response to Jun. 10, 2011 Office Action in U.S. Appl. No. 12/689,547.
Antonovics, et al., Was the 1918 flu avian in origin?, Nature, Apr. 27, 2006, pp. E8-E10, vol. 440.
Finter, Quantitative Haemadsorption, a New Assay Technique, I. Assay of Interferon, Virology, 1964, pp. 589-597, vol. 24.
Ljungberg, et al., Enhanced immune responses after DNA vaccination with combined envelope genes from different HIV-1 subtypes, Virology, Oct. 10, 2002, pp. 44-57, vol. 302, No. 1.
Martel and Aasted, Characterization of antibodies against ferret immunoglobulins, cytokines and CD markers, Veterinary Immunology and Immunopathology, 2009, pp. 109-115.
Olsen, Review of the Use of Statistics in Infection and Immunity, Infection and Immunity, Dec. 2003, pp. 6689-6692, vol. 71, No. 12.
Schmittgen, et al., Quantitative Reverse Transcription-Polymerase Chain Reaction to Study mRNA Decay: Comparison of Endpoint and Real-Time Methods, Analytical Biochemistry, 2000, pp. 194-204, vol. 285.
Vinner, et al., Immune response in rhesus macaques after mixed modality immunisations with DNA, recombinant adenovirus and recombinant gp120 from human immunodeficiency virus type 1, APMIS, 2006, pp. 690-699, vol. 114.
World Health Organization, WHO Manual on Animal Influenza Diagnosis and Surveillance, 2002, pp. 1-99, WHO/CDS/CSR/NCS/2002/5.
Igarashi, et al., Genetically destined potentials for N-linked glycosylation of influenza virus hemagglutinin, online May 5, 2008, Virology, 376:323-329.
Jan. 11, 2012 Response to IPER of international stage in counterpart European Patent Application No. 09795684.1.
Jan. 24, 2013 Examination Report in counterpart European Patent Application No. 09795684.1.
May 23, 2013 Response to Jan. 24, 2013 Examination Report in counterpart European Patent Application No. 09795684.1.
Jul. 29, 2013 Examination Report in counterpart European Patent Application No. 09795684.1.
Dec. 9, 2013 Response to Jul. 29, 2013 Examination Report in counterpart European Patent Application No. 09795684.1.
Garten, et al., Antigenic and Genetic Characteristics of the Early Isolates of Swine-Origin 2009 A(H1N1) Influenza Viruses Circulating in Humans, Science, published online May 22, 2009, 325:197-201.
GenBankID No. ACQ76318.1 (Jun. 1, 2009), "hemagglutinin [Influenza A virus (A/California/4/2009(H1N1))]".
Holman, et al., Multi-antigen vaccines based on complex adenovirus vectors induce protective immune responses against H5N1 avian influenza viruses, Vaccine, electronically published Mar. 14, 2008, 26(21):2627-2639.
Shakin-Eshleman, et al., The amino acid at the X position of an Asn-X-Ser sequon is an important determinant of N-linked core-glycosylation efficiency, J Biol Chem., Mar. 15, 1996, 271(11):6363-6366.
Ulmer, et al., Heterologous protection against influenza by injection of DNA encoding a viral protein, Science, Mar. 19, 1993, 259(5102):1745-1749.
Jun. 5, 2014 Examination Report in counterpart European Patent Application No. 09795684.1.
NSW Health (New South Wales Ministry of Health), Factsheet: Pandemic Influenza, Sep. 10, 2006, 17(9-10):152-153.
Webster and Laver, The origin of pandemic influenza, Jan. 1972, Bull. Wld Hlth Org. (World Health Organization), 47(4): 449-452.
Webster and Campbell, Studies on the Origin of Pandemic Influenza, IV. Selection and Transmission of "New" Influenza Viruses in Vivo, Dec. 1974, Virology 62(2):404-413.
Ghendon, Introduction to Pandemic Influenza Through History, Aug. 1994, Eur. J. Epidemiol., 10(4):451-453.
Scholtissek, Introduction to Pandemic Influenza Through History, Aug. 1994, Eur. J. Epidemiol., 10(4):451-458.
World Health Organization, Influenza Virus Infections in Humans, Feb. 2014, 2 pp.

\* cited by examiner (A):

(B):

(C):

(D):

A:

B:

Figure 8

Virus titre in nasal wash post challenge

OPTIMIZED INFLUENZA VACCINES

CROSS-REFERENCE TO RELATED APPLICATIONS

This application is a national stage of International Patent Application No. PCT/DK2009/000247, filed Nov. 27, 2009.

FIELD OF INVENTION

The invention concerns protein and nucleotides vaccines encoding influenza A proteins with few or no glycosylation sites. The DNA or RNA encodes for haemagglutinin and/or neuraminidase and/or Matrix and/or Nucleoprotein where the origin of the DNA or RNA can be both pandemic influenza strains, which codes for proteins which have a naturally low content of glycosylation sites and DNA or RNA from non-pandemic influenza strains where the nucleotides have been mutated or changed so it encodes for proteins with less glycosylation sites than the seasonal strain. The invention also discloses immunogenic compositions and the use of the haemagglutinin (HA) encoding DNA and/or neuraminidase (NA) encoding DNA expressing the novel 2009 pandemic H1N1v influenza A as a vaccine component optionally combined with DNA encoding the matrix protein (M) and DNA encoding the nucleoprotein (NP) from the 1918 pandemic H1N1 strain and DNA encoding the HA and NA from a recent seasonal H3N2 strain for a combined vaccine against present and future H1N1 and H3N2 infections in humans and swine.

GENERAL BACKGROUND

Influenza is one of the oldest and most common diseases known to man causing between three and five million cases of severe illness and between 250,000 and 500,000 deaths every year around the world. Also swine are susceptible to human and avian influenza virus since they posses both receptors in their respiratory tract. Thus, swine get infection and pneumoni from human influenza strains and may serve as a dangerous mixing vessel for generation of new recombinant influenza strains with pandemic potential.

Influenza rapidly spreads in seasonal epidemics affecting 5-15% of the population and the burden on health care costs and lost productivity are extensive (WHO). Influenza like illness was first described by Hippocrates in the year 412 BC. Up to the 19th century influenza was thought to be a bacterial infection. Virus as the causative agent was first determined in 1931 by Richard Shope. The first known influenza A pandemic was in 1580 and since then there has been 31 pandemics of which three appeared in the 20th century namely the 'Spanish flu' in 1918, the 'Asian flu' in 1957 and the 'Hong Kong flu' in 1968, respectively. The pandemic of 1918 influenza A H1N1 was the worst pandemic in newer times causing 20 to 50 million deaths worldwide. The most common form of influenza is seasonal outbreaks and epidemics of variable severity.

Zoonosis of avian influenza virus (AIV) able to infect humans and swine and the spread in Asia, parts of Europe and the Middle East has recently evoked the concern about a pandemic occurring also in the $21^{st}$ century. The causative strain of the pandemic will probably be unknown until the pandemic emerges and there will be an urgent need for a vaccine. Therefore fast diagnosis and characterisation of circulating strains as well as emerging strains, new alternative vaccines approaches and production ways will be required in order to minimise the severity of the pandemic.

Since seasonal influenza A vaccines are also produced on eggs an epidemic of highly pathogenic AIV among poultry will also influence the production of seasonal vaccines. Moreover the traditional influenza protein vaccines only have a limited protective effect. Also seasonal vaccines has to be changed every season because of the genetic drift of influenza A virus and the narrow type specific antibody induction by traditional influenza A protein vaccines. Therefore there is a need for new alternative influenza A vaccines with different properties The influenza virus belongs to the Orthomyxoviridae family. The family includes three genera; influenza A, B and C viruses, identified by antigenic differences in their nucleoprotein (NP) and matrix protein (M). The influenza A genus is further divided into subtype combinations based on the antigenic differences of the surface glycoproteins haemagglutinin (HA) and neuraminidase (NA). The A strain have evolved to be able to infect several other mammalian species (e.g. horses and swine). Influenza A viruses of all recognised 16 HAs and 9 NAs antigenic subtypes have been recovered from aquatic birds but few infect other animal species indicating that aquatic birds are the natural reservoirs of influenza A.

The influenza A viruses have been the causative agents for the major pandemics and most of the annual outbreaks of epidemic influenza. This invention solely focuses on the influenza A genus. The current nomenclature system for human influenza viruses includes the geographical location of first isolation, strain number, and year of isolation. The antigenic description of HA and NA is given in brackets, e.g. A/Moscow/10/99(H3N2). Nonhuman strains also include the host of origin in the nomenclature, e.g. A/mallard/Denmark/64650/03(H5N7).

The influenza A virus genome consist of eight negative sense single stranded (ss) ribonucleic acid (RNA) segments packed in the viral core comprised of host cell membrane and a matrix 1 (M1) protein layer. The eight segments are associated with nucleoprotein (NP) and three large proteins; polymerase basic 1 (PB1) and 2 (PB2) protein, and polymerase acidic (PA) protein, which are responsible for RNA replication and transcription. NP encapsulates the RNA and forms ribonucleoprotein (RNP) complexes that protect and stabilise the RNA. Each segment include a sequence of 11-13 nucleotides at the 5' ends and 9-12 nucleotides at the 3' ends which are highly conserved and similar for A, B and C viruses. The major glycoproteins HA and NA, and the ionchannel M2 protein, are embedded in a host derived lipid bilayer. Influenza viruses are somewhat pleomorphic in shape, but mostly spherical (80-120 nm in diameter).

All subtypes of influenza A are perpetuated in the wild aquatic bird population, believed to be the natural reservoir of influenza. Under normal circumstances an influenza infection in wild ducks is asymptomatic. The virus replicates in the intestinal tract and is excreted in high concentrations with the faeces for a period up to 30 days. An avian influenza virus can persist in water and retain infectivity for about 100 days at 17° C. and can be stored indefinitely at −50° C. The continuous circulation of influenza A viruses might be due to bird overwintering sites in the subtropics. The 2004 H5N1 strains have become very stable and can survive for 6 days at 37° C. The virus is killed by heat at 56° C. for 3 hours or 60° C. for 30 minutes. Also disinfectants like formalin and iodine compounds efficiently kill the influenza virus. Avian influenza viruses have been believed to be in evolutionary stasis in its natural host, the virus and the host tolerate each other. Generally no severe clinical symptoms are seen when poultry are infected with avian influenza, and the virus is described as a low pathogenic avian influenza virus (LP AIV). The subtypes H5 and H7 have the potential to become highly pathogenic (HP) to chickens through accumulation of mutations after transmission to poultry. Contrary to previous belief, wild migratory birds might play some role in the transmission of HP AIV. Thousands of wild aquatic birds in Hong Kong 2002 and China 2005 became infected with HP AIV H5N1 and this contributed to the spread of HP H5N1 to Europe and Africa in 2005.

Seasonal influenza strains have been isolated from humans and swine all year round, but in temperate climates it is a winter disease probably because people come together and stay in less ventilated rooms due to the cold weather.

Of the 16 recognised subtypes of HA and 9 NAs only H1, H2, H3, N1 and N2 have circulated in humans and swine in the last century. The pandemic introduction in humans of these types were 1918 H1N1, 1957 H2N2 ("Asiatic flu"), 1968 H3N2 ("HongKong Flu") and non-pandemic introduction of the reassorted new type H1N2 in 2001, respectively. The antigenicity of human influenza viruses are constantly changing by accumulation of mutations in the HA and NA antigenic sites, thereby making the virus capable of evading the host immune system causing epidemics. Viral mutagenesis is enhanced by the lack of "proof reading" in the replication of RNA. The mutation frequency is approximately one in 100,000 nucleotides. At the northern hemisphere seasonal influenza outbreaks usually occur between October and April and from April to October in the southern hemisphere. The antigenic drift of human influenza viruses are closely monitored by the World Health Organization's global influenza surveillance program. The components of the next seasons influenza vaccine for the northern hemisphere is determined in February based on the knowledge about the current circulating strains, and re-evaluated in September for the southern hemisphere.

Antigenic shift can occur in three ways. Either by direct transmission of an avian strain adapted to humans, genetic reassortment or reintroduction of an "old" strain. The possibility of an avian influenza virus crossing the species barrier and infecting humans directly was not recognised before 1997 when 18 people in Hong Kong became ill with HP AIV H5N1.

The origin of the 1918 pandemic is controversial. Taubenberger et at., (*Characterization of the 1918 influenza virus polymerase genes. Nature,* 2005, 437:889-893) suggested based on phylogenetics of the polymerase genes that the virus was entirely of avian origin. However, there are large disagreements about the actual origin of the virus and many still believe that also this pandemic strain is a reassortant between a mammalian and avian virus most likely occurring from swine. If the virus was of avian origin it might imply that the HP avian viruses circulating currently could cause a new pandemic by direct transmission to humans. Antigenic reassortment occurs when viral segments from two antigenic different viruses infecting the same cell. The reassorted virus contains segments of both strains and if the newly introduced segment is HA (and NA) the complete antigenicity of the virus might change and the virus escapes the host immunity. These reassortants might be catastrophic if the virus is capable of efficient replication in the new host. In worst case such a reassorted strain might lead to pandemics, world-spanning infections to which we have no pre-existing immunity. The pandemics of 1957 and 1968 were reassortants that acquired the HA, NA and PB1 and HA and PB1 genes from an aquatic source, respectively. In 1977 a strain identical to the H1N1 strains that circulated before 1957 re-emerged. Pigs are possible "mixing vessels" for reassorted viruses due to their receptor tropism for both α-(2,3) and α-(2,6) linkage to galactose. Other species like chicken and man might also serve as mixing vessels in the light of direct crossover to humans from an avian source after the discovery of α-(2,3) avian like receptor on cells also in humans and chickens.

The interpandemic evolution of influenza viruses has been thought to be caused by progressive antigenic drift due to the mutability of the RNA genome. H3N2 has been the predominant subtype circulating in humans since 1968 and has been in rapid drift as a single lineage while there has been slow replacement of antigenic variants of the H1N1 viruses. It has been shown that the rate of accumulating mutations is approximately $4-5 \times 10^{-3}$ substitutions per nucleotide per year for HA1 others predict a rate of $5.7 \times 10^{-3}$ substitutions per nucleotide per year. The HA and NA might evolve independently from each other and reassortments of the internal genes are also known. Positive selection has been inferred on codons involved at antibody antigenic sites, T-cell epitopes and sites important virus egg growth properties. Recent research on viruses has suggested that the evolution of influenza do not always follow a constant rate, but is characterised by stochastic processes, short intervals of rapid evolution, long intervals of neutral sequence evolution and slow extinction of coexisting virus lineages. The evolution seems also more influenced by reassortment events between co-circulating lineage and viral migration than previously believed.

Vaccination is the preferred choice for influenza prophylaxis. Inactivated influenza vaccines are licensed worldwide while cold-adapted live vaccines are licensed only in Russia and the USA. The preferred prophylaxis of annual influenza infections is vaccination with inactivated protein vaccines from virus propagated in hens' eggs. Thus, the common vaccines are the inactivated vaccine viruses which are propagated in hens' eggs and inactivated by formaldehyde or β-propiolactone. There are three classes of inactivated vaccines; whole, split (chemically disrupted with ether or tributyl phosphate) and subunit (purified surface glycoproteins) administrated intramuscularly or subcutaneously. Whole inactivated influenza vaccine is not currently used due to high levels of side effects. The seasonal influenza vaccine (split and subunit) is trivalent, comprising H3N2 and H1N1 influenza A virus strains and an influenza B virus. The normal human vaccine dose is standardised to 15 μg HA protein of each virus component administrated once in normal healthy adults and twice in children and other persons with no pre-existing influenza A immunity. The conventional vaccines induce merely a humoral immune response. The protective effect of the traditional protein split vaccine is very limited and because of the continuous evolution of influenza A virus strains and the typespecific antibodies induced by the conventional vaccines a new vaccine has to be produced every year based on the most recent circulating influenza A strain. Several vaccine improvements are necessary in case of a new emerging human strain. Egg production is too slow (6-12 months) in the case of emerging strains. If this strain is also an AIV virus highly pathogenic (HP) for poultry, egg production might be impossible because the virus kills the egg embryo. Also the availability of eggs might be limited slowdown the vaccine production. In the case of no pre-existing immunity in the population two vaccinations would be necessary, thereby further delaying the vaccine production. Even if there are no new pandemic influenza A among humans but only spread of a HPV AIV among poultry the shortage of eggs will limit production on eggs of traditional seasonal influenza vaccines. In addition, traditional influenza protein vaccines do not have optimal protection as prophylaxis and no therapeutic effect. Thus, there is a need for new alternative influenza vaccines.

Although DNA vaccines were developed more than 16 yeas ago, clinical trials preceding stage I and II in humans are rare. Two veterinary DNA vaccines however, have been licensed; one for West Nile Virus (in horse) and a second for Infectious Hematopoetic Necrosis virus in Salmon. This demonstrates that DNA vaccines can have good protective effects and that new DNA vaccines are not limited by the size of the animal or species. The great success with DNA vaccines observed for the murine model for first generation DNA vaccines did not translate well to humans, nonetheless; researchers have recently demonstrated protective antibodies levels by a single dose of gene gun administrated HA DNA vaccine to humans.

"Nucleic acid immunization" or the commonly preferred name "DNA vaccines" are the inoculation of antigen encoding DNA or RNA as expression cassettes or expression vectors or incorporated into viral vectors with the purpose of inducing immunity to the gene product. Thus, in our definition of DNA vaccines we include all kinds of delivery systems for the antigen encoding DNA or RNA. The vaccine gene can be in form of circular plasmid or a linear expression cassette with just the key features necessary for expression (promotor, the vaccine gene and polyadenylation signal). Delivery systems may most often be naked DNA in buffer with or without adjuvant, DNA coupled to nanoparticles and/or formulated into adjuvant containing compounds or inserted into live viral or bacterial vectors such as Adenovirus, adenoassociated virus, alphavirus, poxviruses, herpes virus etc. DNA vaccines hold great promise since they evoke both humoral and cell-mediated immunity, without the same dangers associated with live virus vaccines. In contrast to live attenuated virus vaccines DNA vaccines may be delivered to same or different tissue or cells than the live virus that has to bind to specific receptors. The production of antigens in their native forms improves the presentation of the antigens to the host immune system. Unlike live attenuated vaccines, DNA vaccines are not infectious and can not revert to virulence. DNA vaccines expressing HA, NA, M, NP proteins or combinations of these have proven to induce immune responses comparable to that of a natural viral infection.

DNA vaccines offer many advantages over conventional vaccines. It can be produced in high amounts in short time, abolishing the need for propagation in eggs, it is cost-effective, reproducible and the final product does not require cold storage conditions, because DNA is stable and resistant to the extremes of temperature. All currently licensed inactivated vaccines are efficient at inducing humoral antibody responses but only live attenuated virus vaccines efficiently induce a cytotoxic cellular response as well.

DNA vaccines induce an immune response which is comparable to the response acquired by natural virus infection by activating both humoral and cell-mediated immunity (6,30). The broad response to DNA vaccines is a result of the encoded genes being expressed by the transfected host cell, inducing both a Th1 and Th2 immune responses. The production of antigens in their native form improves the presentation of the antigens to the host immune system. In contrast, the conventional inactivated influenza protein based vaccines only induce a humoral response (Th2), directed against the influenza surface glycoproteins. This type of response is ineffective against drifted virus variants and therefore the virus composition of the seasonal influenza vaccine has to be assessed every season. Antigenic cross-reactive responses are mainly induced by the more conserved influenza proteins like the nucleoprotein (NP) and the matrix (M) protein. By including these genes in a DNA vaccine higher cross reactivity between drifted and heterologous strains have been shown (4, 7, 8, 13).

Influenza infection and symptoms in ferrets are highly comparable to what is observed in humans and is therefore one of the best models for influenza vaccination trials (22). Influenza HA DNA vaccines in ferrets have also previously proved effective (18,32).

It has previously been shown that 1918 H1N1 whole inactivated virus vaccine induced partly protection against infection with 1918 H1N1 in mice (28), also recently DNA vaccines encoding the HA from 1918 showed complete protection of mice against a 1918 H1N1 challenge (16) but no protection against present day influenza was demonstrated.

We have demonstrated that gene gun administrated codon optimised plasmid DNA vaccine encoding HA and NA with or without M and NP based on the H1N1 pandemic virus from 1918 induce protection in ferrets against infection with a present day H1N1 virus (Bragstad et al 2009 and PCT/DK2008/000201). This demonstrates a vaccine induced protection not mediated by the usual anti-HA and anti-NA antibodies but by a different immunological mechanism most likely involving cellular immunity. Since the internal proteins M and NP encoded by the DNA and/or the influenza A virus are more conserved among different H1N1 strains than HA and NA it can be expected that the induced immunity to NP and M DNA vaccines are more broadly protective which could extend to also new H1N1 strains. The viruses are separated by a time interval of 89 years and differ by 21.2% in the HA1 protein. These results suggest not only a unique ability of the DNA vaccines but also a unique and unexpected feature of the 1918 HA and/or NA in inducing especially broad and efficient protective immunity against even extremely drifted strain variants. The present invention discloses that an induced immune response with a DNA vaccine encoding HA and/or NA of the 1918 H1N1 influenza A gives a high level of cross protection against present day influenza infection.

DNA vaccines do have the ability of immune stimulatory mechanisms. This might be one reason why we observe such a good induced cross reactivity and protection against challenge infection. Cross-protection and cross-reactivity induced by DNA vaccines of strains differing by 11-13% in HA1 has been demonstrated by others (13-15) but not as high as with the 21.2% divergence we observe.

Influenza vaccines that have the ability to induce immune responses able to cross-react with drifted virus variants and even heterologous strains would be of great advantage for both annual vaccine development and in case of emerging new strains.

Since the novel influenza A (H1N1v) is notably different from other human H1N1 viruses it is assumed that present H1N1 virus immunity and seasonal H1N1 vaccines will not induce efficient protection against the novel strain. The novel H1N1v virus is approximately 5% different in the nucleotide sequence from other known swine H1N2 viruses, while it is nearly 24% different from last seasons circulating human H1N1 viruses.

Thus, in the current situation with a new pandemic H1N1v virus and future variants here off we believe the best vaccine for the current circulating viruses and near future viruses will be a DNA vaccine comprising the HA and NA genes of the new pandemic H1N1v virus, the internal genes of the previous pandemic H1N1 virus from 1918 and the HA and NA genes of the circulating seasonal H3N2 virus. The genes of the H1N1v strain will be included to induce perfect protection against the circulating H1N1v and for future variants of this strain. We expect this strain with variants hereof to be the next seasonal H1N1 viruses in humans. The NP and M internal genes of the 1918 H1N1 pandemic is included as these are the ancestors of all other NP and M genes in human influenza viruses. These highly conserved genes are expected to induce better cross-protection. The HA and NA genes of the seasonal H3N2 virus are included as these will give the best protection against currently circulating H3N2 viruses and future H3N2 viruses. We believe that these gene combinations in a DNA vaccine will be the optimal more universal influenza vaccine at present time and for the nearest future.

We have surprisingly shown that a mix of DNA plasmids of both "initial" pandemic genes with few or no glycosylation sites and optionally present time genes induces the ultimate protection in the sense that the more antigenic sites will be exposed to the host immune system for antibody recognition. Alternatively influenza genes where all or some of the glycosylation codons have been changed/removed so the protein expressed has less or no glycosylation sites can be used in a mixture either themselves or with pandemic influenza DNA to make up a universal influenza vaccine.

SUMMARY OF THE INVENTION

The pandemic influenza A strains were the first introductions of H3N2 and H1N1 subtypes in humans. Since these first introductions the viruses have drifted, accumulating mutations at antigenic sites, but also the N-glycosylation pattern has changed during the drifted years. Accumulating N-linked glycosylation sequons help mask the antigenic sites for recognition by the host immune system. The "naked" initial haemagglutinins, e.g. haemagglutinins with few or no glycosylation, induce a broad cross reactivity against widely drifted influenza subtypes. Our preliminary results show that the 1918 H1N1 DNA vaccines are as good as or better candidates for influenza prophylaxis than annual conventional protein based vaccines in ferrets. The DNA vaccine immune response raised against these "initial" immunogens can cross react with present day viruses, while the opposite may not be true. Also present day influenza DNA used as vaccine show better influenza prophylaxis than annual conventional protein based vaccines against present day viruses. The influenza virus escapes the host immune system by accumulation of mutations especially at the surface glycoproteins HA and NA. Some of these mutations generate additional glycosylation sites which may camouflage the antigenic sites in the gycoproteins and the virus can thereby escape the host immunesystem. The initial pandemic strains possessed a low number of glycosylation sites while the present day viruses have accumulated sites during virus drift. Since the pandemic in 1918 with the H1N1 virus, three additional glycosylation sites have accumulated in the 1999 H1N1 virus included in our experiments, adding the total number of predicted N-glycosylation sites to seven. The current novel pandemic H1N1v virus also only possesses the basic four glycosylation sites as the pandemic 1918 virus.

The present invention discloses that an induced immune response with a DNA vaccine encoding HA and/or NA of the H1N1v influenza A alone or in combination with DNA vaccine encoding NP and M of H1N1 1918 virus gives a high level of cross protection against the novel H1N1v as well as future variants of this H1N1v as well as protection against present day and future H1N1 influenza A virus infections in humans and swine. In combination with DNA vaccine encoding HA and/or NA from an H3N2 strain preferentially from a recent (2005-2008) strain, the DNA vaccine will act as an universal influenza DNA vaccine inducing protective immunity against future circulating H1N1 and H3N2 viruses. The DNA vaccine can be used for humans and animals e.g. pigs to prevent/limit infection and/or spread of infection of human and pig influenza strains.

DETAILED DISCLOSURE OF THE INVENTION

The present invention discloses the use of nucleotides encoding influenza proteins with few or no glycosylation sites for manufacturing an immunogenic composition or a vaccine component against present day and coming influenza A infections in humans and pigs, where the nucleotides encodes for haemagglutinin (HA) and/or Neuraminidase (NA) and/or matrix protein (M) and/or the nucleoprotein (NP). The nucleotides can be a mix of pandemic DNA or RNA with non-pandemic DNA or RNA.

In a preferred embodiment of the invention the DNA or RNA encodes for 2009 H1N1v HA and NA, 1918 H1N1 M and NP together with seasonal H3N2 HA and NA.

In a preferred embodiment of the invention the DNA or RNA codons are optimized ("humanized") e.g. the DNA sequence for haemagglutinin and neuraminidase and matrix and nucleoprotein is changed so the sequence coding for said proteins is changed to be optimally expressed in mammalian cells.

In another embodiment the non-pandemic DNA or RNA is mutated so codons are changed so the sequence codes for proteins with less glycosylation sites than the seasonal strain. Preferably some or all the codons coding for Asn-X-Ser of Asn-X-Thr, where X could be any amino acid except proline are changed.

The present invention also discloses the use of nucleotides encoding the haemagglutinin (HA) from pandemic influenza strain(s) (e.g. the 2009 H1N1v, the 1918 H1N1 and/or 1957 H2N2 and/or 1968 H3N2 influenza A virus) as a vaccine component against present day and coming/future H1, H2, H3, N1, N2 containing influenza A infections in humans and swine.

Haemagglutinin and/or neuraminidase and/or matrix protein and/or the nucleoprotein from pandemic influenza virus can optionally be included as proteins and/or DNA vaccines.

In another embodiment the vaccine comprises a mix of influenza proteins or codon optimized DNA encoding the proteins HA and NA from the pandemic 2009 H1N1v and/or Matrix protein and Nucleoprotein from 1918 H1N1 and/or HA and NA from a recent H3N2 2005 virus) as a vaccine component against present day and coming/future H1, H3, N1, N2 containing influenza A infections in humans and swine.

The vaccine is administered by injection of naked DNA and/or RNA with or without electroporation or inoculated by gene gun. Alternatively the vaccine genes is administrated incorporated into apoptotic cell bodies, or in a live virus such as Adenovirus, poxvirus, adenoassociated virus, alphavirus, herpes virus and/or bacteria such as *shigella* species or *salmonella* species or *lactobacillus* species or *lactococcus* species. Another way of administration is by saline or buffer injection of naked DNA and/or RNA in a lipid-based formulation with or without an adjuvant for mucosal delivery in the respiratory tract such as intra nasal and/or intratracheal.

Above mentioned vaccine can further comprise above mentioned haemagglutinin (HA) and/or Neuraminidase (NA) and/or matrix protein (M) and/or the nucleoprotein (NP) chosen from SEQ ID NO 2, 4, 6, 8, 10, 12, 14 and 16 or said proteins alone.

In another embodiment the vaccine comprises a sequential vaccination with pandemic DNA/RNA or protein followed by vaccination with non-pandemic DNA/RNA or protein (prime boost).

In another embodiment the vaccine comprises HA with/or without NA from the new circulating 2001 H5N7 low pathogenic (LP) avian influenza virus (AIV) strain (A/Mallard/Denmark/64650/03(H5N7)) as DNA vaccines and/or proteins. The vaccine is intended to protect birds and humans and swine against H5 influenza A strains.

In another embodiment the vaccine comprises HA with or without NA and/or M and/or NP from the newly introduced and circulating March 2006 Denmark H5N1 high pathogenic avian influenza A virus (AIV) strain (A/buzzard/Denmark/6370/06(H5N1)) as DNA vaccines and/or proteins. The vaccine is intended to broadly protect birds and humans and swine against any H5 containing influenza A strains.

The present invention discloses the use of codon optimised pandemic genes in transcriptionally active PCR for generation of transcriptionally active genes for direct use as DNA vaccines. By this the plasmid backbone is not used. The PCR products will contain all components for efficient expression of genes in eukaryotic cells.

Above mentioned vaccines can be used both prophylactic and therapeutic.

Definitions

Pandemic Influenza:

A pandemic virus is a virus which is new in the sense that there is no or little pre-existing immunity against the virus in the human population and therefore the virus will spread to all parts of the world.

Glycosylation:

N-linked glycosylation is a eukaryotic co-translational and posttranslational addition of saccharides to the amide nitrogen of asparagine side chains. A modification step in the synthesis of glycoproteins. These glycosylations are essential for correct folding and stability of the glycoprotein. Glycosylations in, or close to, the antigenic binding sites might interfere with the host cell recognition of the protein. Thereby glycosylations might help mask the protein from the host immune system.

Glycosylation Sites:

Glycosylation sites are here defined as glycosylations exposed on the surface part of the protein. For membrane bound proteins like HA and NA a part of the protein is exposed on the outside of the virus and glycosylation on this part of the protein is important to the virulens of the virus and/or to exposure of immunogenic/antigenic sites. For 1918 H1N1 and the 2009 H1N1v the glycosylation sites are 4 whereas the seasonal H1N1 has 6 glycosylation sites now but may accumulate more in time to come. Similarly For the 1968 H3N2 the glycosylation sites are 6 whereas the seasonal H3N2 has 8 glycosylation sites. Few glycosylation sites must be the basis for the correct folding of the protein and must be present and is always found even in unadapted pandemic strains. These glycosylations sites are conserved. In time the virus protein accumulates more glycosylation sites exposed on the surface to "mask" the immunity and thereby making it more adapted and probably less virulent.

Mutated DNA:

Site directed mutagene on the influenza surface glycoproteins will alter the glycosylation pattern. Nucleotides at sequon sites can be mutated to alter the codons in the tripeptide for the glycosylation site. Thereby selected sequeons can be erased.

Alternatively the protein that should be stripped for glycosylation can be produced in an non-eukaryotic host. Also such unclycosylated vaccine protein may be delivered from such an non-eukaryotic host such as a bacteria such as *lactococcus* bacteria by delivering the transfected bacteria directly on mucosal surfaces e.g. the nose or per orally to the gut where the organism will produce the vaccine protein in situ.

Haemagglutinin:

The name haemagglutinin is derived from the viruses' ability to agglutinate red blood cells. The envelope glycoprotein HA is a rod-like shaped trimer of identical monomers. The HA protein is synthesised in the infected cell as a single polypeptide chain, HA0. This initial molecule has to be cleaved by the host cell proteases into disulfidelinked HA1 (47 kDa) and HA2 (29 kDa) subunits in order for the virus to mediate membrane fusion and subsequent infection. The HA1 subunit is the globular domain of the HA molecule which comprise the receptor binding site, responsible for virus attachment to sialic acid receptors on the host cell. The five antigenic sites A, B, C, D and E at the globular head direct the host antibody response. The HA is the primary viral antigen and the only antigen inducing a virus neutralising response in the host. The HA main functions are virion to host cell membrane fusion and fusion of the endocytosed virion with the endosomal membrane allowing release of the genome into the cytoplasm. HA is a prototype 1 integral membrane protein that is targeted to the ER membrane through an N-terminal signal peptide sequence and cleaved by signal peptidase. The HA2 subunit forms the stem of the molecule. The N-terminus of HA2 (fusion peptide) is hydrophobic and is highly conserved in the HAs of different influenza virus strains, and it is essential in HA fusion activity. The HA is posttranslationally modified by addition of N-linked carbohydrates at asparagine residues (N) on each monomer and palmitic acid to cysteine (C) residues in the cytoplasmic tail region. HA binds to 5-N-acetyl neuramic acid (sialic acid) on the host cell surface and positions and are essential in determining preferred host cell tropism. Human infectious strains preferentially bind to sialic acid with $\alpha$-(2,6) linkage to galactose, while avian influenza viruses (AIV) preferentially bind to $\alpha$-(2,3)

Neuraminidase:

The neuraminidase (NA) is a class II membrane envelope glycoprotein with enzymatic activity. It is a tetramer of identical monomers forming a mushroom-like shape. The hydrophobic stalk region is membrane anchored and the globular head contains the enzyme active site and the three antigenic sites A, B and C of the molecule. Main function is to catalyse the cleavage of glycosidic linkages adjacent to sialic acid. The activity is essential for the progeny virion for efficient release from the surface of the infected cell. Like HA, NA is posttranslational modified with N-linked glycosylations. The NA molecule is target for antiviral drugs like zanamivir and oseltamivir. Inhibition of NA prevents virus release from the infected cell and delays virus propagation. Currently nine subtypes of NA have been recognised.

Matrix Proteins:

The matrix proteins consist of two proteins, the ion channel protein M2 and the structural protein M1. The M1 protein is a matrix protein lining the interior side of the membrane derived from the infected host cell giving structure and rigidity to the membrane. The M1 protein contains a hydrophobic lipid binding domain and a RNP binding domain. Assembly of negative stranded RNA viruses requires localisation of M1 proteins to the plasma membrane. The M1 proteins bind to the cytoplasmic tails of HA, NA and M2, especially NA stimulate the membrane binding by the M1 proteins. M1 together with NS2 is required for export of genomic RNPs from the nucleus, M1 also inhibits RNA synthesis. The M2 protein is a small homotetramer integral membrane protein, and ion channel, translated from a spliced mRNA in +1 reading frame. The ion channel is activated by the low pH of the endosome allowing protons to enter the interior of the virus leading to conformational changes in M1, disrupting the M1-RNP interactions. The M2 ion channel is target for antiviral drugs like amantadine and rimantadine.

Nucleoprotein

The Nucleoprotein (NP) is highly basic and binds the sugar-phosphate backbone of viral RNA in a non-sequence specific manner approximately every 25 nucleotides. NP interacts with both PB1 and PB2 and with a variety of other viral and cellular proteins. The interaction with M1 controls the transcriptional activity of RNPs and their intracellular trafficking. NP is mainly responsible for maintaining the structure of RNPs and in regulation of genome transcription and replication, the polymerase can not use naked viral RNA as template. NP associated with viral RNA is abundant in extracellular fluid and lung tissue during severe influenza A infection.

The 1918 Influenza Virus:

The most severe pandemic this century has been the 1918 H1N1 "Spanish flu". The virus killed between 40 and 50 million people worldwide during 1918 and 1919 (10). Based on preserved specimens all genes have been genetically characterised and the entire virus has now been restored (27). This gives a unique opportunity to elucidate the mechanisms of immunopathogenesis of the pandemic strain. The origin of the 1918 pandemic is debated. Taubenberger et at. 2005 suggested based on phylogenetic analysis of the polymerase genes that the virus was entirely of avian origin. However, there are large disagreements about the actual origin of the virus and many still believe that this pandemic strain also was a reassortant between a mammalian and avian virus (Taubenberger et at. 2005, Antonovics et al 2006). The haemagglutinin (HA) and neuraminidase (NA) genes of the 1918 H1N1 strain did not possess known genetic indicators for high virulence that could have explained the severe disease observed in humans (Reid et al 1999 & 2000). However, the HA (and NA) protein on a backbone of recent human viruses conferred enhanced pathogenicity in mice (Kobasa et al 2004, Tumpey et al 2005b). It might have been the combination of genes more than the HA itself that caused the lethal phenotype (Tumpey et al 2005). The uncertainty about the origin and the mechanisms of high virulence of the 1918 H1N1 virus has raised questions if it is possible to develop protective immunity to this virus. Recently it has been published that a DNA vaccine encoding the HA of the 1918 H1N1 strain showed protection to a lethal challenge of the recombinant 1918 H1N1 virus strain in mice (Kong W et al 2006). The NP and M genes of the 1918 pandemic is the ancestor of NP and M genes of both H1N1, H3N2 and H2N2 viruses circulating today. These genes are also highly conserved and change less than the surface glycoproteins through time.

The 2009 Influenza A H1N1v Virus:

During April 2009 a novel influenza H1N1v virus was discovered in California and also recognised to have caused previous outbreaks in Mexico the same year. The virus was unrelated to previous human influenza viruses both genetically and antigenically. The novel H1N1v strain is more closely related to triple reassorted swine viruses. WHO announced in June that the H1N1v virus was a pandemic virus and as of November 2009, 206 countries and overseas territories or communities have reported laboratory confirmed cases of pandemic influenza H1N1v including over 6770 deaths. Protein influenza vaccines are now available against the new pandemic strain, however these vaccines need to be evaluated as the virus changes. We aim to generate a universal DNA vaccine that will protect even against widely drifted H1n1v viruses.

Seasonal H3N2 Viruses

The first introduction of H3N2 viruses in humans occurred by the pandemic in 1968. This virus was a reassortant between avian H3 viruses and the H2N2 viruses from the 1957 pandemic. Since then, H3N2, and later, H1N1, have co-circulated in the human population causing seasonal outbreaks, and epidemics. The H3N2 viruses have changed enough during time for the protein vaccine composition to change, The pandemic strains of 1957 (H2N2) and 1968 (H3N2) were both a result of genetic reassortment with avian viruses (11,17). The origin of the 1918 pandemic is debated. Taubenberger et at., (26) suggested based on phylogenetic analysis of the polymerase genes that the virus was entirely of avian origin. However, there are large disagreements about the actual origin of the virus and many still believe that this pandemic strain also was a reassortant between a mammalian and avian virus (1,26). The haemagglutinin (HA) and neuraminidase (NA) genes of the 1918 H1N1 strain did not possess known genetic indicators for high virulence that could have explained the severity observed in humans (19,20). However, the HA (and NA) protein on a backbone of recent human viruses conferred enhanced pathogenicity in mice (12,29). It might have been the combination of genes more than the HA itself that caused the lethal phenotype (27). The uncertainty about the origin and the mechanisms of high virulence of the 1918 H1N1 virus has raised questions if it is possible to develop protective immunity to this virus. Recently it has been published that a DNA vaccine encoding the HA of the 1918 H1N1 strain showed protection to a lethal challenge of the recombinant 1918 H1N1 virus strain in mice (Kong W, Hood C, Yang Z, Wei C, Xu L, Garcia-Sastre A, Tumpey T M, Nabel G J. Protective immunity to lethal challenge of the 1918 pandemic influenza virus by vaccination. PNAS 103(43):15987-91, 2006)

DNA or RNA Vaccines:

In the following the term "DNA vaccines" refers to nucleotide vaccines meaning both DNA vaccines and RNA vaccines. The DNA vaccine can be delivered as RNA or DNA either as "naked" DNA plasmid with or without a lipid-based compound or apoptotic cells to facilitate cellular uptake, provide depot-effect and/or adjuvant effect, including or not a protein adjuvant molecule and/or DNA plasmids encoding such adjuvant protein(s), for enhanced and optimal immune induction. The DNA vaccine genes can be injected with or without a facilitators such as electroporation or delivered by jet air or coated onto particles as with a gene gun or it can be delivered to mucosal surfaces e.g. intranasally and/or intratracheally. The DNA vaccine genes can also be incorporated into a viral or bacterial vector for delivery such as Adenoviruses, poxvirus, adenoassociated virus, alphavirus, cytomegalovirus, and/or bacteria such as *lactococcus* or *lactobacillus* or shigelle or *salmonella* species.

The two most common types of DNA vaccine administration are saline injection of naked DNA and gene gun DNA inoculations (DNA coated on solid gold beads administrated with helium pressure). A saline intra muscular injection of DNA preferentially generates a Th1 IgG2a response while gene gun delivery tends to initiate a more Th2 IgG1 response. Intramuscular injected plasmids are at risk of being degraded by extracellular deoxyribonucleases, however, the responses induced are often more long-lived than those induced by the gene gun method. Vaccination by gene gun delivery of DNA, to the epidermis, has proven to be the most effective method of immunization, probably because the skin contains all the necessary cells types, including professional antigen presenting cells (APC), for eliciting both humoral and cytotoxic cellular immune responses (Langerhans and dendritic cells). Complete protection from a lethal dose of influenza virus has been obtained with as little as 1 µg DNA in mice. The standard DNA vaccine vector consists of the gene of interest cloned into a bacterial plasmid engineered for optimal expression in eukaryotic cells. Essential features include; an origin of replication allowing for production in bacteria, a bacterial antibiotic resistance gene allowing for plasmid selection in bacterial culture, a strong constitutive promotor for optimal expression in mammalian cells (promoters derived from cytomegalovirus (CMV) or simian virus provide the highest gene expression), a polyadenylation sequence to stabilise the mRNA transcripts, such as bovine growth hormone (BHG) or simian virus polyadenylation, and a multiple cloning site for insertion of an antigen gene. An intron A sequence improves expression of genes remarkably. Many bacterial DNA vaccine vectors contain unmethylated cytidinephosphate-guanosine (CpG) dinucleotide motifs that may elicit strong innate immune responses in the host. In recent years there have been several approaches to enhance and customise the immune response to DNA vaccine constructs (2nd generation DNA vaccines). For instance dicistronic vectors or multiple gene expressing plasmids have been used to express two genes simultaneously. Specific promoters have been engineered that restrict gene expression to certain tissues, and cytokine/antigen fusion genes have been constructed to enhance the immune response. Furthermore, genes may be codon optimised for optimal gene expression in the host and naïve leader sequences may be substituted with optimised leaders increasing translation efficiency.

The administration of DNA vaccine can be by saline or buffered saline injection of naked DNA or RNA, or injection of DNA plasmid or linear gene expressing DNA fragments coupled to particles or delivered by a viral vector such as Adenovirus, Modified vaccinia virus Ankara (MVA), Vaccinia, Adenoassociated virus (AAV), Alphavirus etc. DNA vaccines could be delivered either by gene gun as in the previous examples or as injection with or without electroporation.

When using DNA vaccine encoding surface proteins (HA and/or NA) of a pandemic strain (e.g. 1918 H1N1 or 1968 H3N2 or 1957 H2N2) in combination with HA and/or NA from present day drifted strains of H1N1 or H3N2 or H2N2 we envision a preferentially induction of cross-reacting antibodies (broadly protective antibodies) to shared more conserved antibody and T cell epitopes. Therefore a broader protection should be obtained when vaccinating with surface proteins either as a DNA vaccine and/or a protein vaccine deriving from the mentioned original pandemic strains together with HA and/or NA from present day virus strains as DNA vaccine and/or a protein vaccine, and importantly this can be done either as a mixture or as a sequential (prime-boost) with pandemic or present day antigens first and present day or pandemic strains at a later time point. As a consequence we will obtain a broader anti-influenza A response by vaccinating (DNA and/or protein) from pandemic strains in individuals already vaccinated with present day protein vaccine. Vise versa we may get a broader anti-influenza coverage against coming influenza strains when primed with HA and/or NA DNA and/or protein from the pandemic strains and boosted with an influenza protein vaccine at any time point in the future.

Codon Optimization:

Codon optimization is the complete exchange of the virus codons to those of highly expressed human genes and therefore also mammalian genes that include swine. Codon optimization do not change the encoded amino acids of the protein antigens encoded but may increase the eukaryotic protein expression in mammalian cells. Since genes of highly expressed human proteins has a high content of C and G, there are an increased possibility of generating both immune stimulatory GpG motifs, but also immune inhibitory GC sequences. Genes engineered using codon optimization is called "humanized" genes and are frequently used in DNA vaccines to enhance expression.

The DNA or RNA sequence for haemagglutinin and neuraminidase and matrix and nucleoprotein is changed so the sequence coding for said proteins is changed to be optimally expressed in humans and swine or the host for which the vaccine is intended.

The invention discloses the use of the novel influenza A (H1N1)v HA and/or NA codon-optimized genes in a DNA immunogenic composition or vaccine and the combination of these novel H1N1 pandemic glycoprotein genes with previous pandemic H1N1 genes encoding internal proteins in a DNA immunogenic composition or vaccine.

TABEL 1

H1N1 Nucleotide and amino acid sequences of the codon optimized genes and the proteins they express.

HA 1918 synthetic gene 0607838, Base on acc. No. AF11721: A/South Carolina/1/18

Nucleotide
ATGGAGGCCAGGCTGCTGGTGCTGCTGTGCGCCTTCGCCGCCACCAACG
CCGACACCATCTGCATCGGCTACCACGCCAACAACAGCACCGACACCGT
GGATACCGTGCTGGAGAAGAACGTGACCGTGACCCACAGCGTGAACCTG
CTGGAGGACAGCCACAACGGCAAGCTGTGCAAGCTGAAGGGAATCGCTC
CCCTGCAGCTGGGCAAGTGCAACATCGCCGGCTGGCTGCTGGGCAACCC
CGAGTGCGACCTGCTGCTGACCGCCAGCAGCTGGTCCTACATCGTGGAG
ACCAGCAACAGCGAGAACGGCACCTGCTACCCCGGCGACTTCATCGACT
ACGAGGAGCTGCGGGAGCAGCTGTCCAGCGTGAGCAGCTTCGAGAAGTT
CGAGATCTTCCCCAAGACCAGCTCCTGGCCCAACCACGAGACCACCAAG
GGCGTGACCGCCGCCTGTAGCTACGCCGGAGCCAGCAGCTTCTACAGAA
ACCTGCTGTGGCTGACCAAGAAGGGCAGCAGCTACCCCAAGCTGTCCAA
GAGCTACGTGAACAACAAGGGCAAGGAAGTGCTGGTGCTGTGGGGCGTG
CACCACCCCCTACCGGCACCGACCAGCAGAGCCTGTACCAGAACGCCG
ACGCCTACGTGAGCGTGGGCAGCAGCAAGTACAACAGAAGGTTCACCCC
CGAGATCGCCGCCAGGCCCAAGGTGCGCGACCAGGCCGGCAGGATGAAC
TACTACTGGACCCTGCTGGAGCCCGGCGACACCATCACCTTCGAGGCCA
CCGGCAACCTGATCGCCCCTTGGTACGCCTTCGCCCTGAACAGGGGCAG
CGGCAGCGGCATCATCACCAGCGACGCCCCCCGTGCACGACTGCAACACC
AAGTGCCAGACCCCCACGGAGCCATCAACAGCAGCCTGCCCTTCCAGA
ACATCCACCCCGTGACCATCGGCGAGTGCCCCAAGTACGTGAGAAGCAC
CAAGCTGAGGATGGCCACCGGCCTGAGGAACATCCCCAGCATCCAGAGC
AGGGGCCTGTTCGGAGCCATCGCCGGATTCATCGAGGGCGGCTGGACCG

TABEL 1-continued

H1N1 Nucleotide and amino acid sequences of the codon optimized genes and the proteins they express.

GCATGATCGACGGCTGGTACGG

TABEL 1-continued

H1N1 Nucleotide and amino acid sequences of the codon optimized genes and the proteins they express.

Amino acid
M1 protein
MSLLTEVETYVLSIVPSGPLKAEIAQRLEDVFAGKNTDLEALMEWLKTR
PILSPLTKGILGFVFTLTVPSERGLQRRRFVQNALNGNGDPNNMDRAVK
LYRKLKREITFHGAKEVALSYSAGALASCMGLIYNRMGTVTTEVAFGLV
CATCEQIADSQHRSHRQMVTTTNPLIRHENRMVLASTTAKAMEQMAGSS
EQAAEAMEVASQARQMVQAMRTIGTHPSSSAGLKDDLIENLQAYQKRMG
VQMQRFK.

M2 protein
MSLLTEVETPTRNEWGCRCNDSSDPLVIAASIIGILHLILWILDRLFFK
CIYRRLKYGLKRGPSTEGVPESMREEYRKEQQSAVDVDDGHFVNIELE.

HA 2009 H1N1v synthetic gene, based on acc.
No ACP41105: A/California/04/09 atgaaggctatcctggtggtgctgctgtacaccttcgccaccgccaacg
ccgataccctgtgcatcggctaccacgccaacaacagcaccgacaccgt
ggataccgtgctggaaaagaacgtgaccgtgacccacagcgtgaacctg
ctggaagataagcacaacggcaagctgtgcaagctgagaggcgtggccc
tctcgcacctgggcaagtgcaatatcgccggctggatcctgggcaacc
cgagtgcgagagcctgagcaccgccagctcttggtcctacatcgtggag
acacccagcagcgacaacggcacctgttaccccggcgacttcatcgact
acgaggaactgcgggagcagctgtccagcgtgtccagcttcgagcggtt
cgagatcttcccgaagaccagctcctggcccaaccacgacagcaacaag
ggcgtgaccgccgcctgtcctcacgctggggcaagacttctacaaga
acctgatctggctggtgaagaagggcaacagctacccaagctgtccaa
gagctacatcaacgacaaggcaaagaggtgctggtgctgtggggcatc
caccaccctagcaccagcgccgaccagcagagcctgtaccagaacgcg
acacctacgtgttcgtgggcagcaggtacagcaagaagttcaagcc
cgagatcgccatcagaccaaagtgcgggaccaggaaggccggatgaac
tactactggaccctggtggagcccggcgacaagatcaccttcgaggcca
ccggcaatctggtggtgcccagatacgccttcgccatggaaagaaacgc
cggcagcggcatcatcatcagcgaccccgtgcacgactgcaacacc
acctgtcagacccccaaggggcatcaacaccagcctgcccttccaga
acatccaccccatcaccatcggcaagtgccctaagtacgtgaagtccac
caagctgagactggccaccggcctgcggaacatcccagcatccagagc
agaggcctgttcggggcattgccggcttcatcgaggggcggctggaccg
gaatggtggacgggtgggtacgactaccaccaccagaatgagcaggcg
cggctacgccgccgacctgaagtccacacagaacgccatcgacgagatc
accaacaaagtgaacagcgtgatcgagaagatgaacacccagttcaccg
ccgtgggcaaagagttcaaccacctggaaaagcgatcgagaacctgaa
caagaaggtggacgacggcttcctggacatctggaccttacaacgccgag
ctgctggtgctgctggaaaacgagcggaccctggactaccacgactcca
acgtgaagaatctgtacgagaaagtgcgggagccagctgaagaacaacgc
caaagatcggcaacggctgcttcgagttctacaagctgcgacaac
acctgtatggaaagcgtgaagaacggcacctacgactacccaagtaca
gcgaggaagccaagctgaaccgggaagagatcgacgtcgtgaagctgga
aagcacccggatctaccagatcctggccatctacagcaccgtggccagc
tcactggtcctggtcgtgtccctgggcgctatcagcttctgatgtgca
gcaacggcagcctgcagtgccggatctgcatctgaggcgccgagaattc
ttaattaa Amino acid sequence MKAILVVLYTFATANADTLCIGYHANNSTDTVDTVLEKNVTVTHSVNLL
EDKHNGKLCKLRGVAPLHLGKCNIAGWILGNPECESLSTASSWSYIVET
PSSDNGTCYPGDFIDYEELREQLSSVSSFERFEIFPKTSSWPNHDSNKG
VTAACPHAGAKSFYKNLIWLVKKGNSYPKLSKSYINDKGKEVLVLWGIH
HPSTSADQQSLYQNADTYVFVGSSRYSKKFKPEIAIRPKVRDQEGRMNY
YWTLVEPGDKITFEATGNLVVPRYAFAMERNAGSGIIISDTPVHDCNTT
CQTPKGAINTSLPFQNIHPITIGKCPKYVKSTKLRLATGLRNIPSIQSR
GLFGAIAGFIEGGWTGMVDGWYGYHHQNEQGSGYAADLKSTQNAIDEIT
NKVNSVIEKMNTQFTAVGKEFNHLEKRIENLNKKVDDGFLDIWTYNAEL
LVLLENERTLDYHDSNVKNLYEKVRSQLKNNAKEIGNGCFEFYHKCDNT
CMESVKNGTYDYPKYSEEAKLNREEIDGVKLESTRIYQILAIYSTVASS
LVLVVSLGAISFWMCSNGSLQCRICI NA 2009 H1N1v synthetic gene, based on acc.
No ACP41107: A/California/04/09 atgaaccccaaccagaagatcatcaccatcggcagcgtgtgcatgacca
tcggcatggccaacctgatcctgcagatcggcaacatcatcagcatctg
gatcagccacagcatccagctgggcaaccagaaccagatcgagacatgc
aaccagagcgtgatcacctacgagaacaacaccgtgggtgaaccagacct
acgtgaacatcagcaacaccaacttcgccgctggccagagcgtggtgtc tgtgaagctggccggcaacagcagcctgtgccctgtgtccggctgggcc
atctacagcaaggacaacagcgtgcggatcggcagcaagggcgacgtgt
tcgtgatccggagccccttcatcagctgcagccccctggaatgccggac
cttcttcctgacccagggggccctgctgaacgacaagcacagcaacggc
accatcaaggacagaagccccctaccggaccctgatgagctgccccatcg
gcgaggtgccccagcccctacaacagcagattcgagtcctggcttggag
cgcctctgcctgccacgacggcatcaactggctgacaatcggcatcagc
ggccctgataacgcgctgtggccgtgctgaagtacaacggcatcatca
ccgacacaatcaagagctggcggaacaacatcctgcgacccaggaatc
cgagtcgcctgcgtgaacggcagctgcttcaccgtgatgaccgacggc
cctagcaatggccaggcagctacaagatcttccggatcgagaagggca
agatcgtgaagtccgtggagatgaacgcccccaactaccactacgagga
atgcagctgctaccccgacagcagcgagatcacctgtgtgtgccagga
aactggcacggcagcaacagaccctgggtgtccttcaaccagaatctgg
aataccagatcggctactttgcagcggcatcttcggcgacaaccccag
acccaacgacaagaccggaagctgcggccctgtgtctagcaacgggggcc
aacggcgtgaagggcttcagcttcaagtacggcaatggcgtgtggatcg
gccggaccaagagcatcagcagccggaacggcttcgagatgatctgga
ccccaacggctggaccggcaccgacaacaacttcagcatcaaggaggac
atcgtgggcatcaacgagtggagcggctacagcggcagcttcgtgcagc
accctgagctgaccggcctggactgcatccggccctgcttttggtgga
gctgatcagaggcagaccaaagagaacaccatctgaccagcggcagc
agcatcagctttgcggcgtgaacagcgacaccgtgggctggtcttggc
ccgatggggccgagctgcccttcaccatcgacaagtgaggcgccgagaa
ttcttaattaa Amino acid sequence MNPNQKIITIGSVCMTIGMANLILQIGNIISIWISHSIQLGNQNQIETC
NQSVITYENNTWVNQTYVNISNTNFAAGQSVVSVKLAGNSSLCPVSGWA
IYSKDNSVRIGSKGDVFVIREPFISCSPLECRTFFLTQGALLNDKHSNG
TIKDRSPYRTLMSCPIGEVPSPYNSRFESVAWSASACHDGINWLTIGIS
GPDNGAVAVLKYNGIITDTIKSWRNNILRTQESECACVNGSCFTVMTDG
PSNGQASYKIFRIEKGKIVKSVEMNAPNYHYEECSCYPDSSEITCVCRD
NWHGSNRPWVSFNQNLEYQIGYICSGIFGDNPRPNDKTGSCGPVSSNGA
NGVKGFSFKYGNGVWIGRTKSISSRNGFEMIWDPNGWTGTDNNFSIKQD
IVGINEWSGYSGSFVQHPELTGLDCIRPCFWVELIRGRPKENTIWTSGS
SISFCGVNSDTVGWSWPDGAELPFTIDK HA H3N2 seasonal synthetic gene, based on acc.
No EU103823: A/Wisconsin/67/05 atgaaaaccatcatcgccctgagctacatcctgtgcctggtgttcgccc
agaagctgcccggcaacgacaacagcaccgccaccctgtgcctgggcca
ccacgccgtgcccaacggcaccatcgtcaaaaccattaccaatgatcag
atcgaggtgaccaacgccaccaagctggtgcagagcagcagcaccggcg
gcatctgcgacagccccaccagatcctgacggcgagaactgcacccct
gatctgacgctctgctcggcgaccctcagtgcgacggcttccagaacaag
aagtgggacctgttcgtcgagcgcagcaaggcctacagcaactgctacc
cctacgacgtgcccgactacgccagcctccgctccctggtcgcctccag
cggcaccctggagttcaacgacgagagcttcaactggaccgcgtgacc
cagaacggcaccagcagcagctgcaagcgcccgcagcaacaacagctct
tcagccgcctgaactggctgacccacctgaagttcaagtaccccgcctc
gaacgtgaccatgcccaacaatgagaaattcgacaagctgtacatctgg
ggcgtgcaccacccgtgaccgacaacgaccagatcttcctgtacgccc
aggcagcggcgccatcaccgtgagcaccaagcgcagcagcagaccgt
gatccccaacatcggcagccgcccaggatccgaacatccccagccgc
atcagcatctactggaccatcgtgaagcccggcgacatcctgctgatca
actccaccggcaacctgatcgcccccaggggcatcttcaagatccgcag
cggcaagagcagcatcatgcgcagcgaccccatcggcaagtgcaac
agcgagtgcatcaccccaacggcagcatccccaacgacaagcccttcc
agaacgtgaaccgcatcacctacggagcctgtcccgctacgtgaagca
gaacaccctgaaactggctaccggcatgcggaacgtgcccgagaagcag
accgggggcatcttcggggccatcgccggcttcatcgagaacggctggg
aggcatggtggacggctggtacggttcccaccagaactccgaggcg
catcccaggcgccgacctgaagagcaccccaggccgcatcaaccag
atcaacggcaagctgaaccgcctgatcggcaagaccaacgagaagttcc
accagatcgagaaggagtttagcgaggtcgagggccgcatccaggacct
ggagaagtacgtggaggacaccaagatcgacctgtggagctacaacgcc
gagctgctggtcgccctggaaaacgagcacaccatcgacctgaccgaca
gcgagatgaacaagctgttcgagcgcaccaagaagcagctcgccgagaa
cgccgaggacatgggcaacggctgcttcaagatctaccacaagtgcgac
aacgcctgcatcggctccatccgcaacggcacctacgaccacgacgtgt
accgcgacgaggccctgaacaaccgcttccagatcaagggcgtggagct
gaagagcggctacaaggactggatcctgtggatcagcttcgctatcagc

TABEL 1-continued

H1N1 Nucleotide and amino acid sequences of the codon optimized genes and the proteins they express.

tgcttcctgctgtgcgtggccctgctgggcttcatcatgtgggcctgcc
agaagggcaacatccgctgcaacatctgcatc

Amino acid

MKTIIALSYILCLVFAQKLPGNDNSTATLCLGHHAVPNGTIVKTITNDQ
IEVTNATELVQSSSTGGICDSPHQILDGENCTLIDALLGDPQCDGFQNK
KWDLFVERSKAYSNCYPYDVPDYASLRSLVASSGTLEFNDESFNWTGVT
QNGTSSSCKRRSNNSFFSRLNWLTHLKFKYPALNVTMPNNEKFDKLYIW
GVHHPVTDNDQIFLYAQASGRITVSTKRSQQTVIPNIGSRPRIRNIPSR
ISIYWTIVKPGDILLINSTGNLIAPRGYFKIRSGKSSIMRSDAPIGKCN
SECITPNGSIPNDKPFQNVNRITYGACPRYVKQNTLKLATGMRNVPEKQ
TRGIFGAIAGFIENGWEGMVDGWYGFRHQNSEGIGQAADLKSTQAAINQ
INGKLNRLIGKTNEKFHQIEKEFSEVEGRIQDLEKYVEDTKIDLWSYNA
ELLVALENQHTIDLTDSEMNKLFERTKKQLRENAEDMGNGCFKIYHKCD
NACIGSIRNGTYDHDVYRDEALNNRFQIKGVELKSGYKDWILWISFAIS
CFLLCVALLGFIMWACQKGNIRCNICI

NA H3N2 seasonal synthetic gene, based on acc. No: ISDN 136490: A/Wisconsin/67/05 atgaacccccaaccagaagatcatcaccatcggatccgtcagcctgacca
tctccaccatctgctttttcatgcagatcgccatcctgatcaccaccgt
gaccctgcacttcaagcagtacgagttcaacagcccccccaacaaccag
gtcatgctgtgcgagcccaccatcatcgagcgcaacatcaccgagatcg
tgtacctgaccaacaccaccatcgagaaagagatctgccccaagctggc
cgagtaccgcaactggtccaagcccagtgcaatatcacaggcttcgcc
cccttcagcaaggacaacagcatccgctgagcgctggagggggacatct
gggtcacccgcgagccctacgtgagctgcgacccgacaagtgctacca
gttcgccctcggacagggaccacactgaataacgtccacagcaacgac
accgtgcacgaccgcaccccctaccgcaccctgctgatgaacgagctgg
gcgtgcccttccacctgggcaccaagcaggtctgcatcgcctggtccag
cagcagctgccacgacggcaaggcctggctgcacgtgtgcgtgaccggc
gacgacaagaacgccaccgccagcttcatctacaacggccgcctggtgg
acagcatcgtgagctggtccaaagagatcctgcgcacccaagaaagcga
gtgcgtctgcatcaacggcacctgcaccgtggtgatgaccgacggcagc
gcctccggcaaggccgacaccaagatcctgttcatcgaagagggcaaga
tcgtgcaccagcacactgtccggcagcgcccagcacgtggaagagtg
cagctgctacccccgctacctgggcgtgcgctgcgtgtgccgcgacaac
tggaagggcagcaaccgccccatcgtggacatcaacatcaaggactact
ccatcgtgagcagctacgtgtgcagcggcctggtcggcgacacacccg
caagaacgacagcagctccagcagccactgcctggaccccaacaacgaa
gagggcggccacggcgtgaaggggtgggccttcgacgacggcaacgacg
tgtggatgggccgcaccatcagcgagaagctgcggagcggctatgagac
attcaaggtgatcgagggctggtccaaccccaacagcaagctgcagatc
aaccgccaggtgatcgtggaccgcggcaaccgctccggctacagcggca
tcttcagcgtggagggcaagtcctgcatcaaccgctgcttctatgtgga
gctgattcgggggaggaaagaagagaccgaggtcctctggaccagcaac
agcatcgtggtgttctgcggcaccagcggcacctacggcaccggcagct
ggcccgacggggccgacatcaacctgatgcccatctga

Amino acid

MNPNQKIITIGSVSLTISTICFFMQIAILITTVTLHFKQYEFNSPPNNQ
VMLCEPTIIERNITEIVYLTNTTIEKEICPKLAEYRNWSKPQCNITGFA
PFSKDNSIRLSAGGDIWVTREPYVSCDPDKCYQFALGQGTTLNNVHSND
TVHDRTPYRTLLMNELGVPFHLGTKQVCIAWSSSCHDGKAWLHVCVTG
DDKNATASFIYNGRLVDSIVSWSKEILRTQESECVCINGTCTVVMTDGS
ASGKADTKILFIEEGKIVHTSTLSGSAQHVEECSCYPRYLGVRCVCRDN
WKGSNRPIVDINIKDYSIVSSYVCSGLVGDTPRKNDSSSSSHCLDPNNE
EGGHGVKGWAFDDGNDVWMGRTISEKLRSGYETFKVIEGWSNPNSKLQI
NRQVIVDRGNRSGYSGIFSVEGKSCINRCFYVELIRGRKEETEVLWTSN
SIVVFCGTSGTYGTGSWPDGADINLMPI.

All natural genes applied in the current DNA vaccines are public available as nucleotide and amino acid sequences but can be translated into optimal vaccine DNA genes by synthesis using optimal codons for eukaryotic mammalian expression using standard expression vectors (key features: CMV promoter, intron A, Kozac sequence, vaccine gene inclusive its secretion sequence, stop codon, PolyAdenylation) A clinical irrelevant kanamycin resistance gene are included for growth and selection in transfected *E. coli* for plasmid DNA production.

The 1918 HA and NA amino sequences are public available (GenBank A/South Carolina/1/18 AF117241, A/Brevig Mission/1/18 AF250356) and can be translated into DNA using standard optimal codons for eukaryotic mammalian expression using standard expression vectors (key features: CMV promoter, intron A, Kozac sequence, vaccine gene inclusive its secretion sequence, stop codon, PolyAdenylation) A kanamycin resistance gene are included for growing and selection of transfected *E. coli* for plasmid DNA production.

DNA vaccination with the 1918 H1N1 HA and NA synthetic codon optimized genes using gene gun standard conditions induces protective immunity to present day circulating influenza A virus as exemplified using A/New Calcdonia/20/99(H1N1) virus challenge in DNA vaccinated ferrets (*Mustela Putorius Furo*). This is highly surprising since the two virus are separated by more than 80 years of antigenic drift and show about 21% difference in the HA1 protein. Normally a protective protein vaccine must be based upon the amino acid sequence of the circulating seasonal influenza A strain to induce protection. Moreover the protection by the 1918 DNA vaccine against 2007 circulating strain is more consistent than the traditional protein vaccine based on the homologous circulating strain (New Calcdonia). This suggest that the 1918 based DNA vaccine induces a much broader protective immunity that protects against influenza A H1N1 strains from 1918 to present time and perhaps beyond.

The unusual broad protection may be due to a unique amino acid sequence in the 1918 HA and/or NA proteins inducing broader protective antibodies to special epitopes or cellular immunity or immune adjuvans effect, or a particular gene expression or particular immune induction by the optimized nucleotide sequence of the particular 1918 H1N1 genes, or some or all of these factors in combination.

The advantages are that a limited number of vaccine components delivered as a DNA vaccine either as naked DNA or RNA as plasmid or linear encoding sequences or incorporated into recombinant virus for more efficient delivery The discovery of a broad protection induced by the pandemic influenza A strain 1918 H1N1 may suggest that a similar good protection may be obtained against circulating H2 strains using DNA vaccines based on HA and/or NA from the 1958 H2N2 pandemic strain and against circulating H3 strains using DNA vaccines based in HA and/or NA from the 1968 pandemic strain.

The unusual broad and/or efficient protection obtained using a pandemic influenza A strain instead of the present day circulating strains is due to special features in the sequence of the first new pathogenic and spreading virus. These features may gradually vain by accumulation of sequence changes during years of adaptation to the human and swine population.

One of these features is the accumulation of N-linked glycosylations of the glycoproteins. Since the first introductions of the pandemic H1N1 and H3N2 the glycoproteins have gained several gycosylations (FIG. 1). The oligosaccharides are added to asparagines (N) in the tripeptide sequence Asn-X-Ser of Asn-X-Thr, where X could be any amino acid except proline. If these glycosylations occur in or nearby an antigenic binding site they camouflage the binding sites for recognition by the host antibodies. The glycosylation sites at positions 126 and 144 in the H3 haemagglutinin have been variable since 1999 in Denmark, these sites are located in the HA antigenic site A and are therefore expected to influence on host antibody recognition.

These sites and other in or near antigenic sites in HA and/or NA can be erased to give a broader cross-protection than fully glycosylated antigens.

A shown the present time viruses A/New Calcdonia/20/99 and A/Wisconsin/67/05 comprise more predicted N-glycosylated sites than the original pandemic H1N1 or H3N2 strains (FIG. 1).

A DNA vaccine stripped for glycosylations in, and in close vicinity of, the antigenic sites of both HA and NA would induce a broader subtype recognition.

The unusual broad protection we have observed with DNA vaccines based on pandemic strains is due to unique features of an unadapted pandemicstrain e.g. ability of the pandemic genes inducing broader protective antibodies and cellular immunity due to less masked cross-reactive antigenic sites or immune adjuvans effect etc., The influenza virus haemagglutinin accumulates glycosylations and thereby camouflages its antigenic sites for recognition by the host immune system. The good cross protection observed by applying the pandemic genes in the influenza DNA vaccine is partly explained by the few glycosylation sites in these genes which we suggest in the analysis in the Table below:

| Asparagines predicted to be N-glycosylated [a] Amino acid position | | | | |
|---|---|---|---|---|
| HA H1N1 1918 | HA H1N1 1999 | HA H1N1v 2009 | HA H3N2 1968 | HA H3N2 2005 |
| 11 | 11 | 11 | 8 | 8 |
| 23 | 23 | 23 | 22 | 22 |
| 87 | 87 | 87 | 38 | 63 |
| 287 | 125 | 287 | 81 | 133 |
| 481 * | 154 | 481 * | 165 | 144 |
| 540 * | 286 (287) | 540 * | 285 | 165 |
|  | 480 * (481) |  | 483 * | 246 |
|  | 539 * (540) |  |  | 285 |
|  |  |  |  | 483 * |

[a] Amino acid numbering follows H1N1 and H3N2 respectively.
* Positions also positively predicted; however, the sequons are positioned in the HA2 region, not likely to be glycosylated.

The pandemic glycoproteins of a current pandemic either alone or in combination with previous pandemic genes or seasonal influenza virus genes in a DNA vaccine will induce optimal protection against the current pandemic virus and the following drifted versions of the same subtype.

The DNA or RNA sequence for haemagglutinin and neuraminidase, e.g. from non-pandemic seasonal strains, can be changed so the sequence coding for said proteins is changed to code for said proteins with less or no glycosylation sites.

The advantages are that a limited number of vaccine components delivered as a DNA vaccine either as naked DNA or RNA, as plasmid, or linear encoding sequences, or incorporated into recombinant virus, or a lipid-based formulation for more efficient delivery The universal seasonal influenza A DNA vaccine should comprise H1N1 HA and/or NA glycoproteins from the most recent H1N1 pandemic, H3N2 HA and/or NA glycoproteins from the last H3N2 pandemic and/or the most recent epidemic together with the genes coding for the internal genes. The internal genes NP and/or M from one of the pandemics e.g. H1N1 1918 that has shown protection in our animal model.

The DNA construct used is a modified WRG7079 plasmid (Backbone MVLF #1528). Our synthetic flu genes codon optimised for humans have been inserted between the Kas1 and Mlu1 restriction sites in the expression vector.

TABEL 2

H3N2 and H2N2 nucleotide and amino acid sequences of the genes (not codon optimized).

HA H3N2 Acc. No.: AB295605: A/Aichi/2/1968(H3N2)

Nucleotide
ATAATTCTATTAATCATGAAGACCATCATTGCTTTGAGCTACATTTTCT
GTCTGGCTCTCGGCCAAGACCTTCCAGGAAATGACAACAGCACAGCAAC
GCTGTGCCTGGGACATCATGCGGTGCCAAACGGAACACTAGTGAAAACA
ATCACAGATGATCAGATTGAAGTGACTAATGCTACTGAGCTAGTTCAGA
GCTCCTCAACGGGGAAAATATGCAACAATCCTCATCGAATCCTTGATGG
AATAGACTGCACACTGATAGATGCTCTATTGGGGGACCCTCATTGTGAT
GTTTTTCAAAATGAGACATGGGACCTTTTCGTTGAACGCAGCAAAGCTT
TCAGCAACTGTTACCCTTATGATGTGCCAGATTATGCCTCCCTTAGGTC
ACTAGTTGCCTCGTCAGGCACTCTGGAGTTTATCACTGAGGGTTTCACT
TGGACTGGGGTCACTCAGAATGGGGGAAGCAATGCTTGCAAAAGGGGAC
CTGGTAGCGGTTTTTTCAGTAGACTGAACTGGTTGACCAAATCAGGAAG
CACATATCCAGTGCTGAACGTGACTATGCCAAACAATGACAATTTTGAC
AAACTATACATTTGGGGGGTTCACCACCCGAGCACGAACCAAGAACAAA
CCAGCCTGTATGTTCAAGCATCAGGGAGGAGTCACAGTCTCTACCAGGAG
AAGCCAGCAAACTATAATCCCGAATATCGAGTCCAGACCCTGGGTAAGG
GGTCGTCTAGTAGAATAAGCATCTATTGGACAATAGTTAAGCCGGGAG
ACGTACTGGTAATTAATAGTAATGGGAACCTAATCGCTCCTCGGGGTTA
TTTCAAAATGCGCACTGGGAAAAGCTCAATAATGAGGTCAGATGCACCT
ATTGATACCTGTATTTCTGAATGCATCACTCCAAATGGAAGCATTCCCA
ATGACAAGCCCTTTCAAAACGTAAACAAGATCACATATGGAGCATGCCC
CAAGTATGTTAAGCAAAACACCCTGAAGTTGGCAACAGGGATGCGGAAT
GTACCAGAGAAACAAACTAGAGGCCTATTCGGCGCAATAGCAGGTTTCA
TAGAAAATGGTTGGGAGGGAATGATAGACGGTTGGTACGGTTTCAGGCA
TCAAAATTCTGAGGGCACAGGACAAGCAGCAGATCTTAAAAGCACTCAA
GCAGCCATCGACCAAATCAATGGGAATTGAACAGGGTAATCGAGAAGA
CGAACGAGAAATTCCATCAAATCGAAAAGGAATTCTCAGAAGTAGAAGG
GAGAATTCAGGACCTCGAGAAATACGTTGAAGACACTAAAATAGATCTC
TGGTCTTACAATGCGGAGCTTCTTGTCGCTCTGGAGAATCAACATACAA
TTGACCTGACTGACTCGGAAATGAACAAGCTGTTTGAAAAAACAAGGAG
GCAACTGAGGGAAAATGCTGAAGACATGGGCAATGGTTGCTTCAAAATA
TACCACAAATGTGACAACGCTTGCATAGAGTCAATCAGAAATGGGACTT
ATGACCATGATGTATACAGAGACGAAGCATTAAACAACCGGTTTCAGAT
CAAAGGTGTTGAACTGAAGTCTGGATACAAAGACTGGATCCTGTGGATT
TCCTTTGCCATATCATGCTTTTTGCTTTGTGTTGTTTTGCTGGGGTTCA
TCATGTGGGCCTGCCAGAGAGGCAACATTAGGTGCAACATTTGCATTTG
AGTGTATTAGTAATTA Amino acid
MKTIIALSYIFCLALGQDLPGNDNSTATLCLGHHAVPNGTLVKTITDDQ
IEVTNATELVQSSSTGKICNNPHRILDGIDCTLIDALLGDPHCDVFQNE
TWDLFVERSKAFSNCYPYDVPDYASLRSLVASSGTLEFITEGFTWTGVT
QNGGSNACKRGPGSGFFSRLNWLTKSGSTYPVLNVTMPNNDNFDKLYIW
GVHHPSTNQEQTSLYVQASGRVTVSTRRSQQTIIPNIESRPWVRGLSSR
ISIYWTIVKPGDVLVINSNGNLIAPRGYFKMRTGKSSIMRSDAPIDTCI
SECITPNGSIPNDKPFQNVNKITYGACPKYVKQNTLKLATGMRNVPEKQ
TRGLFGAIAGFIENGWEGMIDGWYGFRHQNSEGTGQAADLKSTQAAIDQ
INGKLNRVIEKTNEKFHQIEKEFSEVEGRIQDLEKYVEDTKIDLWSYNA
ELLVALENQHTIDLTDSEMNKLFEKTRRQLRENAEDMGNGCFKIYHKCD
NACIESIRNGTYDHDVYRDEALNNRFQIKGVELKSGYKDWILWISFAIS
CFLLCVVLLGFIMWACQRGNIRCNICI NA H3N2 Acc. No.: AB29606: A/Aichi/2/1968(H3N2)

Nucleotide
GAAAATGAATCCAAATCAAAAGATAATAACAATTGGCTCTGTCTCTCTC
ACCATTGCAACAGTATGCTTCCTCATGCAGATTGCCATCCTGGTAACTA
CTGTAACATTGCATTTTAAGCAATATGAGTGCGACTCCCCCGCGAGCAA
CCAAGTAATGCCGTGTGAACCAATAATAATAGAAAGGAACATAACAGAG
ATAGTGTATTTGAATAACACCACCATAGAGAAAGAGATATGCCCCAAAG
TAGTGGAATACAGAAATTGGTCAAAGCCGCAATGTCAAATTACAGGATT
TGCACCTTTTTCTAAGGACAATTCAATCCGGCTTTCTGCTGGTGGGGAC
ATTTGGGTGACGAGAGAACCTTATGTGTCATGCGATCATGGCAAGTGTT
ATCAATTTGCACTCGGGCAGGGGACCACACTAGACAACAAACATTCAAA
TGACACAATACATGATAGAATCCCTCATCGAACCCTATTAATGAATGAG
TTGGGTGTTCCATTTCATTTAGGAACCAGGCAAGTGTGTATAGCATGGT
CCAGCTCAAGTTGTCACGATGGAAAAGCATGGCTGCATGTTTGTATCAC
TGGGGATGACAAAAATGCAACTGCTAGCTTCATTTATGACGGGAGGCTT
GTGGACAGTATTGGTTCATGGTCTCAAAATATCCTCAGAACCCAGGAGT
CGGAATGCGTTTGTATCAATGGGACTTGCACAGTAGTAATGACTGATGG
AAGTGCTTCAGGAAGAGCCGATACTAGAATACTATTCATTGAAGAGGGG
AAAATTGTCCATATTAGCCCATTGTCAGGAAGTGCTCAGCATGTAGAAG
AGTGTTCCTGTTATCCTAGATATCCTGGCGTCAGATGTATCTGCAGAGA
CAACTGGAAGGCTCTAATAGGCCCGTCGTAGACATAAATATGGAAGAT TABEL 2-continued H3N2 and H2N2 nucleotide and amino acid sequences of the genes (not codon optimized).

TATAGCATTGATTCCAGTTATGTGTGCTCAGGGCTTGTTGGCGACACAC
CTAGAAACGACGACAGATCTAGCAATAGCAATTGCAGGAATCCTAATAA
TGAGAGAGGGAATCAAGGAGTGAAAGGCTGGGCCTTTGACAATGGAGAT
GACGTGTGGATGGGAAGAACGATCAGCAAGGATTTACGCTCAGGTTATG
AAACTTTCAAAGTCATTGGTGGTTGGTCCACACCTAATTCCAAATCGCA
GATCAATAGACAAGTCATAGTTGACAGCGATAATCGGTCAGGTTACTCT
GGTATTTTCTCTGTTGAGGGCAAAAGCTGCATCAATAGGTGCTTTTATG
TGGAGTTGATAAGGGGAAGGAAACAGGAGACTAGAGTGTGGTGGACCTC
AAACAGTATTGTTGTGTTTTGTGGCACTTCAGGTACCTATGGAACAGGC
TCATGGCCTGATGGGGCGAACATCAATTTCATGCCTATATAAGCTTTCG
CAATTTTAGA

Amino acid
MNPNQKIITIGSVSLTIATVCFLMQIAILVTTVTLHFKQYECDSPASNQ
VMPCEPIIIERNITEIVYLNNTTIEKEICPKVVEYRNWSKPQCQITGFA
PFSKDNSIRLSAGGDIWVTREPYVSCDHGKCYQFALGQGTTLDNKHSND
TIHDRIPHRTLLMNELGVPFHLGTRQVCIAWSSSSCHDGKAWLHVCITG
DDKNATASFIYDGRLVDSIGSWSQNILRTQESECVCINGTCTVVMTDGS
ASGRADTRILFIEEGKIVHISPLSGSAQHVEECSCYPRYPGVRCICRDN
WKGSNRPVVDINMEDYSIDSSYVCSGLVGDTPRNDDRSSNSNCRNPNNE
RGNQGVKGWAFDNGDDVWMGRTISKDLRSGYETFKVIGGWSTPNSKSQI
NRQVIVDSDNRSGYSGIFSVEGKSCINRCFYVELIRGRKQETRVWWTSN
SIVVFCGTSGTYGTGSWPDGANINFMPI HA H2N2 Acc. No.: CY022013: A/Albany/20/1957(H2N2)

Nucleotide
ATAGACAACCAAAAGCAAAACAATGGCCATCATTTATCTCATTCTCCTG
TTCACAGCAGTGAGAGGGGACCAGATATGCATTGGATACCATGCCAATA
ATTCCACAGAGAAGGTCGACACAATTCTAGAGCGGAACGTCACTGTGAC
TCATGCCAAGGACATTCTTGAGAAGACCCATAACGGAAAGTTATGCAAA
CTAAACGGAATCCCTCCACTTGAACTAGGGGACTGTAGCATTGCCGGAT
GGCTCCTTGGAAATCCAGAATGTGATAGGCTTCTAAGTGTGCCAGAATG
GTCCTATATAATGGAGAAAGAAAACCCGAGAGACGGTTTGTGTTATCCA
GGCAGCTTCAATGATTATGAAGAATTGAAACATCTCCTCAGCAGCGTGA
AACATTTCGAGAAAGTAAAGATTCTGCCCAAAGATAGATGGACACAGCA
TACAACAACTGGAGGTTCACGGGCCTGCGCGGTGTCTGGTAATCCATCA
TTCTTCAGGAACATGATCTGGCTGACAAAGAAAGGATCAAATTATCCGG
TTGCCAAAGGATCGTACAACAATACAAGCGGAGAACAAATGCTAATAAT
TTGGGGGTGCACCATCCCAATGATGAGACAGAACAAAGAACATTGTAC
CAGAATGTGGGAACCTATGTTTCCGTAGGCACATCAACATTGAACAAAA
GGTCAACCCCAGACATAGCAACAAGGCCTAAAGTGAATGGACTAGGAAG
TAGAATGGAATTCTCTTGGACCCTATTGGATATGTGGGACACCATAAAT
TTTGAGAGTACTGGTAATCTAATTGCACCAGAGTATGGATTCAAAATAT
CGAAAAGAGGTAGTTCAGGGATCATGAAAACAGAAGGAACACTTGGGAA
CTGTGAGACCAAATGCCAAACTCCTTTGGGAGCAATAAATACAACATTG
CCTTTTCACAATGTCCACCCACTGACAATAGGTGAGTGCCCCAAATATG
TAAAATCGGAGAAGTTGGTCTTAGCAACAGGACTAAGGAATGTTCCCCA
GATTGAATCAAGAGGATTGTTTGGGGCAATAGCTGGTTTTATAGAAGGA
GGATGGCAAGGAATGGTTGATGGTTGGTATGGATACCATCACAGCAATG
ACCAGGGATCAGGGTATGCAGCGGACAAAGAATCCACTCAAAAGGCATT
TGATGGAATCACCAACAAGGTAAATTCTGTGATTGAAAAGATGAACACC
CAATTTGAAGCTGTTGGGAAAGAATTCAGTAACTTAGAGAGAAGACTGG
AGAACTTGAACAAAAAGATGGAAGACGGGTTTCTAGATGTGTGGACATA
CAATGCTGAGCTTCTAGTTCTGATGGAAAATGAGAGGACACTTGACTTT
CATGATTCTAATGTCAAGAATCTGTATGATAAAGTCAGAATGCAGCTGA
GAGACAACGTCAAAGAACTAGGAAATGGATGTTTTGAATTTTATCACAA
ATGTGATGATGAATGCATGAATAGTGTGAAAAACGGGACGTATGATTAT
CCCAAGTATGAAGAAGAGTCTAAACTAAATAGAAATGAAATCAAAGGGG
TAAAATTGAGCAGCATGGGGGTTTATCAAATCCTTGCCATTTATGCTAC
AGTAGCAGGTTCTCTGTCACTGGCAATCATGATGGCTGGGATCTCTTTC
TGGATGTGCTCCAACGGGTCTCTGCAGTGCAGGATCTGCATATGATTAT
AAGTCATTTTATAATTAA Amino acid
MAIIYLILLFTAVRGDQICIGYHANNSTEKVDTILERNVTVTHAKDILE
KTHNGKLCKLNGIPPLELGDCSIAGWLLGNPECDRLLSVPEWSYIMEKE
NPRDGLCYPGSFNDYEELKHLLSSVKHFEKVKILPKDRWTQHTTTGGSR
ACAVSGNPSFFRNMIWLTKKGSNYPVAKGSYNNTSGEQMLIIWGVHHPN
DETEQRTLYQNVGTYVSVGTSTLNKRSTPDIATRPKVNGLGSRMEFSWT
LLDMWDTINFESTGNLIAPEYGFKISKRGSSGIMKTEGTLGNCETKCQT
PLGAINTTLPFHNVHPLTIGECPKYVKSEKLVLATGLRNVPQIESRGLF
GAIAGFIEGGWQGMVDGWYGYHHSNDQGSGYAADKESTQKAFDGITNKV
NSVIEKMNTQFEAVGKEFSNLERRLENLNKKMEDGFLDVWTYNAELLVL
MENERTLDFHDSNVKNLYDKVRMQLRDNVKELGNGCFEFYHKCDDECMN
SVKNGTYDYPKYEEESKLNRNEIKGVKLSSMGVYQILAIYATVAGSLSL
AIMMAGISFWMCSNGSLQCRICI NA H2N2 Acc. No.: CY022015: A/Albany/20/1957(H2N2)

Nucleotide
TGAAAATGAATCCAAATCAAAAGATAATAACAATTGGCTCTGTCTCTCT
CACCATTGCAACAGTATGCTTCCTCATGCAGATTGCCATCCTGGCAACT
ACTGTGACATTGCATTTTAAACAACATGAGTGCGACTCCCCCGCGAGCA
ACCAAGTAATGCCATGTGAACCAATAATAATAGAAAGGAACATAACAGA
GATAGTGTATTTGAATAACACCACCATAGAGAAAGAGATTTGCCCCGAA
GTAGTGGAATACAGAAATTGGTCAAAGCCGCAATGTCAAATTACAGGAT
TTGCACCTTTTTCTAAGGACAATTCAATCCGGCTTTCTGCTGGTGGGGA
CATTTGGGTGACGAGAGAACCTTATGTGTCATGCGATCCTGGCAAGTGT
TATCAATTTGCACTCGGGCAAGGGACCACACTAGACAACAAACATTCAA
ATGGCACAATACATGATAGAATCCCTCACCGAACCCTATTAATGAATGA
GTTGGGTGTTCCATTTCATTTAGGAACCAAACAAGTGTGTGTAGCATGG
TCCAGCTCAAGTTGTCACGATGGAAAAGCATGGTTGCATGTTTGTGTCA
CTGGGGATGATAGAAATGCGACTGCCAGCTTCATTTATGACGGGAGGCT
TGTGGACAGTATTGGTTCATGGTCTCAAAATATCCTCAGGACCCAGGAG
TCGGAATGCGTTTGTATCAATGGGACTTGCACAGTAGTAATGACTGATG
GAAGTGCATCAGGAAGAGCCGATACTAGAATACTATTCATTAAAGAGGG
GAAAATTGTCCATATCAGCCCATTGTCAGGAAGTGCTCAGCATATAGAG
GAGTGTTCCTGTTACCCTCGATATCCTGACGTCAGATGTATCTGCAGAG
ACAACTGGAAAGGCTCTAATAGGCCCGTTATAGACATAAATATGGAAGA
TTATAGCATTGATTCCAGTTATGTGTGCTCAGGGCTTGTTGGCGACACA
CCCAGGAACGACGACAGCTCTAGCAATAGCAATTGCAGGGATCCTAACA
ATGAGAGAGGGAATCCAGGAGTGAAAGGCTGGGCCTTTGACAATGGAGA
TGATGTATGGATGGGAAGAACAATCAACAAAGATTCACGCTCAGGTTAT
GAAACTTTCAAAGTCATTGGTGGTTGGTCCACACCTAATTCCAAATCGC
AGGTCAATAGACAGGTCATAGTTGACAACAATAATTGGTCTGGTTACTC
TGGTATTTTCTCTGTTGAGGGCAAAAGCTGCATCAATAGGTGCTTTTAT
GTGGAGTTGATAAGGGGAAGGCCACAGGAGACTAGAGTATGGTGGACCT
CAAACAGTATTGTTGTGTTTTGTGGCACTTCAGGTACTTATGGAACAGG
CTCATGGCCTGATGGGGCGAACATCAATTTCATGCCTATATAAGCTTTC
GCAATTTTAGAAAA Amino acid
MNPNQKIITIGSVSLTIATVCFLMQTAILATTVTLHFKQHECDSPASNQ
VMPCEPIIIERNITEIVYLNNTTIEKEICPEVVEYRNWSKPQCQITGFA
PFSKDNSIRLSAGGDIWVTREPYVSCDPGKCYQFALGQGTTLDNKHSNG
TIHDRIPHRTLLMNELGVPFHLGTKQVCVAWSSSSCHDGKAWLHVCVTG
DDRNATASFIYDGRLVDSIGSWSQNILRTQESECVCINGTCTVVMTDGS
ASGRADTRILFIKEGKIVHISPLSGSAQHIEECSCYPRYPDVRCICRDN
WKGSNRPVIDINMEDYSIDSSYVCSGLVGDTPRNDDSSSNSNCRDPNNE
RGNPGVKGWAFDNGDDVWMGRTINKDSRSGYETFKVIGGWSTPNSKSQV
NRQVIVDNNNWSGYSGIFSVEGKSCINRCFYVELIRGRPQETRVWWTSN
SIVVFCGTSGTYGTGSWPDGANINFMPI To further investigate the principle of a pandemic DNA vaccine, we designed a DNA vaccine based on the pandemic HA and NA genes of the Hong Flu 1968 H3N2 virus. Again, the pandemic DNA vaccine induced protection against a contemporary H3N2 virus infection. More rapid virus clearance and high antibody levels against the challenge strain was experienced.

Nucleotides and Proteins Covered by the Present Invention:

| Nucleotides and proteins | SEQ ID NO |
|---|---|
| Synthetic 1918 H1N1 HA DNA | 1 |
| 1918 H1N1 HA protein | 2 |
| Synthetic 1918 H1N1 NA DNA | 3 |
| 1918 H1N1 NA protein | 4 |
| Synthetic 1918 H1N1 NP DNA | 5 |
| 1918 H1N1 NP protein | 6 |
| Synthetic 1918 H1N1 M DNA | 7 |
| 1918 H1N1 M1 protein | 8 |
| 1918 H1N1 M2 protein | 9 |
| Synthetic 2009 H1N1v HA DNA | 10 |
| 2009 H1N1v HA protein | 11 |

-continued

| Nucleotides and proteins | SEQ ID NO |
|---|---|
| Synthetic 2009 H1N1v NA DNA | 12 |
| 2009 H1N1v NA protein | 13 |
| Synthetic seasonal H3N2 HA DNA | 14 |
| Seasonal H3N2 HA protein | 15 |
| Synthetic seasonal H3N2 NA DNA | 16 |
| Seasonal H3N2 NA protein | 17 |

FIGURE LEGENDS

FIG. 1: Predicted N-glycosylation sites in the haemagglutinin protein. N-glycosylated sequons predicted in HA of the pandemic a) H1N1 1918 (A/South Carolina/1/18(H1N1) and b) H3N2 1968 (A/Aichi/2/1968(H3N2)) compared to present time c) H1N1 (A/New Calcdonia/20/99(H1N1)) and d) H3N2 (A/Wisconsin/67/05) viruses above 0.5 threshold value.

Figure 2:
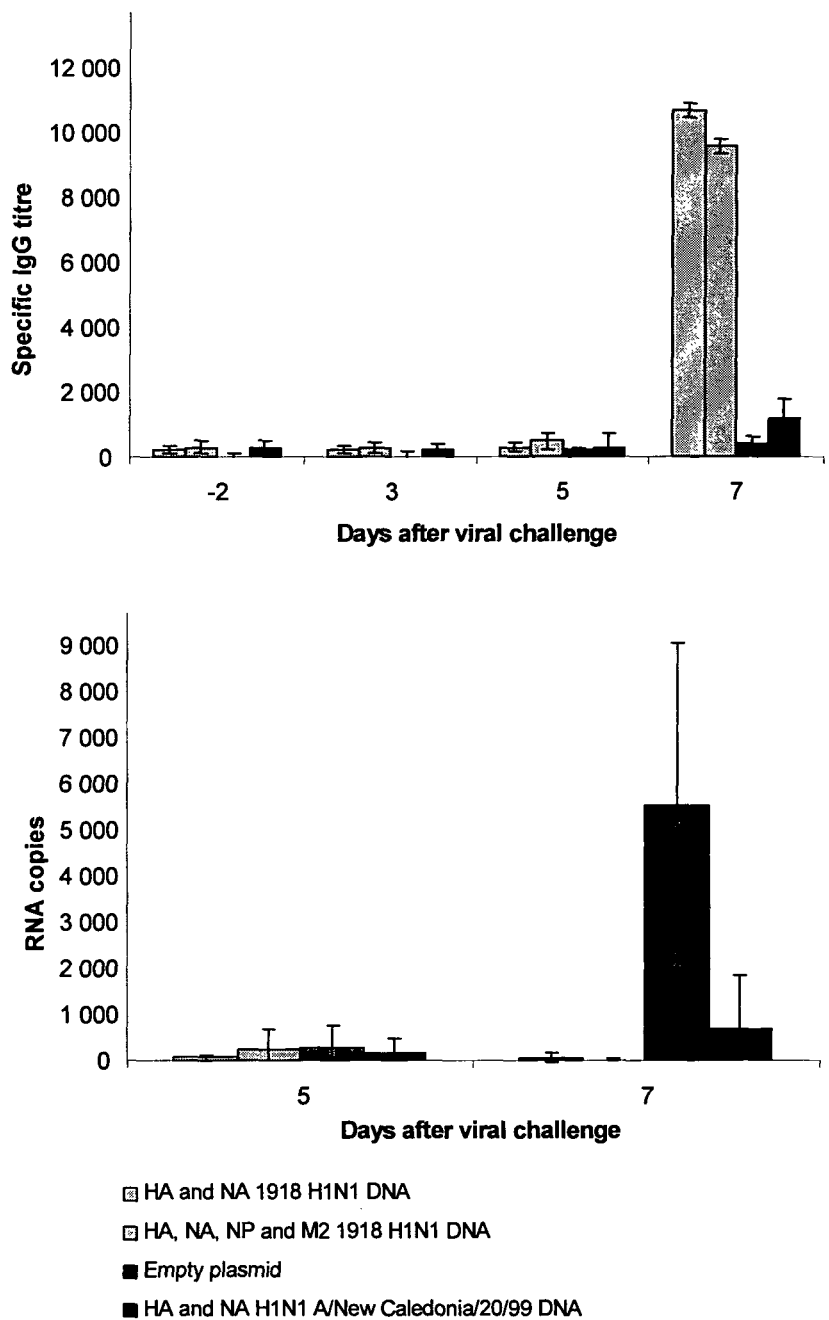

FIG. 2: Initial H1N1 DNA vaccine IgG antibody and virus titer results. Ferrets were vaccinated as in example 2 with codon optimised HA+NA 1918 H21N1 DNA and HA+NA+NP+M 1918 H1N1 or 1999 H1N1 HA+NA non-codon optimized present time virus DNA and challenged with a virus from 1947. (A) Mean serum specific IgG antibody response (ELISA) in ferrets to influenza A of A/New Calcdonia/20/99(H1N1) days after viral challenge and (B) number of viral RNA copies (real time RT/PCR) in nasal wash in days after challenge. Six ferrets in each group.

Figure 3:
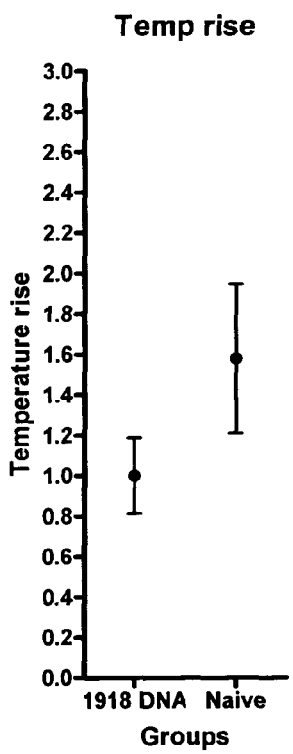
Figure 3:
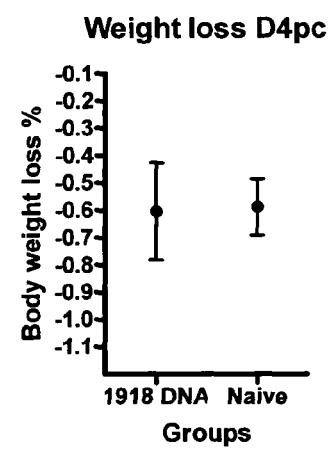
Figure 3:
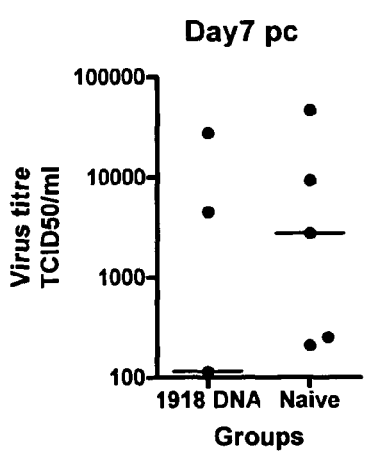
Figure 3:
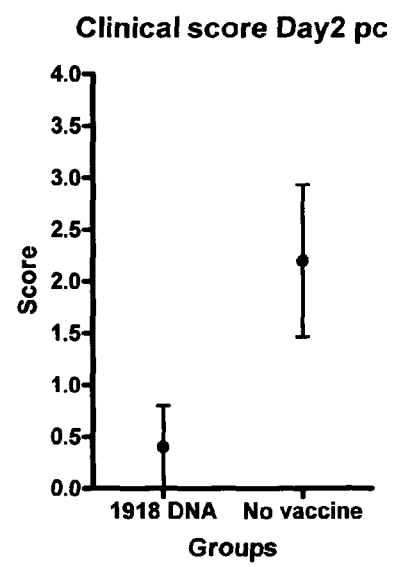

FIG. 3: HA+NA 1918 H1N1 pandemic H1N1 DNA vaccinated ferrets challenged with 1999 H1N1 virus circulating season 2007. (A) Fever at day 2 post challenge; (B) Body weight loss by day 4 post challenge; (C) Virus titre in nasal washings at day 7 post challenge; (D) Clinical score for illness based on a scoring table for sneezing, nasal discharge and activity level.

Figure 4:
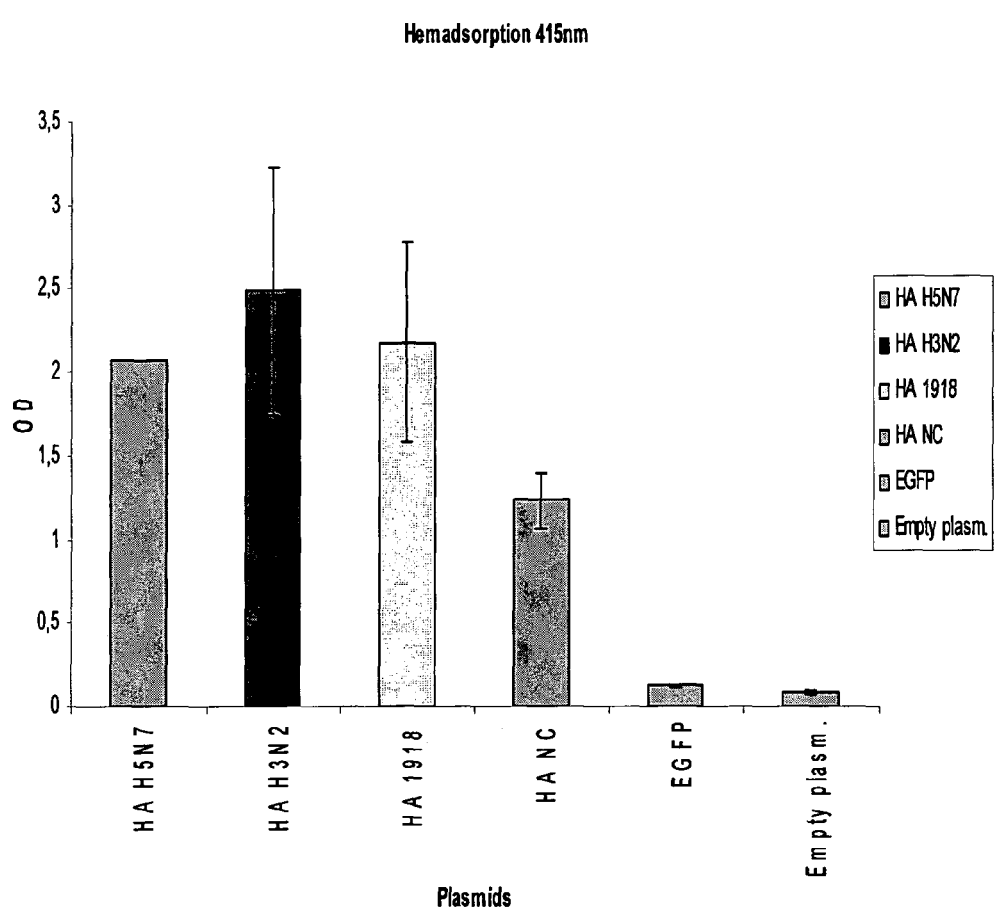

FIG. 4: Hemadsorption as a measure of functional protein expression in mammalian cells of codon optimized HA from 1918 H1N1 (HA 1918), avian H5N7 (HA H5N7) and 1968 H3N2 (HA H3N2) compared to non-codon optimized 1918 H1N1 (HA NC).

Figure 5:
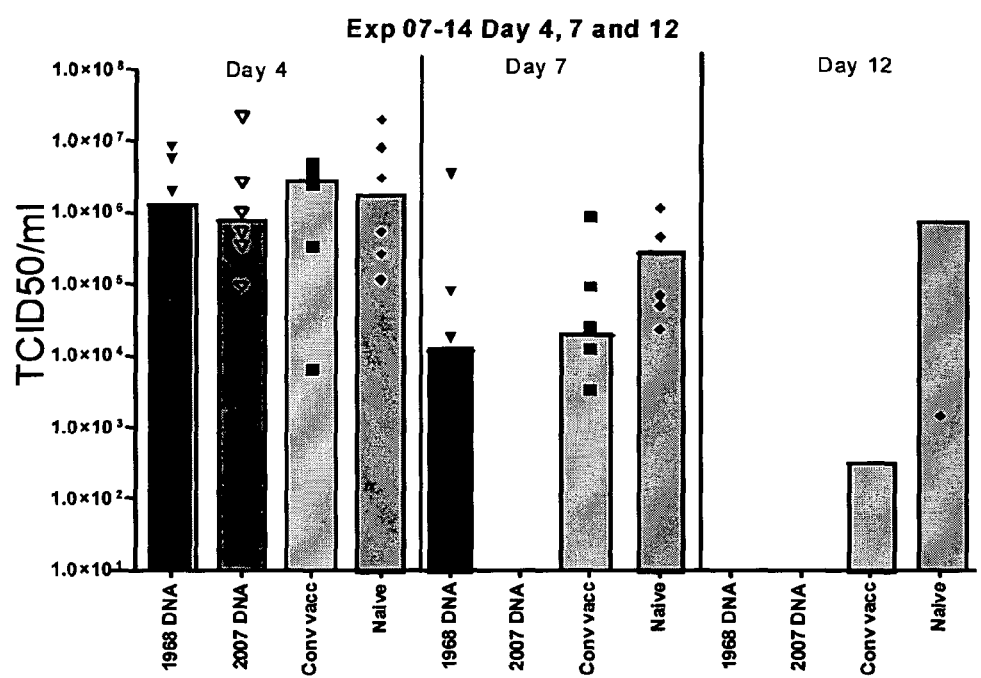

FIG. 5: H3N2 2007/08 virus titre in nasal washings from ferrets vaccinated with either 1968 H3N2 DNA or 2005 H3N2 DNA (circulating sesong 2007/8)

Figure 6:
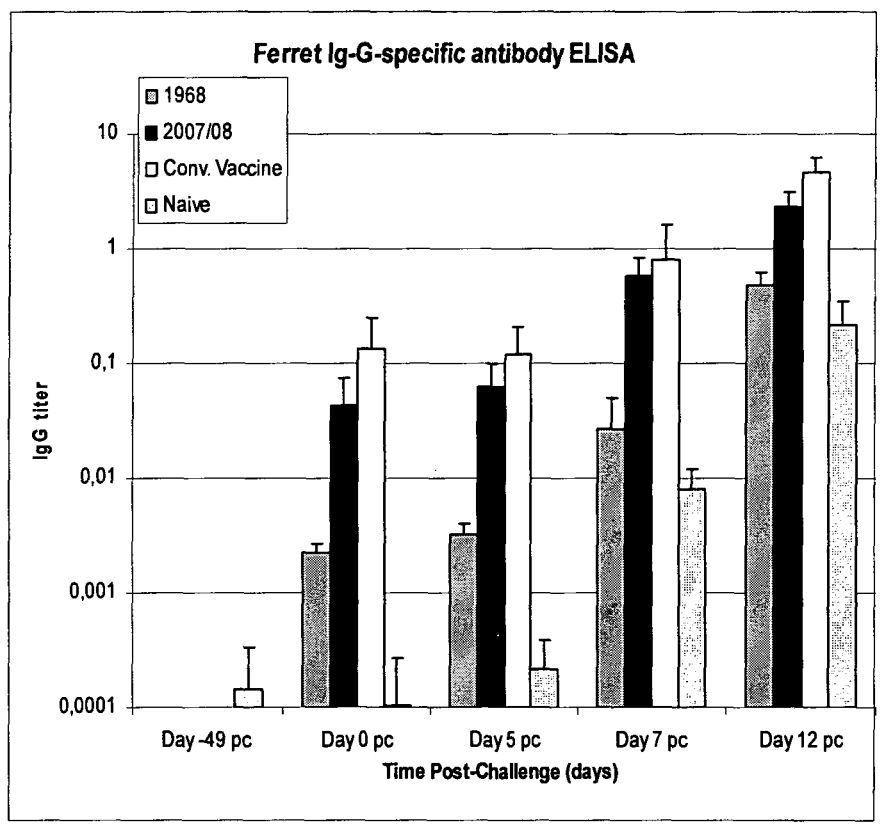

FIG. 6: H3N2 2007/08 influenza A virus specific IgG antibodies in ferret sera post challenge.

Figure 7:
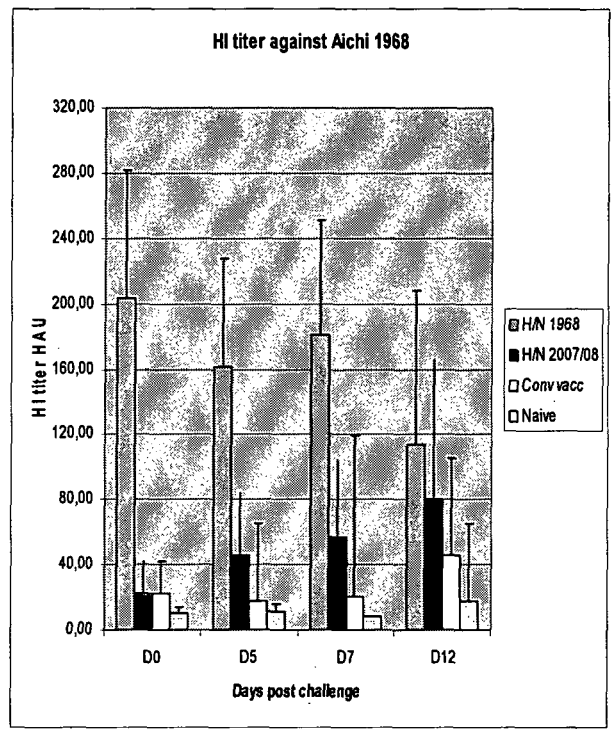
Figure 7:
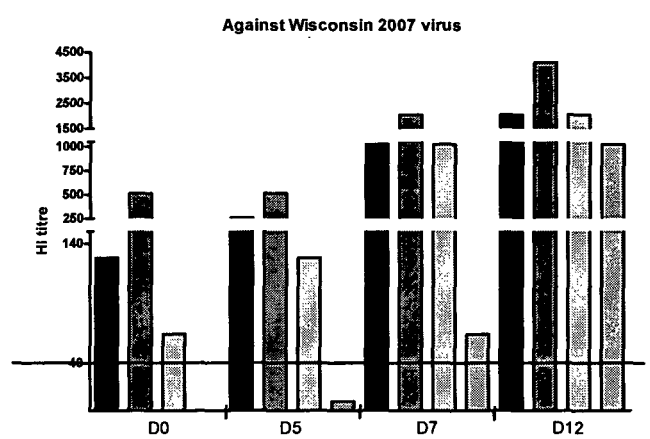

FIG. 7: Haemagglutination inhibition assay against A: 1968 (A/Aichi/2/68) and B: 2007/08 (A/Wisconsin/67/05) H3N2 virus.

Figure 8:
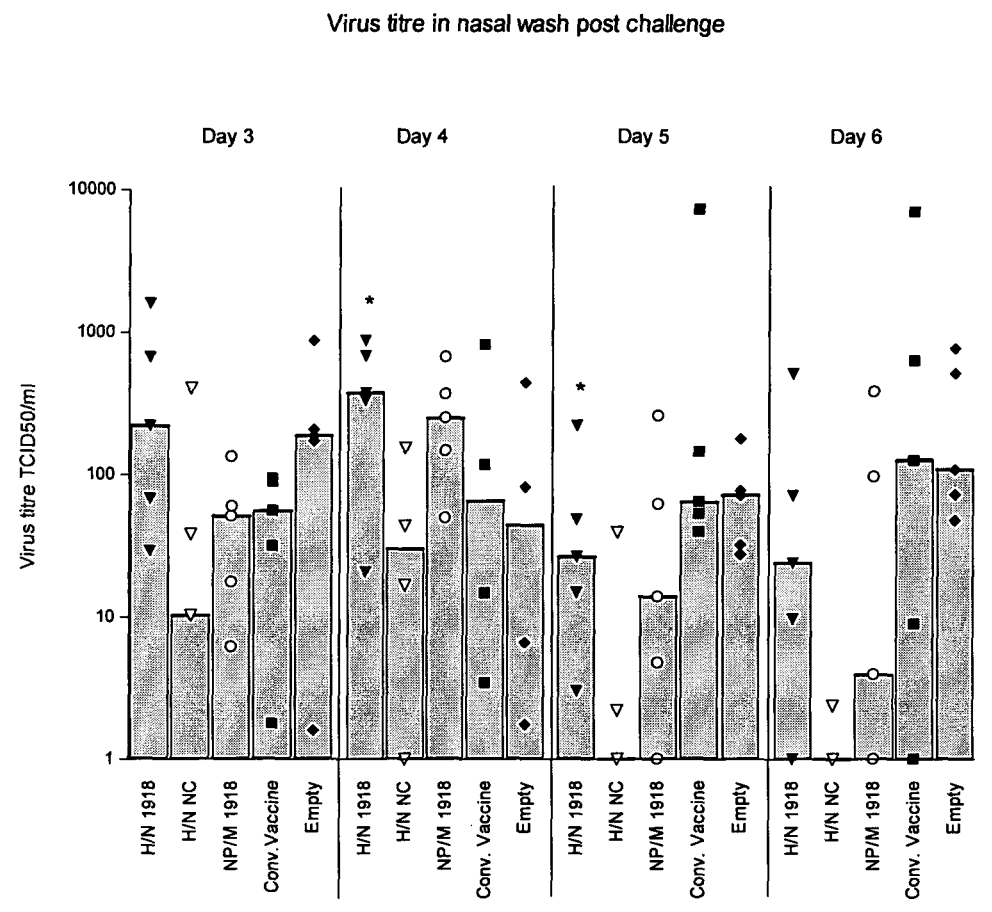

FIG. 8: 2007 H1N1 Virus titer in ferret nasal washings after A/New Calcdonia/20/99 infection.

Figure 9:
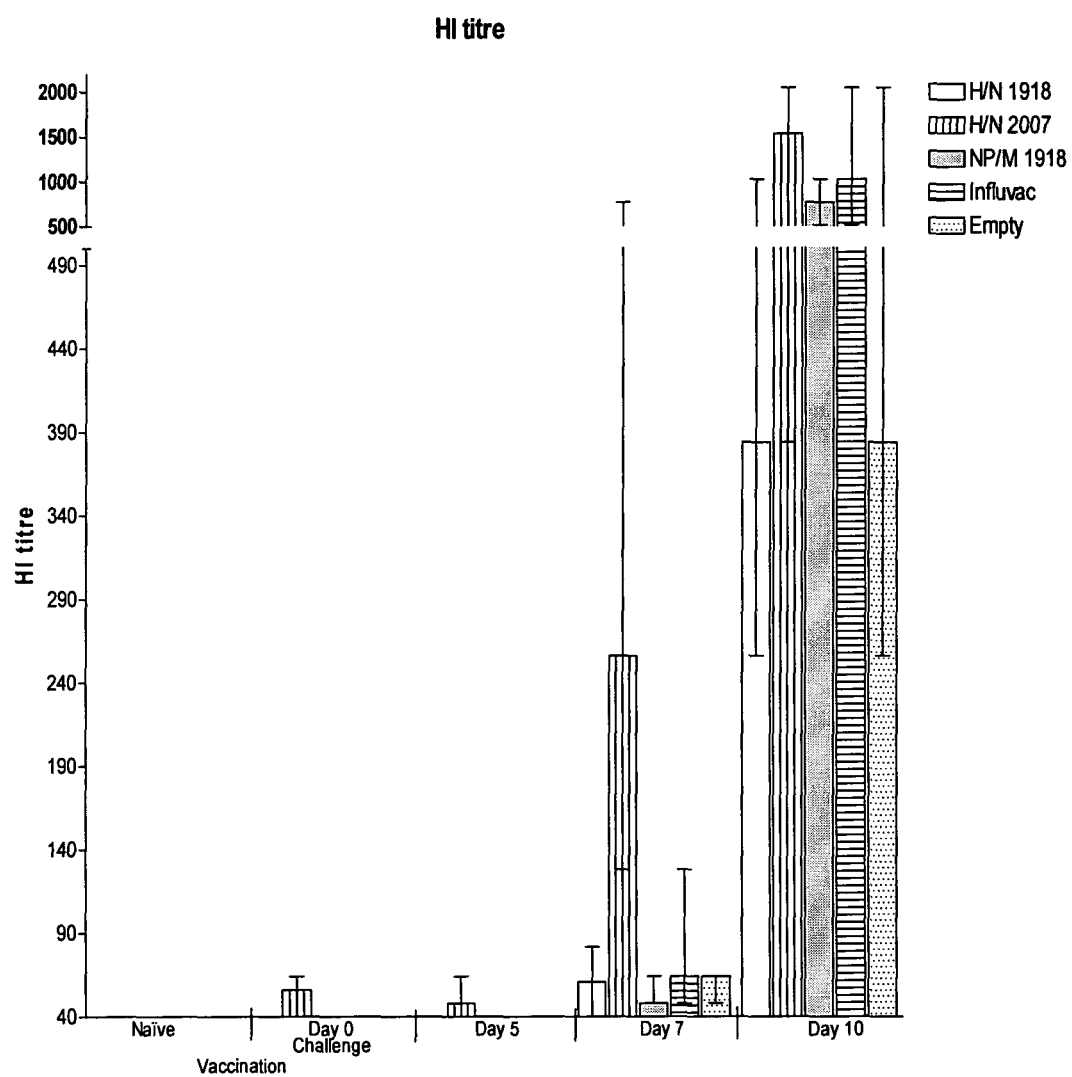

FIG. 9: Haemagglutination inhibition assay against A/new Calcdonia/20/99(H1N1) virus.

Figure 10:
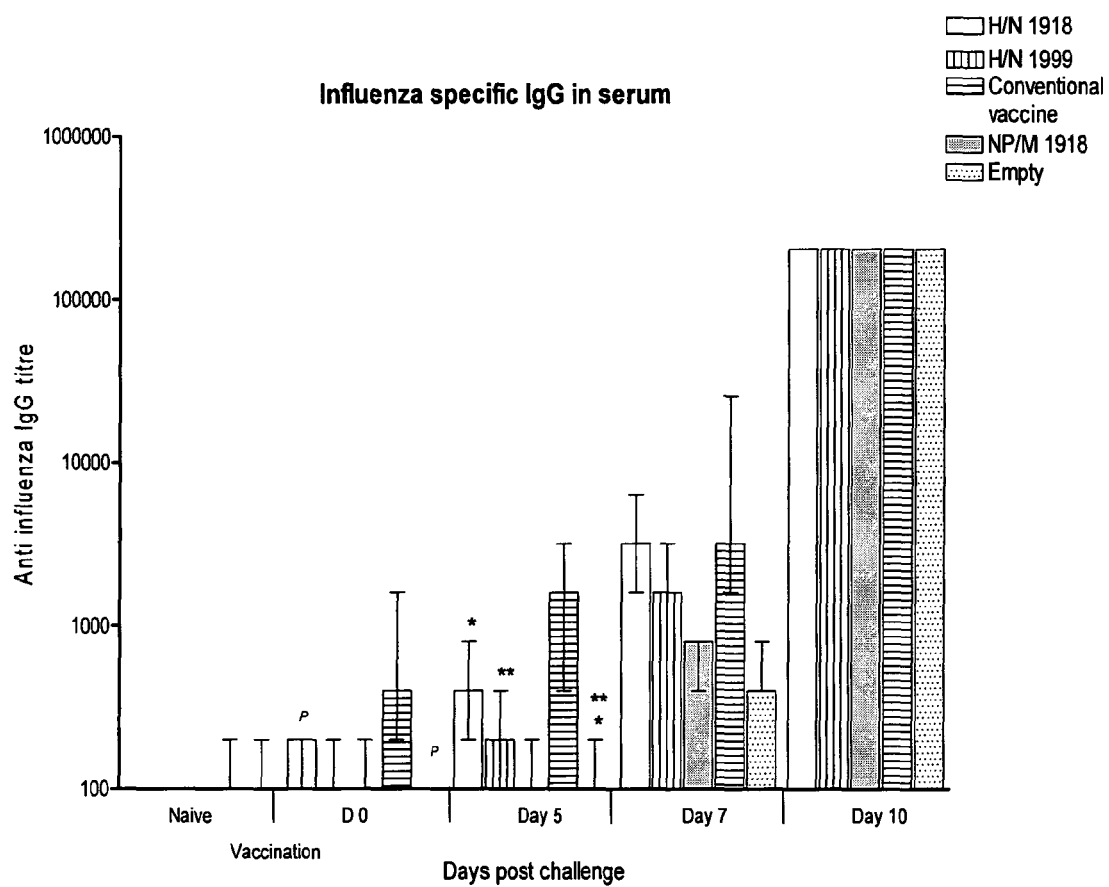

FIG. 10: H1N1 2007 (A/New Calcdonia/20/99 influenza specific IgG antibodies in ferret sera post challenge.

Figure 11:
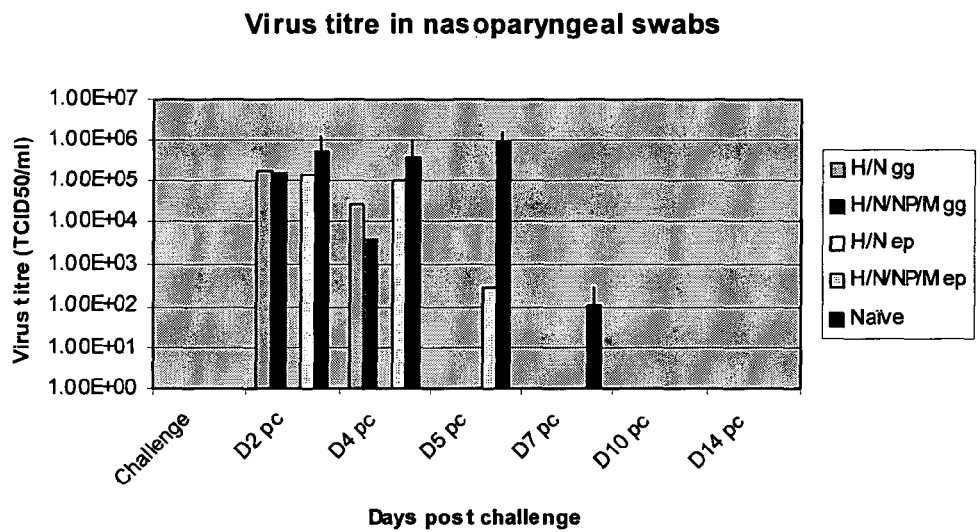

FIG. 11: Pandemic H1N1v DNA vaccine in swine clear seasonal swine h1n1 virus infection Pigs were vaccinated as described in example 15, and TCID50/ml virus was calculated based on a standard curve of known concentrations FIG. 12: Pandemic H1N1v DNA vaccine in swine induce haemagglutination inhibitory antibodies that is triggered by seasonal swine H1N1 virus from 1993.

Figure 13:
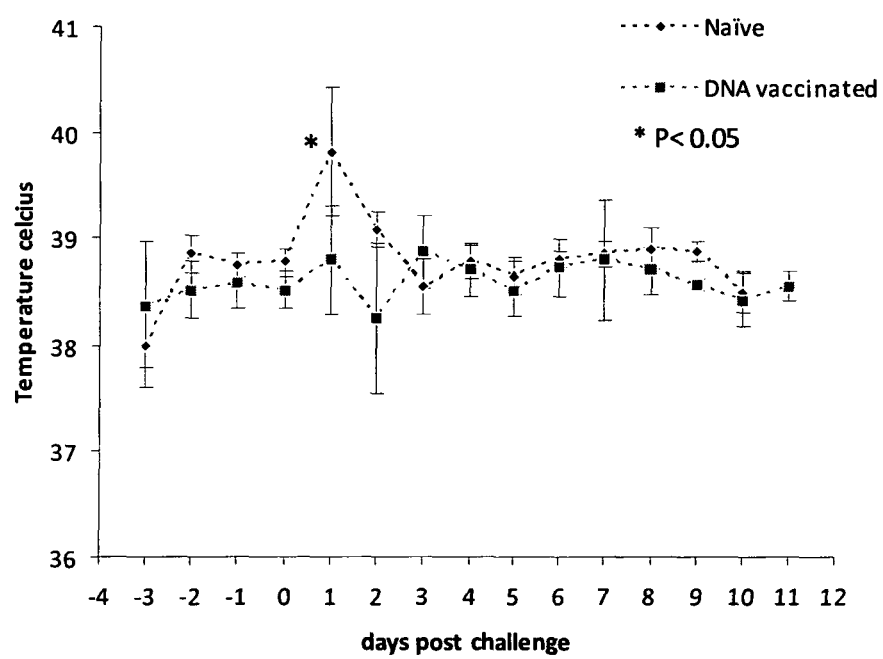

HI antibodies against the pandemic human H1N1v 2009 was measured as described for the ferret studies in example 4b FIG. 13: Pandemic H1N1v DNA vaccine in swine prevent fever after challenge with a seasonal swine H1N1 virus from 1993.

Fever after infection with A/Swine/Denmark/19126/93 (H1N1) virus was measured everyday post challenge.

EXAMPLES

Example 1: Construction of Expression Vectors

Influenza DNA vaccine genes were designed from nucleotide sequences published in GenBank (Table 1) The genes were made synthetically and designed to include the appropriate restriction enzymes and Kozak sequence (GCCACC), −1 base upstream from the start codon, for efficient cloning and transcription in the WRG7079 expression vector (PowderJect, Madison, Wis.). The genes were synthesised using only codons from highly expressed human/ferret genes 5 (codon optimised). By this the nucleotide codons are altered (humanised), but the encoded amino acids are identical to those encoded by the viral RNA. The genes were further cloned individually into the WRG7079 expression vector or the pKCMV vector. Key elements in the expression vectors are a kanamycin resistance gene, cytomegalovirus immediate-early promotor, intron A, and polyadenylation signal. The tissue plasminogen activator (tPA) signal sequence in the original WRG7079 expression vector, used to target proteins to a secretory pathway, was excised in favour of the influenza signal sequence located in the 1918 HA and NA genes. We wanted to apply the same vector for expression of also the internal genes NP and M1 that do not have secretory signals and which are naturally located inside the virus and inside the infected cells, therefore the tPA secretory signal of the WRG7079 was removed.

Genes from the A/New Caledonia/20/99(H1N1) virus applied in the first line of experiments was not designed synthetically or codon optimized. Viral RNA from the A/New Caledonia/20/99(H1N1) MDCK cell cultivated virus was isolated by QIAamp® Viral RNA Mini Kit (QIAGEN, Hilden, Germany) and RT-PCR was performed as previously described 2 by OneStep® RT-PCR Kit (QIAGEN). The primers were designed to amplify the coding gene of HA and NA. The same restriction sites and Kozak sequence were included in the primers as for the 1918 H1N1 constructs (HA NC F: 5'-caacgcgtgccaccatgaaagcaaaactactgg-3' (SEQ ID NO: 26), HA NC R: 5'-tcggcgcctcagatgcatattctacactgc-3' (SEQ ID NO: 27), NA NC F: 5'-caacgcgtgccaccatgaatc-caaatc-3' (SEQ ID NO: 28), NA NC R: 5'-tcg gcgccctactt-gtcaatggtgaacggc-3' (SEQ ID NO: 29)). The RT-PCR products were purified from an agarose gel by the GFX™ PCR DNA and Gel Band Purification Kit (Amersham Biosciences, Piscataway, USA) prior to sequencing. Purified PCR products were sequenced directly. The sequencing reaction was performed by ABI PRISM® BigDye™ Terminators v3.1 Cycle Sequencing Kit (Applied Biosystems, Foster City, Calif., USA) as described previously (2). The development of the sequences was performed on an automatic ABI PRISM® 3130 genetic analyzer (Applied Biosystems) with 80 cm capillaries. Consensus sequences were generated in SeqScape® Software v2.5 (Applied Biosystems). Sequence assembly, multiple alignment and alignment trimming were performed with the BioEdit software v.7.0.5 9. The PCR products were further restriction enzyme digested and cloned into the WRG7079 expression vector in DH5α bacteria. Endotoxin free DNA purification of the vaccine clones were prepared by EndoFree Plasmid Giga Kit (QIA-GEN). All inserts and vaccine clones were control sequenced.

Example 2: Immunizations and Challenge

In the first line of H1N1 DNA vaccine experiments the ferrets (*Mustela Putorius Furo*), approximately seven months old, were divided in groups by using a chip-tag identification for dogs (E-vet, pet-id, Haderslev, Denmark), five to six animals in each group. All animals were kept together and fed a standard diet with food and water ad libitum. The animals were housed according to the Danish Animal Experimentation Act and kept at level II biosecurity facilities at the Faculty of Life Sciences, Copenhagen. The acclimatisation period was nine days.

Four groups of six ferrets were vaccinated as follows; (1) HA (codon optimised gene) and NA (codon optimised gene) 1918 H1N1 plasmid DNA vaccinated, (2) HA, NA, NP and M (all codon optimised) 1918 H1N1 plasmid DNA vaccinated, (3) empty plasmid vaccinated (negative vaccine control) and (4) HA and NA (not codon optimised) A/New Calcdonia/20/99(H1N1) plasmid DNA vaccinated (positive vaccine control). Ferrets were challenged with $1 \times 10^7$ $TCID_{50}$ A/Fourth Mounth/1/47(H1N1) virus.

To investigate the protection against challenge with a contemporary H1N1 virus in comparison with the conventional vaccine in a second experiment, five groups of five animals were vaccinated as follows: (1) HA and NA 1918 H1N1 DNA vaccinated, (2) HA and NA A/New Calcdonia/20/99(H1N1) DNA vaccinated, (3) NP and M 1918 H1N1 DNA vaccinated, (4) conventional trivalent protein vaccine (Influvac, Solvay Pharmaceuticals), (5) empty plasmid vaccinated (negative vaccine control). These animals received two shots of DNA vaccine for each vaccination and were challenged with $1 \times 10^7$ $TCID_{50}$ A/New Calcdonia/20/99

To compare the protection of 1918 DNA vaccinated ferrets with naïve untreated ferrets in the third experiment, two groups of five animals were vaccinated as follows: (1) HA and NA 1918 H1N1 DNA vaccinated, (2) Unvaccinated naïve animals. The DNA vaccinated animals in this experiment received four shots of DNA vaccine for each vaccination. The ferrets were challenged with $1 \times 10^7$ $TCID_{50}$ A/New Calcdonia/20/99

To evaluate the H3N2 pandemic DNA vaccine against present time H3N2 viruses ferrets were divided into four groups, six animals in each group. The groups were vaccinated as follows: (1) HA and NA 1968 H3N2 DNA vaccine (2) HA and NA 2007/08 H3N2 DNA vaccine (A/Wisconsin/67/05(H3N2), (3) conventional trivalent protein vaccine (Influvac), (4) Unvaccinated naïve animals. The DNA vaccinated animals in this experiment received four shots of DNA vaccine for each vaccination and were challenged with $1 \times 10^7$ $TCID_{50}$ A/Wisconsin/67/05(H3N2).

HA and NA DNA mixed vaccines were given in two shots and NP and M DNA mixed vaccines were given in two shots. Therefore groups receiving only HA and NA DNA vaccine were additionally shot twice with empty plasmid DNA, ensuring that all animals had received the same amount of DNA and the same number of shots.

The ferrets were gene gun (Helios, Bio-Rad, Hercules, Calif.) inoculated (400 psi compressed helium) on shaved abdominal skin, using 2 μg plasmid DNA-coated gold particles (1.6 μm-sized particles), 80-95% coating efficiency each shot. Each ferret received four shots, three times biweekly. Ferrets were challenged 10-14 days after third immunisation by $\sim 1 \times 10^7$ TCID50/ml of either A/Fouth Mounth/1/47 (H1N1), A/New Calcdonia/20/99(H1N1), or A/Wisconsin/65/2005(H3N2) virus in 100 μl PBS administrated into the nostrils with a syringe. Blood serum was collected sequentially post-challenge from vena cava of anesthetised animals (tiletamine/zolazepam (zoletil-mix for cats)). Animals were terminated with pentobarbital.

Example 3: Quantitative Real Time RT-PCR Assay for Influenza a Virus

At the day of blood serum collection the nostrils of each ferret were flushed with 1 ml PBS and the flushing were frozen down immediately for real-time RT-PCR analysis. Two hundred micro liters of nasal wash were extracted on an automated MagNA Pure LC Instrument applying the MagNa Pure LC Total Nucleic Acid Isolation Kit (Roche diagnostics, Basel, Switzerland). The extracted material was eluated in 200 μl Milli-Q H2O. The RT-PCR reactions were performed with oligonucleotide sequences as described by Spackman et al., (23). Extracted material (5 μl) was added to 20 μl of master mix consisting of 10 nM of each primer and 2 nM of the Taqman probe labelled with FAM in the 5' end and black hole quencher 1 in the 3' end together with reagents from the OneStep® RT-PCR Kit (QIAGEN, Hilden, Germany) according to the manufacturer. Target sequences were amplified on the MX3005 system from Stratagene with the following program: 20 min 50° C., 15 min 95° C. and 40 cycles of 15 sec 95° C. and 60 sec at 55° C. The content of viral genomes in the samples was determined using a standard curve developed by amplifying dilution of H1N1 or H3N2 virus with known concentration.

Example 4: Serum Antibody Determined by ELISA

ELISA plates (96 wells) were coated with 100 μl, split influenza vaccine (Vaxigrip 2007-08, or Influvac 2006-07) diluted 1:100 in 35 mM NaHCO3 pH 9.6 and 15 mM Na2CO3 over night at 4° C. Wells were blocked with 1% PBS/BSA for 30 minutes at room temperature. Plates were washed with 0.05% PBS/tween (PBST). Sera 1:100 were diluted in 0.1% BSA/PBST two-folds in the plate and incubated for one hour at room temperature. The plates were washed and incubated with 100 μl biotinylated rabbit anti-ferret IgG diluted 1:250 for one hour in room temperature, washed, and incubated with 100 μl 1:1,000 horseradish peroxidase (HRP) streptavidin (DakoCytomation, Glostrup, Denmark). After 30 minutes the plates were washed and 100 μl of hydrogen peroxide with OPD was added. The reaction was stopped by adding 50 μl 0.5 M $H_2SO_4$ and read at OD492 nm.

Example 4C: Haemagglutination Inhibition Assay

Ferret sera were treated with receptor destroying enzyme (RDE(II), Seiken, Japan) as described in by the manufacturer. One part of ferret serum was blood-absorbed by 20 parts of packed guinea pig red blood cells and incubated for one hour at 4° C. followed by centrifugation. Viruses were titrated by a haemagglutination assay according to the protocols of the WHO [9] with 0.75% guinea pig red blood cells in U-bottom plates (U96 MicroWell Plates, Nunc) and incubated for one hour. Virus was standardised to 100% haemagglutination endpoint titre of 8 haemagglutination units (HAU). The haemagglutination inhibition (HI) assay was performed according to the protocols of WHO [9] with 0.75% guinea pig red blood cells in U-bottom 96 well plates (U96 MicroWell Plates, Nunc) and the HI titres read as the reciprocal of the last dilution of sera that completely inhibits haemagglutination.

Example 5: Results from Influenza Challenged Ferrets Receiving Our Initial H1N1 Influenza DNA Vaccines in Ferrets Ferrets were negative for influenza specific antibodies seven days before start of immunisations as measured by ELISA.

High IgG specific serum antibodies (to A/New Calcdonia/20/99(H1N1) in ELISA) were observed at day seven post-challenge in ferrets vaccinated with both HA+NA 1918 (two plasmids) and HA+NA+NP+M 1918 DNA vaccines (four plasmids) (FIG. 2) but challenged with a virus from 1947. Ferrets vaccinated with HA+NA DNA A/New Calcdonia/20/99(H1N1) induced lower specific serum antibody titre on day seven. It is possible that a higher antibody response could have been observed at later time points if the experiment had not been terminated at day seven after challenge for practical reasons.

At day five post-challenge the ferrets vaccinated with empty plasmid (negative vaccine control) showed high viral load in nasal washing measured as viral RNA copies in the nasal washings, indicating no protection against the viral challenge. However, ferrets vaccinated with HA+NA 1918 and HA+NA, NP+M 1918 DNA vaccines were completely protected from infection with a A/Forth Mounth/1/47 (H1N1) virus (FIG. 2). Partial protection was observed in ferrets vaccinated with HA+NA A/New Calcdonia/20/99 (H1N1) DNA plasmids.

The data clearly show that DNA immunisations based on genes from the 1918 H1N1 pandemic strain induce strong specific antibody response and protect ferrets completely against infection with a H1N1 strain from 1947. Thus challenge with a drifted influenza H1N1 virus trigger recognition of antibodies generated by a heterologous virus based DNA vaccine. The 1918 genes indused full protection against the 1947 strain, while the 1999 genes were slightly less efficient. No negative or positive effects on the humoral immune response or protection was observed by including the NP and M 1918 genes in the HA+NA DNA vaccination since the protection from infection already was nearly 100%.

Example 6: Second H1N1 Influenza DNA Vaccine Experiment in Ferrets; Challenge with A/New Calcdonia/20/99 (H1N1) Virus We compared conventional protein H1N1 split vaccine (two immunizations) versus 1918 H1N1 HA and NA codon optimized DNA vaccine versus codon optimized New Calcdonia H1N1 HA and NA versus codon optimized M and NP from 1918 H1N1 virus, versus empty DNA vaccine vector using three immunizations. Ferrets were challenged with A/New Calcdonia/20/99(H1N1) virus intra nasally and virus quantitated in nasal washings by real-time RT/PCR assay as in example 3.

Ferret antibodies are examined for ELISA antibodies and HI antibody as described in examples 4 and 4c.

Example 7: Mouse Antibody Experiments

Codon optimized versus non-codon optimized HA and NA DNA vaccines from New Calidonia H1N1 (shows the difference between codon optimization and non-optimization) versus codon optimized HA and NA from 1918 H1N1 strain is inoculated in mice. Antibody titers and epitope mapping of induced antibodies is done by overlapping peptides in ELISA and cross-reactions measured to other influenza A virus.

Example 8: Protein Expression Experiments

Codon optimized versus non-codon optimized HA and NA DNA vaccines from New Calidonia H1N1 (shows the difference between codon optimization and non-optimization) versus codon optimized HA and NA from 1918 H1N1 strain is expressed in mammalian cell lines in vitro and standard radio immuno precipitation (RIPA) are done with polyclonal influenza A antibodies to examine the improved protein expression obtained by codon optimization.

Example 9: Cytokine Induction Experiments

Codon optimized versus non-codon optimized HA and NA DNA vaccines from New Calidonia H1N1 (shows the difference between codon optimization and non-optimization) versus codon optimized HA and NA from 1918 H1N1 strain is added onto mammalian peripheral blood monocytes (PBMCs) in vitro and measurements of resulting cytokine production is measured in the cell supernatant to examine the innate immune induction (adjuvant effect) obtained by codon optimization and by the codon optimised H1N1 1918 HA and NA as compared to the codon optimised H1N1 New Calcdonia HA and NA to examine special cytokine induction by the 1918 genes.

Example 10: 1918 HA and NA Protein Vaccine Experiments

Proteins are produced by the DNA vaccine plasmids and used as a protein vaccine in mice or ferrets as compared to DNA vaccination and to traditional protein split vaccine to measure the immune induction of 1918 proteins versus DNA vaccine.

Example 11: Mouse DNA Vaccine Delivery Experiments

Codon optimized HA and/or NA DNA vaccines from 1918 H1N1 strain is inoculated in mice as expression plasmids or as a linear piece of DNA containing the necessary components for vaccine gene expression but without the rest of the plasmid to rule out any effect of the rest of the plasmid.

Example 12: Pig DNA Vaccine Delivery Experiments

Codon optimized HA and/or NA DNA vaccines from 1918 H1N1 strain is inoculated in pigs as expression plasmids or PCR products (from example 14) and challenged with a present day New Calcdonia-like H1N1 strain and protection against disease and immune induction are measured. Thus the H1N1, H2N2 and/or H3N2 DNA vaccines may be applied in pigs that are susceptible to human influenza A pathogenic viruses.

Example 13: Results of Second H1N1 DNA Vaccine Experiment in Ferrets Compared to Conventional Vaccine In the second experiment (Example 6) the efficiency of the 1918 DNA vaccine induced protection against a nearly 90 year drifted virus, A/New Calcdonia/20/99(H1N1), was evaluated. The protection was compared against the protection induced by the conventional trivalent protein vaccine from 2006-2007 for which A/New Calcdonia/20/99 was one of the three vaccine components. The ability of the different vaccines to prevent infection or clearance of virus infection was measured by influenza A virus titres in nasal washings of to ten days after challenge.

Low virus titre levels were measured for all vaccinated groups; however, all DNA vaccinated groups had a reduction in virus titre throughout the infection, and the HA+NA 1918 DNA vaccinated group had a significant (P<0.05) reduction in virus titre from day four to day five post challenge with A/New Calcdonia/20/99 (FIG. 8). The HA+NA A/New Calcdonia/20/99 (H/N NC) DNA vaccine was the most effective vaccine in preventing A/New Calcdonia/20/99(H1N1) virus infection and virus clearance. 1918 DNA vaccine with the internal proteins M and NP alone seemed more effective than the HA+NA 1918 DNA vaccine in providing cross-protection against the extremely drifted virus challenge. Interestingly, no significant change in virus titre from day three to day six was observed for the group vaccinated with the conventional protein vaccine or the empty plasmid (FIG. 8). The negative control group vaccinated with empty plasmid had virus infection still at day seven (below cut-off value 10 TCID50/mL) and one animal in the conventional vaccine group still possessed high virus titer at day 7. By day ten no virus could be detected in any groups (not shown).

The third experiment comparing HA+NA 1918 DNA vaccinated ferrets with naïve, unvaccinated, ferrets showed similar high levels of virus titre for both groups until day 6. However, at day 7 post infection the HA+NA 1918 DNA vaccinated ferrets had more efficient reduction in virus titre (P=0.13) compared to the naïve ferrets (P=0.18) and a lower virus load at day seven compared to the naïve group (P=0.61). Only three of five ferrets in the 1918 DNA vaccinated group had detectable virus load at day seven compared to five of five animals in the naïve group (FIG. 3c). DNA vaccinated ferrets also showed lower rive in body temperature than unvaccinated ferrets (FIG. 3a) and also scored less on clinical symptoms compared to the naïve ferrets (FIG. 3c). There were no difference in weight loss (FIG. 3b)

Influenza Specific Antibody Response after DNA Vaccination

A significant higher influenza A IgG titer (example 4) compared to the negative control group was observed at the day of challenge for the H/N 1918 DNA vaccinated ferrets, indicating induction of influenza specific antibodies after DNA vaccination (FIG. 10). At day five post infection, both H/N 1918 and H/N 1999 DNA vaccinated animals and conventional vaccine vaccinated animals showed vaccine induced influenza specific antibodies (FIG. 10). The H/N 1918 DNA vaccinated animals had comparable recall antibody titre to the conventional vaccine vaccinated animals at day seven post infection (FIG. 10). Influenza specific antibodies for the NP/M 1918 DNA vaccinated group was not expected measured in this ELISA assay pre-challenge due to the use of conventional influenza vaccine as antigen.

Induction of Naturalising Antibodies after DNA Vaccination

Haemagglutination inhibition assay (example 4b) correlates with virus neutralisation assay and measures how well sera from vaccinated animals inactivate influenza virus binding of red blood cells. Only ferrets vaccinated with the H/N 1999 H1N1 DNA vaccine had significant HI titre against the A/New Calcdonia/20/99(H1N1) virus after DNA vaccination at the day of challenge (FIG. 9). Neither H/N 1918 nor NP/M 1918 were expected to give titres before infection due to the long drift and accumulation of mutations at the HA receptor-binding site between the 1918 and 1999 H1N1 viruses. Antibodies against NP or M are not neutralising. The H/N 1999 DNA vaccine gave a better recall response of neutralising antibodies than the conventional trivalent protein vaccine (FIG. 9). At day five after infection 60% of the H/N 1999 H1N1 DNA vaccinated ferrets had seroconverted (HI>40), compared to 40% of the ferrets in the conventional vaccine group. Also a >2.5 fold increase in HI MGT was accomplished after vaccination measured the day of challenge (FIG. 9).

Example 14: Results Pandemic H3N2 DNA Vaccine in Ferrets

To prove the principle of broad cross reactivity obtained by using particularly the pandemic surface proteins as DNA vaccines we evaluated the protection against contemporary H3N2 virus challenge after vaccination with codon optimised HA and NA from the 1968 H3N2 pandemic Hong Flu flu as DNA vaccine in ferrets.

Ferrets were vaccinated (Example 2) with gene gun (PMED) three times, two weeks apart, with HA+NA DNA vaccine based on either 1968 virus or 2007/08 virus (A/Wisconsin/67/05(H3N2)). Control groups were vaccinated twice, three weeks apart, with the conventional trivalent protein vaccine. The negative control group did not receive any vaccination prior to challenge. All ferrets were challenged two weeks after the last vaccination.

Ferrets nostrils were flushed post challenge with 1 ml PBS and washings were stored immediately at −80° C. Virus titre were measured by real-time RT-PCR (Example 3) on the matrix gene of influenza A and correlated against a standard curve of known H3N2 2007/08 virus TCID50/ml in MDCK cells. DNA vaccinated groups had reduction in virus titre during virus incubation not observed for the control groups. Only the conventional vaccinated ferrets and the non-vaccinated ferrets had virus titre present at day 12 post infection (FIG. 5).

Ferret blood was collected at different time points post challenge and sera was analysed for H3N2 2007/08 influenza virus specific IgG antibodies by ELISA (Example 4). The DNA vaccines induced 2007/08 influenza virus specific IgG in sera after vaccination as did the conventional vaccine (FIG. 6). The 1968 DNA vaccinated ferrets generated high cross reactive antibodies against the contemporary challenge virus A/Wisconsin/67/05(H3N2). The response directed against the challenge virus can not be seen before day 7 in the naïve group. The level of influenza specific antibodies in the 2007/08 HA+NA DNA vaccinated group is comparable to the level observed for the conventional vaccine group.

Blood sera collected at different time points post challenge were measured for A/Aichi/2/68 and A/Wisconsin/67/05 H3N2 virus haemagglutination inhibitory (HI) antibodies by a HI assay (Example 4b). Titres were measured as the last sera dilution giving 100% inhibition of 4 haemagglutination units (HAU) virus in 25 µl (FIG. 7).

A) High sera HI titres against 1968 virus after HA+NA 1968 DNA vaccination were observed. The antibodies generated after HA+NA 2007/08 DNA or conventional vaccine could not cross react with the 1968 virus. B) High cross reactive HI titres against 2007/08 virus in pools after 1968 DNA vaccination was observed. The 2007/08 DNA vaccinated ferrets had higher HI antibodies against 2007/08 virus after vaccination than ferrets immunised with the 2007/08 conventional trivalent protein vaccine.

Vaccination with 1968 H3N2 HA induced protection against both 1968 and drifted H3N2 virus strain from more present day (2007).

Example 15: Pandemic H1N1v1 Influenza DNA Vaccine in Swine

Pigs and ferrets was vaccinated with the DNA vaccine mix containing HA and NA encoding plasmids from H1N1v with or without DNA plasmids encoding M and NP from H1N1 1918 with or without DNA plasmids encoding HA and NA from an seasonal H3N2 strain (A/Wisconsin/67/05) using the synthesised genes with human preferred codons for high expression in humans, ferrets and swine. Haemagglutinin Inhibition (HI) titre levels and/or neutralising antibody titres and/or total IgG antibodies and/or protection against heterologous or homologous virus challenge as measured by faster virus clearance in respiratory tract after one or two DNA immunisations was evaluated (example 3, 4 and 4b).

To assess the cross-protective immunity in swine after vaccination with influenza DNA vaccine based on the HA and NA genes of the new 2009 pandemic H1N1v virus with or without the NP and M genes of the pandemic 1918 H1N1 virus either delivered with gene gun or by electroporation we vaccinated four 6 weeks old pigs, twice, three weeks apart and challenged 10 weeks after last immunisation with a seasonal swine H1N1 virus (A/swine/Denmark/19126/93) $1\times10^7$ EID$_{50}$. Four pigs was included as naïve animals, not receiving vaccination.

One pig vaccinated with gene gun received both HA and NA H1N1v beads and NP and M 1918 H1N1 beads. The other animal in the gene gun group received a double dose of HA and NA H1N1v beads.

One pig vaccinated with electroporation received both HA and NA 2009 H1N1v DNA injections and NP and M 1918 H1N1 DNA injections, while the other pig in the electroporation group received double injections of HA and NA 2009 H1N1v DNA.

The pigs were vaccinated as follows:
Three Groups:

| | | |
|---|---|---|
| Gr1 | Gene Gun | |
| Gr2 | Electroporation | |
| Gr3 | Naïve unvaccinated | |

Details for Vaccination of Group 1 and 2:

| | | |
|---|---|---|
| | Gene Gun Group 1 | |
| Pig 1 | HA + NA H1N1v beads | |
| | Dorsal side of each ear: two shots | |
| | Inner side of each thigh: two shots | |
| | NP + M 1918 | |
| | Dorsal side of each ear: two shots | |
| | Inner side of each thigh: two shots | |
| Pig 2 | HA + NA H1N1v beads | |
| | Dorsal side of each ear: four shots | |
| | Inner side of each thigh: four shots | |
| | Electroporation Group 2 | |
| Pig 3 | HA H1N1v | |
| | Dorsal side of each ear: One injections 50 µl, one pulse | |
| | Inner side of each thigh: One injections 50 µl, one pulse | |
| | NA H1N1v | |
| | Dorsal side of each ear: One injections 50 µl, one pulse | |
| | Inner side of each thigh: One injections 50 µl, one pulse | |
| | NP 1918 | |
| | Dorsal side of each ear: One injections 50 µl, one pulse | |
| | Inner side of each thigh: One injections 50 µl, one pulse | |
| | M 1918 | |
| | Dorsal side of each ear: One injections 50 µl, one pulse | |
| | Inner side of each thigh: One injections 50 µl, one pulse | |
| Pig 4 | HA H1N1v | |
| | Dorsal side of each ear: two injections 50 µl, one pulse | |
| | Inner side of each thigh: two injections 50 µl, one pulse | |
| | NA H1N1v | |
| | Dorsal side of each ear: two injections 50 µl, one pulse | |
| | Inner side of each thigh: two injections 50 µl, one pulse | |

Immunisations:

Gene Gun Vaccination:

Helium pressure: ~420 psi

One shot ~2 ug DNA

Pig1 receives a total of 16 shots

Pig2 receives a total of 16 shots $1^{st}$ vaccination day 0

$2^{nd}$ vaccination day 21

Electroporation

Settings:

0.2 A, one pulse (several pulses in one pulsing), 52 ms/pulse, One injection contains 50 µl of 2 ug/µl DNA (100 ug DNA in one injection).

Pig 3 receives 16 injections and 16 pulses

Pig 4 receives 16 injections and 16 pulses $1^{st}$ vaccination day 0

$2^{nd}$ vaccination day 21

All groups were challenged 10 weeks after last immunisation with $1\times10^7$ TCID50 seasonal A/swine/Denmark/19126/93(H1N1) virus.

Samplings: Blood and nasopharyngeal swabs were collected sequentially after challenge and the animals were euthanized 14 days after challenge Results Virus Titre in Nasopharyngeal Swabs:

All DNA vaccinated pigs were able to clear the heterologous virus challenge more efficiently than the naïve pigs not receiving vaccine (FIG. 11). The only vaccine able to prevent infection was HA and NA H1N1v DNA administrated by electroporation.

Cross-Reactive Haemagglutination Inhibition of Pandemic H1N1v Virus

Figure 12:
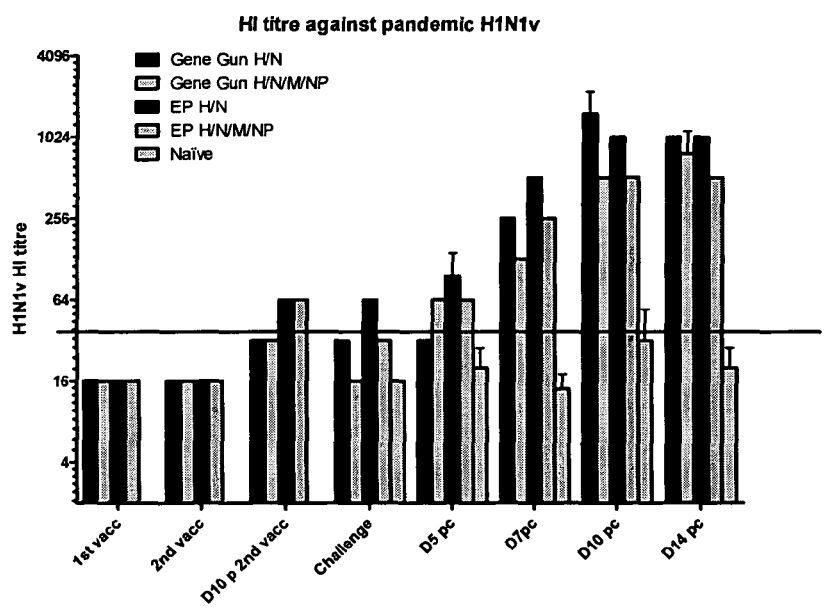

HA and NA H1N1v DNA vaccine administrated by electroporation were able to induce an HI tire against the H1N1v above 40, 10 days after second vaccination (FIG. 12). The pig was able to maintain the titre 10 weeks after second vaccination. All DNA vaccinated pigs demonstrated significant cross-reactive HI antibodies against the H1N1v virus from five days after challenge with the heterologous swine seasonal H1N1 virus from 1993. These results indicate that challenge with a different strain than the one comprising the DNA vaccine is able to trigger some common HI antibodies after DNA vaccination, inducing efficient cross reactive HA neutralising antibodies.

Fever

The four pigs immunized with the pandemic H1N1v DNA vaccine did not show rise in body temperature during the infection with the seasonal swine virus from 1993; however, the un-vaccinated pigs did develop fever at day 1 post challenge (FIG. 13).

Example 16: Use of Transcriptionally Active PCR Products from Influenza A as DNA Vaccines Instead of Plasmid DNA PCR products can be obtained using the codon optimised vaccine genes from pandemic influenza A strain transcriptionally active PCR products as template and the PCR products them selves can be used as a DNA vaccine. To be transcritionally functional the PCR products will contains all necessary signal components (promoter, Kozak and terminator) for efficient transcription of a desired influenza gene or partial gene in the host. In this way no plasmid backbone e.g. with antibiotic resistance marker and unnecessary DNA would be needed.

Example 17: DNA Vaccine Encoding Glycosylation-Free Influenza Proteins

Influenza genes are site directed mutated in a plasmid backbone to remove desired N-linked glycosylations at antigenic sites in the HA and NA gene. The desired glycosylations that should be removed are all or some of those that has been added to the pandemic strains during the evolution and drift leading to present day circulating Influenza A strains of H1N1, H2N2, H3N2 types, respectively. Completely glycosylation-stripped proteins can also be produced in this way.

Example 18: Composition of a Universal Influenza DNA Vaccine

A DNA vaccine is composed containing codon optimized genes of influenza H1H1, H3N2 and influenza B: For the H1N1 and H3N2 there should be HA and NA from an original pandemic strain and one contemporary strain e.g. New Calcdonia/20/99(H1N1) and/or Wisconsin/67/05 (H3N2) possibly mutated to express less glycosylated protein. In addition, to obtain even broader cross reactivity, the M and NP genes from pandemic H1N1 should be included. This will result in a trivalent vaccine that will induce long time protection against all H3 and H1 subtypes including most influenza B strains. The universal DNA vaccine could either be a pool of all eleven plasmids or a mix of bicistronic vectors. Alternatively the pandemic vaccine components could be given as DNA vaccine as a prime and the conventional trivalent protein vaccine on the market could serve as a boost. The goal is a vaccine that would work a lifetime, at least seasonal vaccinations would be unnecessary.

Example 19: Universal H1N1 and H3N2 Influenza DNA Vaccine

We have previously demonstrated that different influenza DNA vaccines based on a subtype combination of influenza, e.g. H1N1 or H1N1v or H3N2 are effective in inducing protection against the given subtype of viruses.

However, the optimal influenza vaccine would comprise components of both H1N1 and H3N2. We therefore designed a "universal influenza DNA vaccine" which is based on the HA and NA from the recent pandemic H1N1v, the internal genes NP and M of the previous pandemic H1N1 from 1918, and the HA and NA genes from a seasonal H3N2 virus. This example focus on the "universal influenza DNA vaccine" administrated together with a helper plasmid serving as an adjuvant. If delivered intranasally the flu DNA together with the helper plasmid will be embedded in a lipid-formulation for optimal delivery to the mucus. The immune response induced by the universal influenza DNA vaccine administrated either intranasally or by gene gun or by electroporation will be evaluated in an animal model. The protection and cross protection against homologous and heterologous virus challenge will be investigated.

REFERENCES

1. Antonovics, J., M. E. Hood, and C. H. Baker. 2006. Molecular virology: Was the 1918 flu avian in origin? Nature 440:E9.
2. Bragstad, K., P. H. Jorgensen, K. J. Handberg, S. Mellergaard, S. Corbet, and A. Fomsgaard. 2005. New avian influenza A virus subtype combination H5N7 identified in Danish mallard ducks. Virus. Res. 109:181-190.
2a Bragstad, K., Martel, C M., Jensen K L., Thomsen J S., Nielsen L P., Aasted B. and Fomsgaard A., Pandemic influenza 1918 H1N1 and 1968 H3N2 DNA vaccines induce protective immunity against infection with decades of drifted viruses, submitted 2009.
3. Caton, A. J., G. G. Brownlee, J. W. Yewdell, and W. Gerhard. 1982. The antigenic structure of the influenza virus A/PR/8/34 haemagglutinin (H1 subtype). Cell 31:417-427.
4. Chen, Z., S. e. Kadowaki, Y. Hagiwara, T. Yoshikawa, K. Matsuo, T. Kurata, and S. i. Tamura. 2000. Cross-protection against a lethal influenza virus infection by DNA vaccine to neuraminidase. Vaccine 18:3214-3222.
5. Corbet, S., L. Vinner, D. M. Hougaard, K. Bryder, H. V. Nielsen, C. Nielsen, and A. Fomsgaard. 2000. Construction, biological activity, and immunogenicity of synthetic envelope DNA vaccines based on a primary, CCR5-tropic, early HIV type 1 isolate (BX08) with human codons. AIDS Res. Hum. Retroviruses 16:1997-2008.
6. Davis, H. L., B. A. Demeneix, B. Quantin, J. Coulombe, and R. G. Whalen. 1993. Plasmid DNA is superior to viral vectors for direct gene transfer into adult mouse skeletal muscle. Hum. Gene Ther. 4:733-740.
7. Donnelly, J. J., A. Friedman, D. Martinez, D. L. Montgomery, J. W. Shiver, S. L. Motzel, J. B. Ulmer, and M. A. Liu. 1995. Preclinical efficacy of a prototype DNA vaccine: enhanced protection against antigenic drift in influenza virus. Nat. Med. 1:583-587.
8. Epstein, S. L., W. p. Kong, J. A. Misplon, C. Y. Lo, T. M. Tumpey, L. Xu, and G. J. Nabel. 2005. Protection against multiple influenza A subtypes by vaccination with highly conserved nucleoprotein. Vaccine 23:5404-5410.
8a. Finter N B. 1964 Quantitative haemadsorption, a new assay technique. I. Assay of interferon. Virology; 24:589-97.
9. Hall, T. A. 1999. BioEdit: a user-friendly biological sequence alignment editor and analysis program for Windows 95/98/NT. Nucl. Acids. Symp. Ser 41:95-98.
10. Johnson, N. P. and J. Mueller. 2002. Updating the accounts: global mortality of the 1918-1920 "Spanish" influenza pandemic. Bull. Hist Med 76:105-115.
11. Kawaoka, Y., S. Krauss, and R. G. Webster. 1989. Avian-to-human transmission of the PB1 gene of influenza A viruses in the 1957 and 1968 pandemics. J Virol 63:4603-4608.
12. Kobasa, D., A. Takada, K. Shinya, M. Hatta, P. Halfmann, S. Theriault, H. Suzuki, H. Nishimura, K. Mitamura, N. Sugaya, T. Usui, T. Murata, Y. Maeda, S.

Watanabe, M. Suresh, T. Suzuki, Y. Suzuki, H. Feldmann, and Y. Kawaoka. 2004. Enhanced virulence of influenza A viruses with the haemagglutinin of the 1918 pandemic virus. Nature 431:703-707.
13. Kodihalli, S., H. Goto, D. L. Kobasa, S. Krauss, Y. Kawaoka, and R. G. Webster. 1999. DNA vaccine encoding haemagglutinin provides protective immunity against H5N1 influenza virus infection in mice. J. Virol. 73:2094-2098.
14. Kodihalli, S., J. R. Haynes, H. L. Robinson, and R. G. Webster. 1997. Cross-protection among lethal H5N2 influenza viruses induced by DNA vaccine to the haemagglutinin. J. Virol. 71:3391-3396.
15. Kodihalli, S., D. L. Kobasa, and R. G. Webster. 2000. Strategies for inducing protection against avian influenza A virus subtypes with DNA vaccines. Vaccine 18:2592-2599.
16. Kong, W. p., C. Hood, Z. y. Yang, C. J. Wei, L. Xu, A. Garcia-Sastre, T. M. Tumpey, and G. J. Nabel. 2006. Protective immunity to lethal challenge of the 1918 pandemic influenza virus by vaccination. PNAS 103:15987-15991.
17. Lindstrom, S. E., N. J. Cox, and A. Klimov. 2004. Genetic analysis of human H2N2 and early H3N2 influenza viruses, 1957-1972: evidence for genetic divergence and multiple reassortment events. Virology 328:101-119.
18. Ljungberg, K., C. Kolmskog, B. Wahren, G. van Amerongen, M. Baars, A. Osterhaus, A. Linde, and G. Rimmelzwaan. 2002. DNA vaccination of ferrets with chimeric influenza A virus haemagglutinin (H3) genes. Vaccine 20:2045-2052.
18a. Ljungberg K, Rollman E, Eriksson L, Hinkula J, Wahren B. Enhanced immune responses after DNA vaccination with combined envelope genes from different HIV-1 subtypes. Virology 2002; 302(1):44-57.
18b. Martel C J, Aasted B. Characterization of antibodies against ferret immunoglobulins, cytokines and CD markers. Vet. Immunol. Immunopathol. 2009;
18C. Olsen C H. Review of the use of statistics in infection and immunity. Infect Immun. 2003; 71(12):6689-92.
19. Reid, A. H., T. G. Fanning, J. V. Hultin, and J. K. Taubenberger. 1999. Origin and evolution of the 1918 "Spanish" influenza virus haemagglutinin gene. Proc. Natl. Acad. Sci. U.S. A 96:1651-1656.
20. Reid, A. H., T. G. Fanning, T. A. Janczewski, and J. K. Taubenberger. 2000. Characterization of the 1918 "Spanish" influenza virus neuraminidase gene. Proc. Natl. Acad. Sci. U.S. A 97:6785-6790.
20a. Schmittgen T D, Zakrajsek B A, Mills A G, Gorn V, Singer M J, Reed M W. Quantitative reverse transcription-polymerase chain reaction to study mRNA decay: comparison of endpoint and real-time methods. Anal. Biochem. 2000; 285(2):194-204.
21. Seo, S. H., E. Hoffmann, and R. G. Webster. 2002. Lethal H5N1 influenza viruses escape host anti-viral cytokine responses. Nat. Med. 8:950-954.
22. Smith, H. and C. Sweet. 1988. Lessons for human influenza from pathogenicity studies with ferrets. Rev. Infect Dis 10:56-75.
23. Spackman, E., D. A. Serene, T. J. Myers, L. L. Bulaga, L. P. Garber, M. L. Perdue, K. Lohman, L. T. Daum, and D. L. Suarez. 2002. Development of a real-time reverse transcriptase PCR assay for type A influenza virus and the avian H5 and H7 haemagglutinin subtypes. J. Clin. Microbiol. 40:3256-3260.
24. Talon, J., C. M. Horvath, R. Polley, C. F. Basler, T. Muster, P. Palese, and A. Garcia-Sastre. 2000. Activation of interferon regulatory factor 3 is inhibited by the influenza A virus NS1 protein. J. Virol. 74:7989-7996.
25. Tamura, S., T. Tanimoto, and T. Kurata. 2005. Mechanisms of broad cross-protection provided by influenza virus infection and their application to vaccines. Jpn. J. Infect Dis 58:195-207.
26. Taubenberger, J. K., A. H. Reid, R. M. Lourens, R. Wang, G. Jin, and T. G. Fanning. 2005. Characterization of the 1918 influenza virus polymerase genes. Nature 437:889-893.
27. Tumpey, T. M., C. F. Basler, P. V. Aguilar, H. Zeng, A. Solorzano, D. E. Swayne, N. J. Cox, J. M. Katz, J. K. Taubenberger, P. Palese, and A. Garcia-Sastre. 2005. Characterization of the reconstructed 1918 spanish influenza pandemic virus. Science 310:77-80.
28a Tumpey, T. M., A. Garcia-Sastre, J. K. Taubenberger, P. Palese, D. E. Swayne, M. J. Pantin-Jackwood, S. Schultz-Chemy, A. Solorzano, N. Van Rooijen, J. M. Katz, and C. F. Basler. 2005b. Pathogenicity of influenza viruses with genes from the 1918 pandemic virus: functional roles of alveolar macrophages and neutrophils in limiting virus replication and mortality in mice. J Virol 79:14933-14944
28. Tumpey, T. M., A. Garcia-Sastre, J. K. Taubenberger, P. Palese, D. E. Swayne, and C. F. Basler. 2004. Pathogenicity and immunogenicity of influenza viruses with genes from the 1918 pandemic virus. Proc. Natl. Acad. Sci. U.S. A 101:3166-3171.
29. Tumpey, T. M., A. Garcia-Sastre, J. K. Taubenberger, P. Palese, D. E. Swayne, M. J. Pantin-Jackwood, S. Schultz-Chemy, A. Solorzano, N. Van Rooijen, J. M. Katz, and C. F. Basler. 2005. Pathogenicity of influenza viruses with genes from the 1918 pandemic virus: functional roles of alveolar macrophages and neutrophils in limiting virus replication and mortality in mice. J Virol 79:14933-14944.
30. Ulmer, J. B., T. M. Fu, R. R. Deck, A. Friedman, L. Guan, C. DeWitt, X. Liu, S. Wang, M. A. Liu, J. J. Donnelly, and M. J. Caulfield. 1998. Protective CD4+ and CD8+ T cells against influenza virus induced by vaccination with nucleoprotein DNA. J Virol 72:5648-5653.
31. Wang, X., M. Li, H. Zheng, T. Muster, P. Palese, A. A. Beg, and A. Garcia-Sastre. 2000. Influenza A Virus NS1 Protein Prevents Activation of NF-kappa B and Induction of Alpha/Beta Interferon. J. Virol. 74:11566-11573.
32. Webster, R. G., E. F. Fynan, J. C. Santoro, and H. Robinson. 1994. Protection of ferrets against influenza challenge with a DNA vaccine to the haemagglutinin. Vaccine 12:1495-1498.
33. WHO. WHO Manual on Animal Influenza Diagnosis and Surveillance. 2009;
34. Vinner L, Therrien D, Wee E, et al. Immune response in rhesus macaques after mixed modality immunisations with DNA, recombinant adenovirus and recombinant gp120 from human immunodeficiency virus type 1. APMIS 2006; 114(10):690-9.

The invention claimed is:

1. An immunogenic composition against influenza A infection in a human or a pig, comprising isolated nucleic acid sequences encoding influenza proteins, wherein the nucleic acid sequences encode for haemagglutinin (HA) and/or neuramidase (NA) and/or matrix protein (M) and/or the nucleoprotein (NP), and wherein the nucleic acid sequences comprise a mix of (a) DNA or RNA from a pandemic influenza virus or DNA or RNA from a non-pandemic influenza virus wherein the DNA or RNA from the non-pandemic virus is mutated, the mutated sequence encoding a protein with fewer glycosylation sites than the non-mutated sequence, wherein said mutated sequence encodes Asn-Y-Ser in place of Asn-X-Ser in at least one occurrence of Asn-X-Ser in said non-mutated sequence,
  wherein X is, individually, in each occurrence of Asn-X-Ser, any amino acid except proline, and
  Y is, individually, in each occurrence of Asn-Y-Ser, any amino acid other than X, and
  (b) DNA or RNA from a different subtype influenza virus is from a H3N2 influenza virus.

2. The immunogenic composition according to claim 1, wherein the immunogenic composition is formulated for administration by injection of isolated naked nucleic acid sequences.

3. The immunogenic composition according to claim 1, wherein the DNA or RNA encoding at least one influenza protein from a H3N2 influenza virus selected from SEQ ID NOs: 15 and 17.

4. An immunogenic composition against influenza A infection in a human or a pig, comprising isolated nucleic acid sequences encoding influenza proteins, wherein the nucleic acid sequences encode for haemagglutinin (HA) and/or neuramidase (NA) and/or matrix protein (M) and/or the nucleoprotein (NP), and wherein the nucleic acid sequences comprise a mix of (a) DNA or RNA from a pandemic influenza virus or DNA or RNA from a non-pandemic influenza virus wherein the DNA or RNA from the non-pandemic virus is mutated, the mutated sequence encoding a protein with fewer glycosylation sites than the non-mutated sequence, wherein said mutated sequence encodes Asn-Y-Thr in place of Asn-X-Thr in at least one occurrence of Asn-X-Thr in said non-mutated sequence,
  wherein X is, individually, in each occurrence of Asn-X-Thr, any amino acid except proline, and
  Y is, individually, in each occurrence of Asn-Y-Thr, any amino acid other than X, and
  (b) DNA or RNA from a different subtype influenza virus is from a H3N2 influenza virus.

5. The immunogenic composition according to claim 3, wherein the DNA or RNA encodes SEQ ID NOs: 15 and 17.

6. The immunogenic composition according to claim 1, wherein the DNA or RNA codons of at least one sequence are optimized.

7. The immunogenic composition according to claim 1, comprising nucleic acid sequences selected from SEQ ID NOs: 1, 3, 5, 7, 10, 12, 14, and 16.

8. The immunogenic composition according to claim 1, wherein the isolated nucleic acid sequences encode at least one sequence selected from SEQ ID NOs: 2, 4, 6, 8, 9, 11, 13, 15, and 17.

9. The immunogenic composition according to claim 1, wherein the immunogenic composition further comprises an adjuvant.

10. The immunogenic composition according to claim 4, wherein the DNA or RNA codons of at least one sequence are optimized.

11. The immunogenic composition according to claim 4, comprising nucleic acid sequences selected from SEQ ID NOs: 1, 3, 5, 7, 10, 12, 14, and 16.

12. The immunogenic composition according to claim 4, wherein the isolated nucleic acid sequences encode at least one sequence selected from SEQ ID NOs: 2, 4, 6, 8, 9, 11, 13, 15, and 17.

13. The immunogenic composition according to claim 4, wherein the immunogenic composition further comprises an adjuvant.

14. The immunogenic composition according to claim 4, wherein the immunogenic composition is formulated for administration by injection of isolated naked nucleic acid sequences.

15. The immunogenic composition according to claim 4, wherein the DNA or RNA encoding at least one influenza protein from a H3N2 influenza virus selected from SEQ ID NOs: 15 and 17.

16. The immunogenic composition according to claim 15, wherein the DNA or RNA encodes SEQ ID NOs: 15 and 17.

* * * * *

SEQUENCE LISTING

<160> NUMBER OF SEQ ID NOS: 29

<210> SEQ ID NO 1
<211> LENGTH: 1701
<212> TYPE: DNA
<213> ORGANISM: Influenza A virus

<400> SEQUENCE: 1

```
atggaggcca ggctgctggt gctgctgtgc gccttcgccg ccaccaacgc cgacaccatc     60
tgcatcggct accacgccaa caacagcacc gacaccgtgg ataccgtgct ggagaagaac    120
gtgaccgtga cccacagcgt gaacctgctg gaggacagcc acaacggcaa gctgtgcaag    180
ctgaagggaa tcgctcccct gcagctgggc aagtgcaaca tcgccggctg gctgctgggc    240
aaccccgagt gcgacctgct gctgaccgcc agcagctggt cctacatcgt ggagaccagc    300
aacagcgaga acggcacctg ctaccccggc gacttcatcg actacgagga gctgcgggag    360
cagctgtcca gcgtgagcag cttcgagaag ttcgagatct tccccaagac cagctcctgg    420
cccaaccacg agaccaccaa gggcgtgacc gccgcctgta gctacgccgg agccagcagc    480
ttctacagaa acctgctgtg gctgaccaag aagggcagca gctaccccaa gctgtccaag    540
agctacgtga acaacaaggg caaggaagtg ctggtgctgt ggggcgtgca ccaccccccct   600
accggcaccg accagcagag cctgtaccag aacgccgacg cctacgtgag cgtgggcagc    660
agcaagtaca acagaaggtt cacccccgag atcgccgcca ggcccaaggt gcgcgaccag    720
gccggcagga tgaactacta ctggaccctg ctggagcccg gcgacaccat caccttcgag    780
gccaccggca acctgatcgc cccttggtac gccttcgccc tgaacagggg cagcggcagc    840
ggcatcatca ccagcgacgc ccccgtgcac gactgcaaca ccaagtgcca gaccccccac    900
ggagccatca acagcagcct gcccttccag aacatccacc ccgtgaccat cggcgagtgc    960
cccaagtacg tgagaagcac caagctgagg atggccaccg gcctgaggaa catccccagc   1020
atccagagca ggggcctgtt cggagccatc gccggattca tcgagggcgg ctggaccggc   1080
atgatcgacg gctggtacgg ctaccaccac cagaacgagc agggcagcgg ctacgccgcc   1140
gaccagaaga gcacccagaa cgccatcgac ggcatcacca acaaggtgaa cagcgtgatc   1200
gagaagatga acacccagtt caccgccgtg ggcaaggagt tcaacaacct ggagaggcgg   1260
atcgagaacc tgaacaagaa ggtggacgac ggcttcctgg acatctggac ctacaacgcc   1320
gagctgctgg tgctgctgga gaacgagagg accctggact tccacgacag caacgtgagg   1380
aacctgtacg agaaggtgaa gagccagctg aagaacaacg ccaaggagat cggcaacggc   1440
tgcttcgagt tctaccacaa gtgcgacgac gcctgcatgg agagcgtgag aaacggcacc   1500
tacgactacc ccaagtacag cgaggagagc aagctgaacc gggaggagat cgacggcgtg   1560
aagctggaga gcatgggcgt gtaccagatc ctggccatct acagcaccgt ggccagcagc   1620
ctggtgctgc tggtgtccct gggagccatc agcttttgga tgtgcagcaa cggcagcctg   1680
cagtgcagga tctgcatctg a                                             1701
```

<210> SEQ ID NO 2
<211> LENGTH: 566
<212> TYPE: PRT
<213> ORGANISM: Influenza A virus

<400> SEQUENCE: 2

```
Met Glu Ala Arg Leu Leu Val Leu Leu Cys Ala Phe Ala Ala Thr Asn
1               5                   10                  15
```

-continued

```
Ala Asp Thr Ile Cys Ile Gly Tyr His Ala Asn Asn Ser Thr Asp Thr
             20                  25                  30

Val Asp Thr Val Leu Glu Lys Asn Val Thr Val Thr His Ser Val Asn
         35                  40                  45

Leu Leu Glu Asp Ser His Asn Gly Lys Leu Cys Lys Leu Lys Gly Ile
     50                  55                  60

Ala Pro Leu Gln Leu Gly Lys Cys Asn Ile Ala Gly Trp Leu Leu Gly
65                   70                  75                  80

Asn Pro Glu Cys Asp Leu Leu Leu Thr Ala Ser Ser Trp Ser Tyr Ile
                 85                  90                  95

Val Glu Thr Ser Asn Ser Glu Asn Gly Thr Cys Tyr Pro Gly Asp Phe
             100                 105                 110

Ile Asp Tyr Glu Glu Leu Arg Glu Gln Leu Ser Ser Val Ser Ser Phe
         115                 120                 125

Glu Lys Phe Glu Ile Phe Pro Lys Thr Ser Ser Trp Pro Asn His Glu
     130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                 165                 170                 175

Lys Leu Ser Lys Ser Tyr Val Asn Asn Lys Gly Lys Glu Val Leu Val
             180                 185                 190

Leu Trp Gly Val His His Pro Pro Thr Gly Thr Asp Gln Gln Ser Leu
         195                 200                 205

Tyr Gln Asn Ala Asp Ala Tyr Val Ser Val Gly Ser Ser Lys Tyr Asn
     210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                 245                 250                 255

Ile Thr Phe Glu Ala Thr Gly Asn Leu Ile Ala Pro Trp Tyr Ala Phe
             260                 265                 270

Ala Leu Asn Arg Gly Ser Gly Ser Gly Ile Ile Thr Ser Asp Ala Pro
         275                 280                 285

Val His Asp Cys Asn Thr Lys Cys Gln Thr Pro His Gly Ala Ile Asn
     290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                 325                 330                 335

Asn Ile Pro Ser Ile Gln Ser Arg Gly Leu Phe Gly Ala Ile Ala Gly
             340                 345                 350

Phe Ile Glu Gly Gly Trp Thr Gly Met Ile Asp Gly Trp Tyr Gly Tyr
         355                 360                 365

His His Gln Asn Glu Gln Gly Ser Gly Tyr Ala Ala Asp Gln Lys Ser
     370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                 405                 410                 415

Leu Glu Arg Arg Ile Glu Asn Leu Asn Lys Lys Val Asp Asp Gly Phe
             420                 425                 430

Leu Asp Ile Trp Thr Tyr Asn Ala Glu Leu Leu Val Leu Leu Glu Asn
```

| | 435 | | | | 440 | | | | 445 | | | |
|---|---|---|---|---|---|---|---|---|---|---|---|---|

Glu Arg Thr Leu Asp Phe His Asp Ser Asn Val Arg Asn Leu Tyr Glu
450                     455                     460

Lys Val Lys Ser Gln Leu Lys Asn Asn Ala Lys Glu Ile Gly Asn Gly
465                     470                     475                     480

Cys Phe Glu Phe Tyr His Lys Cys Asp Asp Ala Cys Met Glu Ser Val
            485                     490                     495

Arg Asn Gly Thr Tyr Asp Tyr Pro Lys Tyr Ser Glu Glu Ser Lys Leu
            500                     505                     510

Asn Arg Glu Glu Ile Asp Gly Val Lys Leu Glu Ser Met Gly Val Tyr
            515                     520                     525

Gln Ile Leu Ala Ile Tyr Ser Thr Val Ala Ser Ser Leu Val Leu Leu
530                     535                     540

Val Ser Leu Gly Ala Ile Ser Phe Trp Met Cys Ser Asn Gly Ser Leu
545                     550                     555                     560

Gln Cys Arg Ile Cys Ile
            565

<210> SEQ ID NO 3
<211> LENGTH: 1410
<212> TYPE: DNA
<213> ORGANISM: Influenza A virus

<400> SEQUENCE: 3

| | | | | | |
|---|---|---|---|---|---|
| atgaacccca | accagaagat | catcaccatc | ggcagcatct | gcatggtggt | gggcatcatc | 60 |
| agcctgatcc | tgcagatcgg | caacatcatc | agcatctggg | tgtcccacag | catccagacc | 120 |
| ggcaaccaga | ccaccccga | gacctgcaac | cagtccatca | tcacctacga | gaacaacacc | 180 |
| tgggtgaacc | agacctacgt | gaacatcagc | aacaccaacg | tggtggccgg | ccaggacgcc | 240 |
| acctccgtga | tcctgacagg | caacagcagc | ctgtgcccca | tcagcggctg | ggccatctac | 300 |
| agcaaggaca | acggcatcag | gatcggcagc | aagggcgacg | tgttcgtgat | cagagagccc | 360 |
| ttcatcagct | gcagccacct | ggaatgcagg | accttcttcc | tgacccaagg | agccctgctg | 420 |
| aacgacaagc | acagcaacgg | caccgtgaag | gacagaagcc | cctacaggac | cctgatgagc | 480 |
| tgccccgtgg | gcgaggctcc | cagcccctac | aacagcagat | cgagagcgt | ggcctggtcc | 540 |
| gccagcgcct | gccacgacgg | catgggctgg | ctgaccatcg | gcatcagcgg | ccctgacaac | 600 |
| ggggccgtgg | ccgtgctgaa | gtacaacgga | atcatcaccg | acaccatcaa | gagctggcgg | 660 |
| aacaacatcc | tgaggaccca | ggaaagcgag | tgcgcctgcg | tgaacggcag | ctgcttcacc | 720 |
| atcatgaccg | acggccccag | caacggccag | gccagctaca | agatcctgaa | gatcgagaag | 780 |
| ggcaaggtga | ccaagagcat | cgagctgaac | gcccccaact | accactacga | ggaatgcagc | 840 |
| tgctacccccg | acaccggcaa | ggtcatgtgc | gtgtgcaggg | acaactggca | cggcagcaac | 900 |
| aggccctggg | tgtccttcga | ccagaacctg | gactaccaga | tcggatacat | ctgcagcggc | 960 |
| gtgttcggcg | acaaccccag | gcccaacgac | ggcaccggca | gctgcggccc | tgtgagcagc | 1020 |
| aacggggcca | atggcatcaa | gggcttcagc | ttcagatacg | acaacggcgt | gtggatcggc | 1080 |
| cgcaccaaga | gcaccagcag | cagatccggc | ttcgagatga | tctgggaccc | caacggctgg | 1140 |
| accgagaccg | acagcagctt | cagcgtgagg | caggacatcg | tggccatcac | cgactggtcc | 1200 |
| ggctacagcg | gcagcttcgt | gcagcacccc | gagctgaccg | gcctggactg | catgaggccc | 1260 |
| tgtttctggg | tggagctgat | cagaggccag | cccaaggaga | acaccatctg | gaccagcggc | 1320 |
| agcagcatca | gcttttgcgg | cgtgaacagc | gacaccgtgg | gctggtcctg | gcccgacggg | 1380 | gccgagctgc ccttcagcat cgataagtga          1410

<210> SEQ ID NO 4
<211> LENGTH: 469
<212> TYPE: PRT
<213> ORGANISM: Influenza A virus

<400> SEQUENCE: 4

```
Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Val Ser His Ser Ile Gln Thr Gly Asn Gln Asn His Pro Glu Thr
        35                  40                  45

Cys Asn Gln Ser Ile Ile Thr Tyr Glu Asn Asn Thr Trp Val Asn Gln
    50                  55                  60

Thr Tyr Val Asn Ile Ser Asn Thr Asn Val Val Ala Gly Gln Asp Ala
65                  70                  75                  80

Thr Ser Val Ile Leu Thr Gly Asn Ser Ser Leu Cys Pro Ile Ser Gly
                85                  90                  95

Trp Ala Ile Tyr Ser Lys Asp Asn Gly Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Thr Leu Met Ser
145                 150                 155                 160

Cys Pro Val Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asn Gly Gln Ala Ser Tyr Lys Ile Leu
                245                 250                 255

Lys Ile Glu Lys Gly Lys Val Thr Lys Ser Ile Glu Leu Asn Ala Pro
            260                 265                 270

Asn Tyr His Tyr Glu Glu Cys Ser Cys Tyr Pro Asp Thr Gly Lys Val
        275                 280                 285

Met Cys Val Cys Arg Asp Asn Trp His Gly Ser Asn Arg Pro Trp Val
    290                 295                 300

Ser Phe Asp Gln Asn Leu Asp Tyr Gln Ile Gly Tyr Ile Cys Ser Gly
305                 310                 315                 320

Val Phe Gly Asp Asn Pro Arg Pro Asn Asp Gly Thr Gly Ser Cys Gly
                325                 330                 335

Pro Val Ser Ser Asn Gly Ala Asn Gly Ile Lys Gly Phe Ser Phe Arg
            340                 345                 350

Tyr Asp Asn Gly Val Trp Ile Gly Arg Thr Lys Ser Thr Ser Ser Arg
        355                 360                 365
```

Ser Gly Phe Glu Met Ile Trp Asp Pro Asn Gly Trp Thr Glu Thr Asp
    370             375                 380

Ser Ser Phe Ser Val Arg Gln Asp Ile Val Ala Ile Thr Asp Trp Ser
385             390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Ile Arg Gly Gln Pro Lys
            420                 425                 430

Glu Asn Thr Ile Trp Thr Ser Gly Ser Ser Ile Ser Phe Cys Gly Val
            435                 440                 445

Asn Ser Asp Thr Val Gly Trp Ser Trp Pro Asp Gly Ala Glu Leu Pro
        450                 455                 460

Phe Ser Ile Asp Lys
465

<210> SEQ ID NO 5
<211> LENGTH: 1497
<212> TYPE: DNA
<213> ORGANISM: Influenza A virus

<400> SEQUENCE: 5

| | |
|---|---:|
| atggccagcc agggcaccaa gagaagctac gagcagatgg aaaccgacgg cgagaggcag | 60 |
| aacgccaccg agatcagggc cagcgtgggc aggatgatcg gcggcatcgg caggttctac | 120 |
| atccagatgt gcaccgagct gaagctgtcc gactacgagg caggctgat ccagaacagc | 180 |
| atcaccatcg agaggatggt gctgtccgcc ttcgacgaga agagaaacaa gtacctggaa | 240 |
| gagcacccca gcgccggcaa ggaccccaag aaaaccggcg acccatctca gaaggatc | 300 |
| gacggcaagt ggatgagaga gctgatcctg tacgacaagg aggaaatcag aaggatctgg | 360 |
| cggcaggcca acaacggcga ggacgccaca gccggcctga cccacatgat gatctggcac | 420 |
| agcaacctga cgacgccac ctaccagagg accaggccc tcgtcagaac cggcatggac | 480 |
| ccccggatgt gcagcctgat gcagggcagc acactgccca agaagcgg agctgctgga | 540 |
| gccgccgtga gggcgtggg caccatggtg atggaactga tcaggatgat caagaggggc | 600 |
| atcaacgaca ggaacttttg gagggcgag aacggcagaa ggaccaggat cgcctacgag | 660 |
| aggatgtgca acatcctgaa gggcaagttc cagacagccg cccagagggc catgatggac | 720 |
| caggtccggg agagcaggaa ccccggcaac gccgagatcg aggacctgat cttcctggcc | 780 |
| agaagcgccc tgatcctgag gggcagcgtg cccacaagga ctgcctgcc cgcctgcgtg | 840 |
| tacggacccg ccgtggccag cggctacgac ttcgagagag agggctacag cctggtcggc | 900 |
| atcgacccct tcaggctgct gcagaactcc caggtgtact ctctgatcag gcccaacgag | 960 |
| aacccgccc acaagtccca gctggtctgg atggcctgcc acagcgccgc cttcgaggat | 1020 |
| ctgagagtga gcagcttcat cagggggcacc agagtggtgc caggggcaa gctgtccacc | 1080 |
| aggggcgtgc agatcgccag caacgagaac atggaaacca tggacagcag cacccctggaa | 1140 |
| ctgagaagca ggtactgggc catcaggacc agaagcggcg caacaccaa ccagcagagg | 1200 |
| gccagcgccg acagatcag cgtgcagccc accttctccg tgcagaggaa cctgccctc | 1260 |
| gagagggcca ccatcatggc cgccttcacc ggcaacaccg agggcaggac cagcgacatg | 1320 |
| aggaccgaga tcatcagaat gatggaaagc gccaggccgg aggacgtgag cttccagggc | 1380 |
| aggggcgtgt cgagctgtc cgatgagaag gccacctccc ccatcgtgcc cagcttcgac | 1440 |
| atgagcaacg agggcagcta cttcttcggc gacaacgccg aggaatacga caactga | 1497 |

<210> SEQ ID NO 6
<211> LENGTH: 498
<212> TYPE: PRT
<213> ORGANISM: Influenza A virus

<400> SEQUENCE: 6

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Ile Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Lys Leu Ser Thr Arg Gly Val Gln Ile Ala Ser Asn
        355                 360                 365

Glu Asn Met Glu Thr Met Asp Ser Ser Thr Leu Glu Leu Arg Ser Arg
```

```
                370             375             380
Tyr Trp Ala Ile Arg Thr Arg Ser Gly Gly Asn Thr Asn Gln Gln Arg
385             390             395             400

Ala Ser Ala Gly Gln Ile Ser Val Gln Pro Thr Phe Ser Val Gln Arg
                405             410             415

Asn Leu Pro Phe Glu Arg Ala Thr Ile Met Ala Ala Phe Thr Gly Asn
            420             425             430

Thr Glu Gly Arg Thr Ser Asp Met Arg Thr Glu Ile Ile Arg Met Met
        435             440             445

Glu Ser Ala Arg Pro Glu Asp Val Ser Phe Gln Gly Arg Gly Val Phe
    450             455             460

Glu Leu Ser Asp Glu Lys Ala Thr Ser Pro Ile Val Pro Ser Phe Asp
465             470             475             480

Met Ser Asn Glu Gly Ser Tyr Phe Phe Gly Asp Asn Ala Glu Glu Tyr
                485             490             495

Asp Asn
```

<210> SEQ ID NO 7
<211> LENGTH: 988
<212> TYPE: DNA
<213> ORGANISM: Influenza A virus

<400> SEQUENCE: 7

```
atgagtcttt taaccgaggt cgaaacgtac gttctctcta tcgtcccgtc aggccccctc     60
aaagccgaga tcgcgcagag acttgaagat gtctttgcag ggaagaacac cgatcttgag    120
gctctcatgg aatggctaaa gacaagacca atcctgtcac ctctgactaa ggggatttta    180
ggatttgtgt tcacgctcac cgtgcccagt gagcgaggac tgcagcgtag acgctttgtc    240
caaaatgccc ttaatgggaa cggggatcca ataacatgg acagagcagt taaactgtac    300
aggaagctta agagggagat aacattccat ggggccaaag aagtagcact cagttattcc    360
gctggtgcac ttgccagttg tatgggcctc atatacaaca ggatggggac tgtgaccact    420
gaagtggcat ttggcctggt atgcgcaacc tgtgaacaga ttgctgattc ccagcatcgg    480
tctcacaggc aaatggtgac aacaaccaat ccactaatca acatgagaa cagaatggta    540
ctggccagca ctacggctaa ggctatggag caaatggctg gatcgagtga gcaagcagca    600
gaggccatgg aggttgctag tcaggctagg caaatggtgc aggcgatgag aaccattggg    660
actcatccta gctccagtgc tggtctgaaa gacgatctta ttgaaaattt gcaggcctac    720
cagaaacgaa tggggtgca gatgcaacga ttcaagtgat cctctcgtta ttgccgcaag    780
tatcattggg atcttgcact tgatattgtg gattcttgat cgtctttttt tcaaatgcat    840
ttatcgtcgc cttaaatacg gtttgaaaag agggccttct acggaaggag tgccggagtc    900
tatgagggaa gaatatcgaa aggaacagca gagtgctgtg gatgttgacg atggtcattt    960
tgtcaacata gagctggagt aaggcgcc                                        988
```

<210> SEQ ID NO 8
<211> LENGTH: 252
<212> TYPE: PRT
<213> ORGANISM: Influenza A virus

<400> SEQUENCE: 8

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
```

```
                    20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
        50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Thr Val Thr Thr Glu Val Ala Phe
130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
210                 215                 220

Ser Ser Ala Gly Leu Lys Asp Asp Leu Ile Glu Asn Leu Gln Ala Tyr
225                 230                 235                 240

Gln Lys Arg Met Gly Val Gln Met Gln Arg Phe Lys
                245                 250

<210> SEQ ID NO 9
<211> LENGTH: 97
<212> TYPE: PRT
<213> ORGANISM: Influenza A virus

<400> SEQUENCE: 9

Met Ser Leu Leu Thr Glu Val Glu Thr Pro Thr Arg Asn Glu Trp Gly
1               5                   10                  15

Cys Arg Cys Asn Asp Ser Ser Asp Pro Leu Val Ile Ala Ala Ser Ile
            20                  25                  30

Ile Gly Ile Leu His Leu Ile Leu Trp Ile Leu Asp Arg Leu Phe Phe
        35                  40                  45

Lys Cys Ile Tyr Arg Arg Leu Lys Tyr Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Ser Ala Val Asp Val Asp Asp Gly His Phe Val Asn Ile Glu Leu
                85                  90                  95

Glu

<210> SEQ ID NO 10
<211> LENGTH: 1723
<212> TYPE: DNA
<213> ORGANISM: Influenza A virus

<400> SEQUENCE: 10
```

-continued

```
atgaaggcta tcctggtggt gctgctgtac accttcgcca ccgccaacgc cgataccctg      60
tgcatcggct accacgccaa caacagcacc gacaccgtgg ataccgtgct ggaaaagaac     120
gtgaccgtga cccacagcgt gaacctgctg gaagataagc acaacggcaa gctgtgcaag     180
ctgagaggcg tggcccctct gcacctgggc aagtgcaata tcgccggctg gatcctgggc     240
aaccccgagt gcgagagcct gagcaccgcc agctcttggt cctacatcgt ggagacaccc     300
agcagcgaca acggcacctg ttaccccggc gacttcatcg actacgagga actgcgggag     360
cagctgtcca gcgtgtccag cttcgagcgg ttcgagatct tccccaagac cagctcctgg     420
cccaaccacg acagcaacaa gggcgtgacc gccgcctgtc ctcacgctgg ggccaagagc     480
ttctacaaga acctgatctg gctggtgaag aagggcaaca gctaccccaa gctgtccaag     540
agctacatca acgacaaggg caaagaggtg ctggtgctgt ggggcatcca ccaccctagc     600
accagcgccg accagcagag cctgtaccag aacgccgaca cctacgtgtt cgtgggcagc     660
agccggtaca gcaagaagtt caagcccgag atcgccatca gacccaaagt gcgggaccag     720
gaaggccgga tgaactacta ctggaccctg gtggagcccg gcgacaagat caccttcgag     780
gccaccggca atctggtggt gcccagatac gccttcgcca tggaaagaaa cgccggcagc     840
ggcatcatca tcagcgacac ccccgtgcac gactgcaaca ccacctgtca gacccccaag     900 gggggccatca acaccagcct gcccttccag aacatccacc ccatcaccat cggcaagtgc     960
cctaagtacg tgaagtccac caagctgaga ctggccaccg gcctgcggaa catccccagc    1020
atccagagca gaggcctgtt cggggccatt gccggcttta tcgagggcgg ctggaccgga    1080
atggtggacg ggtggtacgg ctaccaccac cagaatgagc agggcagcgg ctacgccgcc    1140
gacctgaagt ccacacagaa cgccatcgac gagatcacca acaaagtgaa cagcgtgatc    1200
gagaagatga acacccagtt caccgccgtg ggcaaagagt tcaaccacct ggaaaagcgg    1260
atcgagaacc tgaacaagaa ggtggacgac ggcttcctgg acatctggac ctacaacgcc    1320
gagctgctgg tgctgctgga aaacgagcgg accctggact accacgactc caacgtgaag    1380
aatctgtacg agaaagtgcg gagccagctg aagaacaacg ccaaagagat cggcaacggc    1440
tgcttcgagt tctaccacaa gtgcgacaac acctgtatgg aaagcgtgaa gaacggcacc    1500
tacgactacc ccaagtacag cgaggaagcc aagctgaacc gggaagagat cgacggcgtg    1560
aagctggaaa gcacccggat ctaccagatc ctggccatct acagcaccgt ggccagctca    1620
ctggtcctgg tcgtgtccct gggcgctatc agcttctgga tgtgcagcaa cggcagcctg    1680
cagtgccgga tctgcatctg aggcgccgag aattcttaat taa                      1723
```

<210> SEQ ID NO 11
<211> LENGTH: 566
<212> TYPE: PRT
<213> ORGANISM: Influenza A virus

<400> SEQUENCE: 11

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60
```

```
Ala Pro Leu His Leu Gly Lys Cys Asn Ile Ala Gly Trp Ile Leu Gly
 65                  70                  75                  80

Asn Pro Glu Cys Glu Ser Leu Ser Thr Ala Ser Ser Trp Ser Tyr Ile
                 85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
```

```
                485                 490                 495
Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 12
<211> LENGTH: 1432
<212> TYPE: DNA
<213> ORGANISM: Influenza A virus

<400> SEQUENCE: 12
atgaacccca accagaagat catcaccatc ggcagcgtgt gcatgaccat cggcatggcc      60
aacctgatcc tgcagatcgg caacatcatc agcatctgga tcagccacag catccagctg     120
ggcaaccaga accagatcga cattgcaac cagagcgtga tcacctacga gaacaacacc      180
tgggtgaacc agacctacgt gaacatcagc aacaccaact cgccgctgg ccagagcgtg      240
gtgtctgtga agctggccgg caacagcagc ctgtgccctg tgtccggctg gccatctac     300
agcaaggaca cagcgtgcg gatcggcagc aagggcgacg tgttcgtgat ccggagccc      360
ttcatcagct gcagccccct ggaatgccgg accttcttcc tgacccaggg ggccctgctg    420
aacgacaagc acagcaacgg caccatcaag gacagaagcc cctaccggac cctgatgagc   480
tgccccatcg gcgaggtgcc cagcccctac aacagcagat cgagtccgt ggcttggagc    540
gcctctgcct gccacgacgg catcaactgg ctgacaatcg gcatcagcgg ccctgataac    600
ggcgctgtgg ccgtgctgaa gtacaacggc atcatcaccg acacaatcaa gagctggcgg   660
aacaacatcc tgcggaccca ggaatccgag tgcgcctgcg tgaacggcag ctgcttcacc   720
gtgatgaccg acggccctag caatggccag gccagctaca gatcttccg gatcgagaag   780
ggcaagatcg tgaagtccgt ggagatgaac gcccccaact accactacga ggaatgcagc   840
tgctacccg acagcagcga gatcacctgt gtgtgccggg acaactggca cggcagcaac   900
agaccctggg tgtccttcaa ccagaatctg gaataccaga tcggctacat ttgcagcggc   960
atcttcggcg acaaccccag acccaacgac aagaccggaa gctgcggccc tgtgtctagc  1020
aacggggcca acggcgtgaa gggcttcagc ttcaagtacg gcaatggcgt gtggatcggc  1080
cggaccaaga gcatcagcag ccggaacggc ttcgagatga tctgggaccc caacggctgg  1140
accggcaccg acaacaactt cagcatcaag caggacatcg tgggcatcaa cgagtggagc  1200
ggctacagcg gcagcttcgt gcagcaccct gagctgaccg gcctggactg catccggccc  1260
tgcttttggg tggagctgat cagaggcaga cccaaagaga acaccatctg gaccagcggc  1320
agcagcatca gcttttgcgg cgtgaacagc gacaccgtgg gctggtcttg gcccgatggg  1380
gccgagctgc ccttcaccat cgacaagtga ggcgccgaga attcttaatt aa           1432

<210> SEQ ID NO 13
<211> LENGTH: 469
<212> TYPE: PRT
<213> ORGANISM: Influenza A virus
```

```
<400> SEQUENCE: 13

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
                35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415
```

```
Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
            435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 14
<211> LENGTH: 1698
<212> TYPE: DNA
<213> ORGANISM: Influenza A virus

<400> SEQUENCE: 14
```

| | | | | | |
|---|---|---|---|---|---|
| atgaaaacca | tcatcgccct | gagctacatc | ctgtgcctgg | tgttcgccca | gaagctgccc | 60 |
| ggcaacgaca | cagcaccgc | caccctgtgc | ctgggccacc | acgccgtgcc | caacggcacc | 120 |
| atcgtcaaaa | ccattaccaa | tgatcagatc | gaggtgacca | cgccaccga | gctggtgcag | 180 |
| agcagcagca | ccggcggcat | ctgcgacagc | ccccaccaga | tcctggacgg | cgagaactgc | 240 |
| accctgatcg | acgctctgct | cggcgaccct | cagtgcgacg | gcttccagaa | caagaagtgg | 300 |
| gacctgttcg | tcgagcgcag | caaggcctac | agcaactgct | accccacga | cgtgcccgac | 360 |
| tacgccagcc | tccgctccct | ggtcgcctcc | agcggcaccc | tggagttcaa | cgacgagagc | 420 |
| ttcaactgga | ccggcgtgac | ccagaacggc | accagcagca | gctgcaagcg | ccgcagcaac | 480 |
| aacagcttct | tcagccgcct | gaactggctg | acccacctga | agttcaagta | ccccgccctg | 540 |
| aacgtgacca | tgcccaacaa | tgagaaattc | gacaagctgt | acatctgggg | cgtgcaccac | 600 |
| cccgtgaccg | acaacgacca | gatcttcctg | tacgcccagg | ccagcggccg | catcaccgtg | 660 |
| agcaccaagc | gcagccagca | gaccgtgatc | cccaacatcg | gcagccgccc | caggatccgc | 720 |
| aacatcccca | gccgcatcag | catctactgg | accatcgtga | agcccggcga | catcctgctg | 780 |
| atcaactcca | ccggcaacct | gatcgccccc | aggggctact | tcaagatccg | cagcggcaag | 840 |
| agcagcatca | tgcgcagcga | cgcccccatc | ggcaagtgca | acagcgagtg | catcacccc | 900 |
| aacggcagca | tccccaacga | caagcccttc | cagaacgtga | accgcatcac | ctacggagcc | 960 |
| tgtcccccgct | acgtgaagca | gaacaccctg | aaactggcta | ccggcatgcg | gaacgtgccc | 1020 |
| gagaagcaga | cccggggcat | cttcgggggcc | atcgccggct | tcatcgagaa | cggctgggag | 1080 |
| ggcatggtgg | acgggtggta | tggcttccgc | caccagaact | ccgagggcat | cggccaggcc | 1140 |
| gccgacctga | agagcaccca | ggccgccatc | aaccagatca | cggcaagct | gaaccgcctg | 1200 |
| atcggcaaga | ccaacgagaa | gttccaccag | atcgagaagg | agtttagcga | ggtcgagggc | 1260 |
| cgcatccagg | acctggagaa | gtacgtggag | gacaccaaga | tcgacctgtg | gagctacaac | 1320 |
| gccgagctgc | tggtcgccct | ggagaaccag | cacaccatcg | acctgaccga | cagcgagatg | 1380 |
| aacaagctgt | tcgagcgcac | caagaagcag | ctgcgcgaga | acgccgagga | catgggcaac | 1440 |
| ggctgcttca | agatctacca | caagtgcgac | aacgcctgca | tcggctccat | ccgcaacggc | 1500 |
| acctacgacc | acgacgtgta | ccgcgacgag | gccctgaaca | accgcttcca | gatcaagggc | 1560 |
| gtggagctga | agagcggcta | caaggactgg | atcctgtgga | tcagcttcgc | tatcagctgc | 1620 |
| ttcctgctgt | gcgtggccct | gctgggcttc | atcatgtggg | cctgccagaa | gggcaacatc | 1680 |
| cgctgcaaca | tctgcatc | | | | | 1698 |

<210> SEQ ID NO 15
<211> LENGTH: 566
<212> TYPE: PRT
<213> ORGANISM: Influenza A virus

<400> SEQUENCE: 15

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380
```

```
Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
        420                 425                 430

Lys Ile Asp Leu Trp Ser Tyr Asn Ala Glu Leu Leu Val Ala Leu Glu
    435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
            485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
            565

<210> SEQ ID NO 16
<211> LENGTH: 1410
<212> TYPE: DNA
<213> ORGANISM: Influenza A virus

<400> SEQUENCE: 16
atgaacccca accagaagat catcaccatc ggatccgtca gcctgaccat ctccaccatc      60 tgcttttca tgcagatcgc catcctgatc accaccgtga ccctgcactt caagcagtac     120
gagttcaaca gcccccccaa caaccaggtc atgctgtgcg agcccaccat catcgagcgc     180
aacatcaccg agatcgtgta cctgaccaac accaccatcg agaaagagat ctgccccaag     240
ctggccgagt accgcaactg gtccaagccc cagtgcaata tcacaggctt cgccccttc      300 agcaaggaca cagcatccg cctgagcgct ggaggggaca tctgggtcac ccgcgagccc      360
tacgtgagct cgcaccccga caagtgctac cagttcgccc tcggacaggg gaccacactg     420
aataacgtcc acagcaacga caccgtgcac gaccgcaccc cctaccgcac cctgctgatg     480
aacgagctgg gcgtgccctt ccacctgggc accaagcagg tctgcatcgc ctggtccagc     540
agcagctgcc acgacggcaa ggcctggctg cacgtgtgcg tgaccggcga cgacaagaac     600
gccaccgcca gcttcatcta caacggccgc ctggtggaca gcatcgtgag ctggtccaaa     660
gagatcctgc gcacccaaga aagcgagtgc gtctgcatca cggcacctg caccgtggtg     720 atgaccgacg gcagcgcctc cggcaaggcc gacaccaaga tcctgttcat cgaagagggc     780
aagatcgtgc acaccagcac actgtccggc agcgcccagc acgtggaaga gtgcagctgc     840
tacccccgct acctgggcgt gcgctgcgtg tgccgcgaca actggaaggg cagcaaccgc     900
cccatcgtgg acatcaacat caaggactac tccatcgtga gcagctacgt gtgcagcggc     960
ctggtcggcg acacacccg caagaacgac agcagctcca gcagccactg cctggacccc    1020
```

-continued

```
aacaacgaag agggcggcca cggcgtgaag ggctgggcct tcgacgacgg caacgacgtg    1080
tggatgggcc gcaccatcag cgagaagctg cggagcggct atgagacatt caaggtgatc    1140
gagggctggt ccaaccccaa cagcaagctg cagatcaacc gccaggtgat cgtggaccgc    1200
ggcaaccgct ccggctacag cggcatcttc agcgtggagg gcaagtcctg catcaaccgc    1260
tgcttctatg tggagctgat tcgggggagg aaagaagaga ccgaggtcct ctggaccagc    1320
aacagcatcg tggtgttctg cggcaccagc ggcacctacg gcaccggcag ctggcccgac    1380
ggggccgaca tcaacctgat gcccatctga                                     1410
```

```
<210> SEQ ID NO 17
<211> LENGTH: 469
<212> TYPE: PRT
<213> ORGANISM: Influenza A virus

<400> SEQUENCE: 17
```

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asn
        195                 200                 205

Gly Arg Leu Val Asp Ser Ile Val Ser Trp Ser Lys Glu Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Leu Gly Val Arg
        275                 280                 285

Cys Val Cys Arg Asp Asn Trp Lys Gly Ser Asn Arg Pro Ile Val Asp
    290                 295                 300
```

-continued

```
Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 18
<211> LENGTH: 1731
<212> TYPE: DNA
<213> ORGANISM: Influenza A virus

<400> SEQUENCE: 18
ataattctat taatcatgaa gaccatcatt gctttgagct acattttctg tctggctctc     60
ggccaagacc ttccaggaaa tgacaacagc acagcaacgc tgtgcctggg acatcatgcg    120
gtgccaaacg gaacactagt gaaaacaatc acagatgatc agattgaagt gactaatgct    180
actgagctag ttcagagctc ctcaacgggg aaaatatgca acaatcctca tcgaatcctt    240
gatggaatag actgcacact gatagatgct ctattggggg accctcattg tgatgttttt    300
caaaatgaga catgggacct tttcgttgaa cgcagcaaag ctttcagcaa ctgttaccct    360
tatgatgtgc cagattatgc ctcccttagg tcactagttg cctcgtcagg cactctggag    420
tttatcactg agggtttcac ttggactggg gtcactcaga atgggggaag caatgcttgc    480
aaaaggggac ctggtagcgg tttttttcagt agactgaact ggttgaccaa atcaggaagc    540
acatatccag tgctgaacgt gactatgcca aacaatgaca attttgacaa actatacatt    600
tggggggttc accacccgag cacgaaccaa gaacaaacca gcctgtatgt tcaagcatca    660
gggagagtca cagtctctac caggagaagc cagcaaacta taatcccgaa tatcgagtcc    720
agaccctggg taaggggtct gtctagtaga ataagcatct attggacaat agttaagccg    780
ggagacgtac tggtaattaa tagtaatggg aacctaatcg ctcctcgggg ttatttcaaa    840
atgcgcactg ggaaaagctc aataatgagg tcagatgcac ctattgatac ctgtatttct    900
gaatgcatca ctccaaatgg aagcattccc aatgacaagc cctttcaaaa cgtaaacaag    960
atcacatatg gagcatgccc caagtatgtt aagcaaaaca ccctgaagtt ggcaacaggg   1020
atgcggaatg taccagagaa acaaactaga ggcctattcg gcgcaatagc aggtttcata   1080
gaaaatggtt gggagggaat gatagacggt tggtacggtt tcaggcatca aaattctgag   1140
```

-continued

```
ggcacaggac aagcagcaga tcttaaaagc actcaagcag ccatcgacca aatcaatggg   1200
aaattgaaca gggtaatcga gaagacgaac gagaaattcc atcaaatcga aaaggaattc   1260
tcagaagtag aagggagaat tcaggacctc gagaaatacg ttgaagacac taaaatagat   1320
ctctggtctt acaatgcgga gcttcttgtc gctctggaga atcaacatac aattgacctg   1380
actgactcgg aaatgaacaa gctgtttgaa aaaacaagga ggcaactgag ggaaaatgct   1440
gaagacatgg gcaatggttg cttcaaaata taccacaaat gtgacaacgc ttgcatagag   1500
tcaatcagaa atgggactta tgaccatgat gtatacagag acgaagcatt aaacaaccgg   1560
tttcagatca aggtgttgga actgaagtct ggatacaaag actggatcct gtggatttcc   1620
tttgccatat catgcttttt gctttgtgtt gttttgctgg ggttcatcat gtgggcctgc   1680
cagagaggca acattaggtg caacatttgc atttgagtgt attagtaatt a            1731
```

<210> SEQ ID NO 19
<211> LENGTH: 566
<212> TYPE: PRT
<213> ORGANISM: Influenza A virus

<400> SEQUENCE: 19

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Glu Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270
```

```
Tyr Phe Lys Met Arg Thr Gly Lys Ser Ser Ile Met Arg Ser Asp Ala
                275                 280                 285

Pro Ile Asp Thr Cys Ile Ser Glu Cys Ile Thr Pro Asn Gly Ser Ile
            290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
        370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
435                 440                 445

Asn Gln His Thr Ile Asp Leu Thr Asp Ser Glu Met Asn Lys Leu Phe
            450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 20
<211> LENGTH: 1431
<212> TYPE: DNA
<213> ORGANISM: Influenza A virus

<400> SEQUENCE: 20
gaaaatgaat ccaaatcaaa agataataac aattggctct gtctctctca ccattgcaac     60
agtatgcttc ctcatgcaga ttgccatcct ggtaactact gtaacattgc attttaagca    120
atatgagtgc gactcccccg cgagcaacca gtaatgccg tgtgaaccaa taataataga    180
aaggaacata acagagatag tgtatttgaa taacaccacc atagaaaag agatatgccc    240 caaagtagtg gaatacagaa attggtcaaa gccgcaatgt caaattacag gatttgcacc    300 ttttttctaag acaattcaa tccggctttc tgctggtggg gacatttggg tgacgagaga    360
accttatgtg tcatgcgatc atggcaagtg ttatcaattt gcactcgggc aggggaccac    420
```

-continued

```
actagacaac aaacattcaa atgacacaat acatgataga atccctcatc gaaccctatt      480
aatgaatgag ttgggtgttc catttcattt aggaaccagg caagtgtgta tagcatggtc      540
cagctcaagt tgtcacgatg aaaagcatg gctgcatgtt tgtatcactg gggatgacaa       600
aaatgcaact gctagcttca tttatgacgg gaggcttgtg acagtattg gttcatggtc       660
tcaaaatatc ctcagaaccc aggagtcgga atgcgtttgt atcaatggga cttgcacagt      720
agtaatgact gatggaagtg cttcaggaag agccgatact agaatactat tcattgaaga      780
ggggaaaatt gtccatatta gcccattgtc aggaagtgct cagcatgtag aagagtgttc      840
ctgttatcct agatatcctg gcgtcagatg tatctgcaga gacaactgga aaggctctaa      900
taggcccgtc gtagacataa atatggaaga ttatagcatt gattccagtt atgtgtgctc      960
agggcttgtt ggcgacacac ctagaaacga cgacagatct agcaatagca attgcaggaa     1020
tcctaataat gagagaggga atcaaggagt gaaaggctgg gcctttgaca atggagatga     1080
cgtgtggatg ggaagaacga tcagcaagga tttacgctca ggttatgaaa ctttcaaagt     1140
cattggtggt tggtccacac taattccaa atcgcagatc aatagacaag tcatagttga      1200
cagcgataat cggtcaggtt actctggtat tttctctgtt gagggcaaaa gctgcatcaa     1260
taggtgcttt tatgtggagt tgataagggg aaggaaacag gagactagag tgtggtggac     1320
ctcaaacagt attgttgtgt tttgtggcac ttcaggtacc tatggaacag gctcatggcc     1380
tgatggggcg aacatcaatt tcatgcctat ataagctttc gcaattttag a              1431
```

<210> SEQ ID NO 21
<211> LENGTH: 469
<212> TYPE: PRT
<213> ORGANISM: Influenza A virus

<400> SEQUENCE: 21

```
Met Asn Pro Asn Gln Lys Ile Ile Thr Ile Gly Ser Val Ser Leu Thr
1               5                   10                  15

Ile Ala Thr Val Cys Phe Leu Met Gln Ile Ala Ile Leu Val Thr Thr
            20                  25                  30

Val Thr Leu His Phe Lys Gln Tyr Glu Cys Asp Ser Pro Ala Ser Asn
        35                  40                  45

Gln Val Met Pro Cys Glu Pro Ile Ile Ile Glu Arg Asn Ile Thr Glu
    50                  55                  60

Ile Val Tyr Leu Asn Asn Thr Thr Ile Glu Lys Glu Ile Cys Pro Lys
65                  70                  75                  80

Val Val Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp His Gly Lys
        115                 120                 125

Cys Tyr Gln Phe Ala Leu Gly Gln Gly Thr Thr Leu Asp Asn Lys His
    130                 135                 140

Ser Asn Asp Thr Ile His Asp Arg Ile Pro His Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asp
```

-continued

```
        195                 200                 205

Gly Arg Leu Val Asp Ser Ile Gly Ser Trp Ser Gln Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Glu Glu Gly Lys Ile Val His Ile Ser Pro Leu Ser Gly Ser Ala
            260                 265                 270

Gln His Val Glu Glu Cys Ser Cys Tyr Pro Arg Tyr Pro Gly Val Arg
        275                 280                 285

Cys Ile Cys Arg Asp Asn Trp Lys Gly Ser Asn Arg Pro Val Val Asp
    290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Arg Ser Ser Asn Ser Asn
                325                 330                 335

Cys Arg Asn Pro Asn Asn Glu Arg Gly Asn Gln Gly Val Lys Gly Trp
            340                 345                 350

Ala Phe Asp Asn Gly Asp Asp Val Trp Met Gly Arg Thr Ile Ser Lys
        355                 360                 365

Asp Leu Arg Ser Gly Tyr Glu Thr Phe Lys Val Ile Gly Gly Trp Ser
    370                 375                 380

Thr Pro Asn Ser Lys Ser Gln Ile Asn Arg Gln Val Ile Val Asp Ser
385                 390                 395                 400

Asp Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465

<210> SEQ ID NO 22
<211> LENGTH: 1733
<212> TYPE: DNA
<213> ORGANISM: Influenza A virus

<400> SEQUENCE: 22
atagacaacc aaaagcaaaa caatggccat catttatctc attctcctgt tcacagcagt      60
gagaggggac cagatatgca ttggatacca tgccaataat tccacagaga aggtcgacac     120
aattctagag cggaacgtca ctgtgactca tgccaaggac attcttgaga agacccataa     180
cggaaagtta tgcaaactaa acggaatccc tccacttgaa ctaggggact gtagcattgc     240
cggatggctc cttggaaatc cagaatgtga taggcttcta agtgtgccag aatggtccta     300
tataatggag aaagaaaacc cgagagacgg tttgtgttat ccaggcagct tcaatgatta     360
tgaagaattg aaacatctcc tcagcagcgt gaaacatttc gagaaagtaa agattctgcc     420
caaagataga tggacacagc atacaacaac tggaggttca cgggcctgcg cggtgtctgg     480
taatccatca ttcttcagga acatgatctg gctgacaaag aaaggatcaa attatccggt     540
```

```
tgccaaagga tcgtacaaca atacaagcgg agaacaaatg ctaataattt ggggggtgca    600
ccatcccaat gatgagacag aacaaagaac attgtaccag aatgtgggaa cctatgtttc    660
cgtaggcaca tcaacattga acaaaaggtc aaccccagac atagcaacaa ggcctaaagt    720
gaatggacta ggaagtagaa tggaattctc ttggacccta ttggatatgt gggacaccat    780
aaattttgag agtactggta atctaattgc accagagtat ggattcaaaa tatcgaaaag    840
aggtagttca gggatcatga aaacagaagg aacacttggg aactgtgaga ccaaatgcca    900
aactcctttg ggagcaataa atacaacatt gcctttttcac aatgtccacc cactgacaat    960
aggtgagtgc cccaaatatg taaaatcgga gaagttggtc ttagcaacag gactaaggaa   1020
tgttccccag attgaatcaa gaggattgtt tgggcaata gctggtttta tagaaggagg   1080
atggcaagga atggttgatg gttggtatgg ataccatcac agcaatgacc agggatcagg   1140
gtatgcagcg gacaaagaat ccactcaaaa ggcatttgat ggaatcacca acaaggtaaa   1200
ttctgtgatt gaaagatgaa cacccaattt gaagctgtt gggaaagaat tcagtaactt   1260
agagagaaga ctggagaact tgaacaaaaa gatggaagac gggtttctag atgtgtggac   1320
atacaatgct gagcttctag ttctgatgga aaatgagagg acacttgact ttcatgattc   1380
taatgtcaag aatctgtatg ataaagtcag aatgcagctg agagacaacg tcaaagaact   1440
aggaaatgga tgttttgaat tttatcacaa atgtgatgat gaatgcatga atagtgtgaa   1500
aaacgggacg tatgattatc ccaagtatga agaagagtct aaactaaata gaatgaaat   1560 caaagggggta aaattgagca gcatgggggt ttatcaaatc cttgccattt atgctacagt   1620
agcaggttct ctgtcactgg caatcatgat ggctgggatc tctttctgga tgtgctccaa   1680
cgggtctctg cagtgcagga tctgcatatg attataagtc attttataat taa          1733

<210> SEQ ID NO 23
<211> LENGTH: 562
<212> TYPE: PRT
<213> ORGANISM: Influenza A virus

<400> SEQUENCE: 23

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
                20                  25                  30

Thr Ile Leu Glu Arg Asn Val Thr Val Thr His Ala Lys Asp Ile Leu
            35                  40                  45

Glu Lys Thr His Asn Gly Lys Leu Cys Lys Leu Asn Gly Ile Pro Pro
        50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Ile Trp Leu Thr Lys Lys Gly Ser Asn Tyr Pro Val Ala Lys Gly
```

```
                    165                 170                 175
Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
            195                 200                 205

Gly Thr Tyr Val Ser Val Gly Thr Ser Thr Leu Asn Lys Arg Ser Thr
            210                 215                 220

Pro Asp Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Gly Asn Cys
            275                 280                 285

Glu Thr Lys Cys Gln Thr Pro Leu Gly Ala Ile Asn Thr Thr Leu Pro
            290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
            355                 360                 365

Asp Gln Gly Ser Gly Tyr Ala Ala Asp Lys Glu Ser Thr Gln Lys Ala
            370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
            435                 440                 445

Asp Phe His Asp Ser Asn Val Lys Asn Leu Tyr Asp Lys Val Arg Met
            450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Ser Lys Leu Asn Arg Asn Glu
            500                 505                 510

Ile Lys Gly Val Lys Leu Ser Ser Met Gly Val Tyr Gln Ile Leu Ala
            515                 520                 525

Ile Tyr Ala Thr Val Ala Gly Ser Leu Ser Leu Ala Ile Met Met Ala
            530                 535                 540

Gly Ile Ser Phe Trp Met Cys Ser Asn Gly Ser Leu Gln Cys Arg Ile
545                 550                 555                 560

Cys Ile

<210> SEQ ID NO 24
<211> LENGTH: 1435
```

<212> TYPE: DNA
<213> ORGANISM: Influenza A virus

<400> SEQUENCE: 24

```
tgaaaatgaa tccaaatcaa aagataataa caattggctc tgtctctctc accattgcaa     60
cagtatgctt cctcatgcag attgccatcc tggcaactac tgtgacattg cattttaaac    120
aacatgagtg cgactccccc gcgagcaacc aagtaatgcc atgtgaacca ataataatag    180
aaaggaacat aacagagata gtgtatttga ataacaccac catagagaaa gagatttgcc    240
ccgaagtagt ggaatacaga aattggtcaa agccgcaatg tcaaattaca ggatttgcac    300
ctttttctaa ggacaattca atccggcttt ctgctggtgg ggacatttgg gtgacgagag    360
aaccttatgt gtcatgcgat cctggcaagt gttatcaatt tgcactcggg caagggacca    420
cactagacaa caaacattca aatggcacaa tacatgatag aatccctcac cgaaccctat    480
taatgaatga gttgggtgtt ccatttcatt taggaaccaa acaagtgtgt gtagcatggt    540
ccagctcaag ttgtcacgat ggaaaagcat ggttgcatgt ttgtgtcact ggggatgata    600
gaaatgcgac tgccagcttc atttatgacg ggaggcttgt ggacagtatt ggttcatggt    660
ctcaaaatat cctcaggacc caggagtcgg aatgcgtttg tatcaatggg acttgcacag    720
tagtaatgac tgatggaagt gcatcaggaa gagccgatac tagaatacta ttcattaaag    780
aggggaaaat tgtccatatc agcccattgt caggaagtgc tcagcatata gaggagtgtt    840
cctgttaccc tcgatatcct gacgtcagat gtatctgcag agacaactgg aaaggctcta    900
ataggcccgt tatagacata aatatggaag attatagcat tgattccagt tatgtgtgct    960
cagggcttgt tggcgacaca cccaggaacg acgacagctc tagcaatagc aattgcaggg   1020
atcctaacaa tgagagaggg aatccaggag tgaaaggctg ggcctttgac aatggagatg   1080
atgtatggat gggaagaaca atcaacaaag attcacgctc aggttatgaa actttcaaag   1140
tcattggtgg ttggtccaca cctaattcca aatcgcaggt caatagacag gtcatagttg   1200
acaacaataa ttggtctggt tactctggta ttttctctgt tgagggcaaa agctgcatca   1260
ataggtgctt ttatgtggag ttgataaggg gaaggccaca ggagactaga gtatggtgga   1320
cctcaaacag tattgttgtg ttttgtggca cttcaggtac ttatggaaca ggctcatggc   1380
ctgatggggc gaacatcaat ttcatgccta tataagcttt cgcaatttta gaaaa         1435
```

<210> SEQ ID NO 25
<211> LENGTH: 469
<212> TYPE: PRT
<213> ORGANISM: Influenza A virus

<400> SEQUENCE: 25

```
Met Asn Pro Asn Gln Lys Ile Ile Thr Ile Gly Ser Val Ser Leu Thr
1               5                   10                  15

Ile Ala Thr Val Cys Phe Leu Met Gln Ile Ala Ile Leu Ala Thr Thr
            20                  25                  30

Val Thr Leu His Phe Lys Gln His Glu Cys Asp Ser Pro Ala Ser Asn
        35                  40                  45

Gln Val Met Pro Cys Glu Pro Ile Ile Ile Glu Arg Asn Ile Thr Glu
    50                  55                  60

Ile Val Tyr Leu Asn Asn Thr Thr Ile Glu Lys Glu Ile Cys Pro Glu
65                  70                  75                  80

Val Val Glu Tyr Arg Asn Trp Ser Lys Pro Gln Cys Gln Ile Thr Gly
                85                  90                  95
```

```
Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Gly Lys
            115                 120                 125

Cys Tyr Gln Phe Ala Leu Gly Gln Gly Thr Thr Leu Asp Asn Lys His
        130                 135                 140

Ser Asn Gly Thr Ile His Asp Arg Ile Pro His Arg Thr Leu Leu Met
145                 150                 155                 160

Asn Glu Leu Gly Val Pro Phe His Leu Gly Thr Lys Gln Val Cys Val
                165                 170                 175

Ala Trp Ser Ser Ser Cys His Asp Gly Lys Ala Trp Leu His Val
            180                 185                 190

Cys Val Thr Gly Asp Asp Arg Asn Ala Thr Ala Ser Phe Ile Tyr Asp
        195                 200                 205

Gly Arg Leu Val Asp Ser Ile Gly Ser Trp Ser Gln Asn Ile Leu Arg
        210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
            245                 250                 255

Ile Lys Glu Gly Lys Ile Val His Ile Ser Pro Leu Ser Gly Ser Ala
        260                 265                 270

Gln His Ile Glu Glu Cys Ser Cys Tyr Pro Arg Tyr Pro Asp Val Arg
        275                 280                 285

Cys Ile Cys Arg Asp Asn Trp Lys Gly Ser Asn Arg Pro Val Ile Asp
        290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Ser Ser Ser Asn Ser Asn
            325                 330                 335

Cys Arg Asp Pro Asn Asn Glu Arg Gly Asn Pro Gly Val Lys Gly Trp
        340                 345                 350

Ala Phe Asp Asn Gly Asp Asp Val Trp Met Gly Arg Thr Ile Asn Lys
        355                 360                 365

Asp Ser Arg Ser Gly Tyr Glu Thr Phe Lys Val Ile Gly Gly Trp Ser
        370                 375                 380

Thr Pro Asn Ser Lys Ser Gln Val Asn Arg Gln Val Ile Val Asp Asn
385                 390                 395                 400

Asn Asn Trp Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Pro Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
        450                 455                 460

Asn Phe Met Pro Ile
465

<210> SEQ ID NO 26
<211> LENGTH: 33
<212> TYPE: DNA
<213> ORGANISM: Artificial Sequence
<220> FEATURE:
<223> OTHER INFORMATION: 1918 H1N1 primer: HA NC F
```

```
<400> SEQUENCE: 26
caacgcgtgc caccatgaaa gcaaaactac tgg                              33

<210> SEQ ID NO 27
<211> LENGTH: 30
<212> TYPE: DNA
<213> ORGANISM: Artificial Sequence
<220> FEATURE:
<223> OTHER INFORMATION: 1918 H1N1 primer: HA NC R

<400> SEQUENCE: 27
tcggcgcctc agatgcatat tctacactgc                                  30

<210> SEQ ID NO 28
<211> LENGTH: 27
<212> TYPE: DNA
<213> ORGANISM: Artificial Sequence
<220> FEATURE:
<223> OTHER INFORMATION: 1918 H1N1 primer: NA NC F

<400> SEQUENCE: 28
caacgcgtgc caccatgaat ccaaatc                                     27

<210> SEQ ID NO 29
<211> LENGTH: 30
<212> TYPE: DNA
<213> ORGANISM: Artificial Sequence
<220> FEATURE:
<223> OTHER INFORMATION: 1918 H1N1 primer: NA NC R

<400> SEQUENCE: 29
tcggcgccct acttgtcaat ggtgaacggc                                  30
```